United States Patent
Mutharasan et al.

(10) Patent No.: US 8,512,947 B2
(45) Date of Patent: *Aug. 20, 2013

(54) DETECTION OF NUCLEIC ACIDS USING A CANTILEVER SENSOR

(75) Inventors: Rajakkannu Mutharasan, West Chester, PA (US); Kishan Rijal, Harleyville, PA (US); David R. Maraldo, Gilbertsville, PA (US); Gossett Augustus Campbell, Gilbertsville, PA (US)

(73) Assignee: Drexel University, Philadelphia, PA (US)

( * ) Notice: Subject to any disclaimer, the term of this patent is extended or adjusted under 35 U.S.C. 154(b) by 690 days.

This patent is subject to a terminal disclaimer.

(21) Appl. No.: 12/141,846

(22) Filed: Jun. 18, 2008

(65) Prior Publication Data

US 2009/0203000 A1    Aug. 13, 2009

Related U.S. Application Data

(63) Continuation-in-part of application No. 12/032,302, filed on Feb. 15, 2008, now Pat. No. 7,892,759.

(60) Provisional application No. 60/890,370, filed on Feb. 16, 2007, provisional application No. 60/944,592, filed on Jun. 18, 2007, provisional application No. 60/948,106, filed on Jul. 5, 2007.

(51) Int. Cl.
*C12Q 1/68* (2006.01)
*C12M 1/36* (2006.01)
*G01N 27/00* (2006.01)

(52) U.S. Cl.
USPC ..... 435/6.1; 435/283.1; 435/287.2; 422/68.1; 422/82.01; 536/23.1; 977/732

(58) Field of Classification Search
None
See application file for complete search history.

(56) References Cited

U.S. PATENT DOCUMENTS 3,560,099 A   2/1971   Boe et al.
4,186,599 A   2/1980   Frick (Continued)

FOREIGN PATENT DOCUMENTS

EP   0631319 A1   12/1994
EP   1536227 A2    6/2005

(Continued)

OTHER PUBLICATIONS

Campbell, G.A., et al., "Method of Measuring *Bacillus anthracis* spores in the presence of copious amounts of *Bacillus thuringiensis* and *Bacillus cereus*," Anal. Chem., published online Dec. 22, 2006, 79(3), 1145-1152.

(Continued)

*Primary Examiner* — Betty Forman
(74) *Attorney, Agent, or Firm* — Woodcock Washburn, LLP

(57) ABSTRACT

Detection of miniscule amounts of nucleic acid is accomplished via binding of target nucleic acid to probe material, composed of nucleic acid, which is bound to a sensor configured to sense mass. The sensor is prepared by immobilizing a probe material to a surface of the sensor, wherein the probe material is known to bind to the target nucleic acid. The prepared sensor is exposed to the target nucleic acid. The target nucleic acid binds to the probe material. The mass accumulated on the sensor reflects the amount of target nucleic acid bound to the probe material.

29 Claims, 42 Drawing Sheets

(56) References Cited

U.S. PATENT DOCUMENTS

| | | | |
|---|---|---|---|
| 4,791,818 A | 12/1988 | Wilde et al. | |
| 5,116,759 A | 5/1992 | Klainer et al. | |
| 5,445,008 A | 8/1995 | Wachter et al. | |
| 5,583,300 A | 12/1996 | Green et al. | |
| 5,719,324 A | 2/1998 | Thundat et al. | |
| 5,770,462 A | 6/1998 | Molloy | |
| 6,170,981 B1 | 1/2001 | Regnier et al. | |
| 6,274,723 B1 | 8/2001 | Nilsen | |
| 6,336,366 B1 | 1/2002 | Thundat et al. | |
| 6,543,274 B1 | 4/2003 | Herrmann et al. | |
| 6,589,727 B1 | 7/2003 | Kleneman et al. | |
| 6,880,402 B1 | 4/2005 | Couet et al. | |
| 7,105,301 B2* | 9/2006 | Su et al. | 435/6 |
| 7,195,909 B2 | 3/2007 | Kleneman et al. | |
| 7,263,874 B2 | 9/2007 | Fitch et al. | |
| 7,409,851 B2* | 8/2008 | Ilic et al. | 73/24.06 |
| 7,458,265 B2* | 12/2008 | Shih et al. | 73/579 |
| 7,504,219 B2* | 3/2009 | Bickmore, Jr. et al. | 435/6 |
| 7,892,759 B2* | 2/2011 | Mutharasan et al. | 435/7.1 |
| 8,171,795 B1* | 5/2012 | Mutharasan et al. | 73/579 |
| 2002/0012616 A1 | 1/2002 | Zhou et al. | |
| 2002/0092340 A1 | 7/2002 | Prater et al. | |
| 2003/0194697 A1 | 10/2003 | Kleneman et al. | |
| 2003/0215816 A1* | 11/2003 | Sundararajan et al. | 435/6 |
| 2003/0224551 A1 | 12/2003 | Kim et al. | |
| 2004/0115711 A1* | 6/2004 | Su et al. | 435/6 |
| 2004/0197845 A1 | 10/2004 | Hassibi et al. | |
| 2005/0063882 A1 | 3/2005 | Centanni et al. | |
| 2005/0112621 A1 | 5/2005 | Kim et al. | |
| 2005/0164299 A1 | 7/2005 | Stewart | |
| 2005/0229677 A1 | 10/2005 | Tuller et al. | |
| 2005/0277852 A1 | 12/2005 | Shih et al. | |
| 2006/0053870 A1 | 3/2006 | Berndt | |
| 2006/0065046 A1 | 3/2006 | Battiston et al. | |
| 2006/0160098 A1 | 7/2006 | Zak et al. | |
| 2006/0196253 A1 | 9/2006 | Crawley et al. | |
| 2006/0223171 A1 | 10/2006 | Craighead et al. | |
| 2006/0228657 A1 | 10/2006 | Masters et al. | |
| 2007/0089515 A1 | 4/2007 | Shih et al. | |
| 2007/0169553 A1 | 7/2007 | Mutharasan et al. | |
| 2007/0218534 A1 | 9/2007 | Klenerman et al. | |
| 2008/0034840 A1 | 2/2008 | Mutharasan et al. | |
| 2008/0035180 A1 | 2/2008 | Mutharasan et al. | |
| 2009/0078023 A1 | 3/2009 | Mutharasan et al. | |
| 2011/0138915 A1* | 6/2011 | Mutharasan et al. | 73/579 |

FOREIGN PATENT DOCUMENTS

| | | |
|---|---|---|
| WO | 98/50773 A2 | 11/1998 |
| WO | 2005/043126 A2 | 5/2005 |
| WO | WO 2005-043126 | 5/2005 |

OTHER PUBLICATIONS

Campbell, G.A., et al., "*Escherichia coli* O157:H7 detection limit of millimeter-sized PZT cantilever sensors in 700 cells/mL," Analytical Sci., Apr. 21, 2005, 11-13.

Campbell, G.A., et al., "Detection of pathogen *Escherichia coli* O157:H7 using self-excited PZT-glass microcantilevers," Biosensors and Bioelectronics, Sep. 15, 2005, Epub Dec. 21, 2004, 21(3), 462-473.

Campbell, G.A., et al., "Detect of *Escherichia coli* O157:H7 in ground beef samples using piezoelectric excited millimeter-sized cantilever (PEMC) sensors," Biosens Bioelectron, Feb. 15, 2007, Epub Jul. 10, 2006, 22(7), 1296-1302.

Campbell, G.A., et al.,"A method of measuring *Escherichia coli* O157:H7 at 1 cell/mL in 1 liter sample using antibody functional piezoelectric-excited millimeter-sized cantilever sensor," Environ. Sci. Technol., published online Jan. 23, 2007, 41(5), 1668-1674.

Campbell, G.A., et al., "Detection and quantification of proteins using self-excited PZT-glass millimeter-sized cantilever," Biosensors and Bioelectronics, 2005, 21, 597-607.

Campbell, G.A., et al., "Piezoelectric-excited millimeter-sized cantilever (PEMC) sensors detect *Bacillus anthracis* at 300 spores/mL," Biosensors Bioelectronics, 2006, 21, 1684-1692.

Campbell, G.A., et al., "Detection of *Bacillus anthracts* spores and a model protein using PEMC sensors in a flow cell at 1 mL/MIN," Biosens Bioelectron, Jul. 15, 2006, Epub Jan. 19, 2006, 22(1), 78-85.

Campbell, G.A., et al., "Detection of airborne *Bacillus anthracis* spores by an integrated system of an air sampler and a cantilever immunosensor," Sensors and Actuators B Chemical, Nov. 15, 2007, available online May 1, 2007, 127(2), 376-382.

Campbell, G.A., et al., "PEMC sensor's mass change sensitivity in 20 PG/HZ under liquid immersion," Biosensors and Bioelectronics, Jul. 15, 2006, Epub Jan. 18, 2006, 22(1), 35-41.

Campbell, G.A., et al., "Use of Piezoelectric-Excited Millimeter-Sized Cantilever Sensors to Measure Albumin Interaction with Self-Assembled Monolayers of Alkanethiols Having Different Functional Headgroups," Anal. Chem., available online Feb. 28, 2006, 78(7), 2328-2334.

Carr, D.W., et al., "Fabrication of nanoelectromechanical systems in single crystal silicon using silicon on insulator substrates and electron beam lithography," J. Vac. Sci. Technology, B, 15(6), 2760-2763.

Maraldo, D., et al., "Method for Quantification of a Prostate Cancer Biomarker in Urine without Sample Preparation," Analytical Chem., Available online Sep. 15, 2007, 79(20), 7683-7690.

Maraldo, D., et al., "Preparation-free method for detecting *Escherichia coli* O157:H7 in the presence of spinach, spring lettuce mix, and ground beef particulates," J. of Food protection, Nov. 2007, 70(11) 2651-2655.

Maraldo, D., et al., "Detection and confirmation of *Staphylococcal* enterotoxin B in apple juice and milk using Piezoelectric-excited Millimeter-sized cantilever (PEMC) sensors at 2.5 femtograms/mL," Analytical Chem., 2007, 79, 7636-7643.

Maraldo, D., et al., "10-minute assay for detecting *Escherichia coli* O157:H7 in ground beef samples using piezoelectric-excited millimeter-sized cantilever (PEMC) sensors," J. of Food Protection, 2007, 70(7), 1670-1677.

Maraldo, D. et al., "Method for Label-Free Detection of Femtogram Quantities of Biologics in Flowing Liquid Samples," Anal. Chem., Apr. 1, 2007, 79(7), 2762-2770.

Rijal, K., et al., "PEMC-based method of measuring DNA hybridization at femtomolar concentration directly in human serum and in the presence of copious non-complementary strands," Analytical Chem., 2007, 79, 7392-7400.

Rijal, K., et al., "A method for measuring self-assembly of alkanethiols on gold at femtomolar concentrations," Langmuir, 2007, 23, 6856-6863.

Seung S. Lee, et al., "Self-excited piezoelectric cantilever oscillators," Transducers '95- Eurosensors IX, The 8th Int. Conf. on Solid-State Sensors and Actuators, and Eurosensors IX, Stockholm, Sweden, Jun. 25-29, 1995, 417-420.

Wilson, L., et al., "Viscosity and density values from excitation level response of piezoelectric-excited cantilever sensors," Sensors and Actuators A, Jul. 20, 2007, 138, 44-51.

Yi Jeong W. et al., "In situ cell detection using piezoelectric lead zirconate titanate-stainless steel cantilevers," J Applied Physics, Jan. 1, 2003, 93(1), 619-625.

Zhou J. et al., "Zeolite-modified microcantilever gas sensor for indoor air quality control," Sensors and Actuators B, Oct. 1, 2003, 94(3), 337-342.

* cited by examiner

Probe     HS-C$_6$H$_{12}$-5'- GGA AGA AGC TTG CTT-3'
cTarget      5'-AAG CAA GCT T-3'
SNP Target 5'-AAG CCA GCT T-3'

FIGURE 27

DETECTION OF NUCLEIC ACIDS USING A CANTILEVER SENSOR

CROSS REFERENCE TO RELATED APPLICATIONS

The present application is a continuation-in-part of and claims priority to U.S. patent application Ser. No. 12/032,302, entitled "ENHANCED SENSITIVITY OF A SELF-EXCITED PIEZOELECTRIC CANTILEVER SENSOR VIA ADDITIONAL ANTIBODY BINDING," filed Feb. 15, 2008, which claims priority to U.S. Provisional Patent Application No. 60/890,370, filed Feb. 16, 2007. U.S. patent application Ser. No. 12/032,302 issued on Feb. 22, 2011 with U.S. Pat. No. 7,892,759. The present application claims priority to U.S. Provisional Patent Application No. 60/944,592, entitled "SINGLE NUCLEOTIDE POLYMORPHISM DETECTION," filed Jun. 18, 2007, and U.S. Provisional Patent Application No. 60/948,106, entitled "DETECTION OF DNA STRANDS IN BUFFER AND COMPLEX MEDIA THROUGH DIRECT HYBRIDIZATION AND BY EXTENSION USING POLYMERASE," filed Jul. 5, 2007. Each of the above applications is entirely incorporated herein by reference.

TECHNICAL FIELD

The technical field generally relates to the detection of nucleic acids in a liquid or gas media. More particularly, the technical field relates to the use of a cantilever sensor to provide very sensitive detection of nucleic acids in liquid or gas media via nucleic acid binding.

BACKGROUND

Pathogens can be dangerous to the public. For example, Enterohemorrhagic *Escherichia coli* O157:H7 (*E. coli* O157:H7), a foodborne pathogen, is a facultative gram-negative *bacillus* that is dangerous and has been implicated in outbreaks of illness due to ingestion of meats, water, and uncooked fruits and vegetables. *E. coli* 157:H7 is capable of producing a variety of human illnesses which include hemolytic uremic syndrome and diarrhea. The outbreaks of *E. coli* O157:H7 food poisoning in the US over the past few decades and the sporadic worldwide outbreaks caused by contaminated ground beef has raised growing interest in rapid pathogen identification.

Current methods for detecting foodborne pathogens are time consuming and not very sensitive. Traditionally, detection of foodborne pathogens has involved sample collection, enrichment, followed by isolation and identification of the targeted organism by a variety of methods. The current methods capable of foodborne pathogen detection include traditional enrichment and plating methods in selective media, polymerase chain reaction (PCR), fiber optic biosensors, immuno-magnetic beads, and quartz crystal microbalance (QCM). Each of the stated methods has its own set of limitations. Enrichment and plating approach lack sensitivity and specificity, and often takes 24-96 hours to identify the contaminant organism. Most immuno-magnetic assays and fiber optic biosensors require pre-enrichment of the sample since the pathogenic bacteria is present in concentrations below the technology's limit of detection. In addition to sample enrichment requirements, PCR methods have a higher cost, and require well-trained personnel. QCM analysis is not very sensitive and, therefore its use is limited when pathogen is present at high concentration with a high level of contaminants. In addition to the individual limitations, the current methods of food sampling do not ensure 100% absence of unwanted, potentially cross-reactive, contaminants due to the intrinsic nature of sample collection.

SUMMARY

Cantilever sensors, such as piezoelectric cantilever sensors, bending mode cantilever sensors, QCM cantilever sensors, or the like, are used to detect target nucleic acid via binding of the target nucleic acid to a probe material accumulated on the sensor. Neither the target nucleic acid nor the probe material needs to be labeled. A sensor is prepared by immobilizing a probe material on a cantilever surface of the sensor. The immobilized probe material is known to bind (bindable) to a target nucleic acid. The prepared sensor is exposed to the target nucleic acid. The target nucleic acid binds to the probe material immobilized on the surface of the cantilever sensor, resulting in an increase in the effective mass of the cantilever sensor. The cantilever sensor responds to changes in mass that occur due to binding of target nucleic acids to the sensor surface, as observed via a corresponding change in resonance frequency of the sensor. The portion of the total mass accumulated on the sensor that is attributable to the target nucleic acid is determined. Labeling of the target nucleic acid is not required because the sensor can detect minute quantities of target nucleic acid. For example, quantities of target nucleic acid as small as 1 aM ($10^{-18}$ Moles) are detectable. Further, purification of the target nucleic acid is not required. Thus, the sensor quantifiably detects target nucleic acid in complex solutions that contain proteins, lipids, sugars, DNA, RNA, or combinations thereof. Complex solutions of target nucleic acid may include bodily fluids, such as blood serum, urine, saliva, and/or various food preparations, such as beverages, juices, or the like.

In an example embodiment, the prepared sensor is exposed to a target nucleic acid and a polymerase, in which case the polymerase contributes to the mass accumulated on the sensor. The polymerase is used to catalyze a reaction in which at least one nucleotide is added to the nucleic acid portion of the probe material. The addition of nucleotides to the probe material results in further accumulation of mass on the sensor and therefore further changes in resonance frequency. The polymerase catalysis can occur at a constant temperature, such as room temperature (e.g., 37° C.) for example. The polymerase catalysis can occur in the absence of thermal cycling (e.g., alternately heating and cooling a sample to a defined series of temperature steps). Convention polymerase chain reactions require high temperatures to physically separate nucleic acid strands (also known as denaturing, dehybridizing, or melting); and using low temperatures to allow complementary strands to hybridize (also know as annealing or binding), which allows the polymerase to catalyze the polymerase reaction. Utilization of the herein described mass sensing sensor and processes avoids the aforementioned thermal cycling steps required in conventional polymerase chain reactions.

The target nucleic acid is complementary to at least a portion of a nucleic acid of the probe material. The target nucleic acid can contain a single nucleotide that is not complementary to a corresponding nucleotide in a portion of a nucleic acid of the probe material. This difference in nucleotide identity is referred to as a base pair mismatch or single nucleotide polymorphism. In some instances, whether the target nucleic acid and probe material contain a region of complete complementarity or a base pair mismatch is not known a priori. Characterizing the kinetics of the binding between the target nucleic acid and probe material indicates whether the binding involves complete complementary base pairing or base pair mismatches. The change in resonance frequency over time reflects the kinetics of the binding reaction between the target nucleic acid and the probe material (or binding partners). The rate at which the binding reactions reach equilibrium is utilizable to quantify the affinity of the binding partners for one another, which in turn facilitates identification of binding partners. Monitoring the resonance frequency change provides quantitative measures of the target nucleic acid in the sample.

Even where, a priori, a target nucleic acid and probe material are known to contain a region of complete complementarity or a base pair mismatch, the sensor can be used to confirm the binding between the binding partners. A sensor is prepared by immobilizing a probe material on a cantilever surface of the sensor. The immobilized probe material is known to bind (bindable) to a target nucleic acid. A first resonance frequency of the sensor is measured by exposing the prepared sensor to the target nucleic acid. An increase in an electrical parameter of excitation, such as voltage or frequency, is applied to the sensor, and a second resonance frequency of the sensor is measured. The difference between the first resonance frequency and the second resonance frequency reflects an amount of target nucleic acid on the sensor. The difference in the first resonance frequency and the second resonance frequency is indicative of target nucleic acid denaturing (unbinding) from the probe material. The difference in the first resonance frequency and the second resonance frequency is indicative of an amount of target nucleic acid that had been hybridized to the probe material.

In some instances, there will be no difference between the first resonance frequency and the second resonance frequency, in which case a further increase in an electrical parameter of excitation is applied to the sensor, and a third resonance frequency of the sensor is measured. The third resonance frequency is compared with the second resonance frequency to determine whether there is a difference between the two. If there is no difference, the process of increasing an electrical parameter of excitation and comparing the resulting resonance frequency is repeated until a difference between the resulting sequentially measured resonance frequencies is detected. Differences in sequentially measured resonance frequencies reflect an amount of target nucleic acid on the sensor, target nucleic acid denaturing (unbinding) from the probe material, and/or an amount of target nucleic acid that was hybridized to the probe material.

Mechanical sensors are useful for detecting dehybridization that is not dependent upon changes in a sample solution, such as by adding acids, salts, solvents, chaotropic agents, reducing agents, or increased temperature. Detecting dehybridization using a mechanical sensor comprises (a) immobilizing a probe material to a surface of a sensor, wherein the probe material is bindable to the target nucleic acid; (b) applying a first excitation voltage to the sensor and measuring a first resonance frequency of the sensor; (c) exposing the sensor surface, having the probe material immobilized thereon, to the target nucleic acid and measuring a second resonance frequency of the sensor while applying the first excitation voltage from step (b) to the sensor; (d) applying at least one of an increased voltage at a first excitation frequency to the sensor and measuring a third resonance frequency of the sensor; (e) applying the first excitation voltage to the sensor and measuring a fourth resonance frequency of the sensor; (f) determining a difference between the second resonance frequency and the fourth resonance frequency; and (g) determining if dehybridization between the target nucleic acid and the probe material has occurred in accordance with a value of the difference. A value of difference of zero is indicative of lack of dehybridization between the target nucleic acid and the probe material.

Where a zero value is determined the steps may be repeated by applying further increased voltage to the sensor, followed by applying the first excitation voltage, and comparing the resonance frequency to the second resonance frequency measured in step (c). The first resonance frequency reflects the baseline resonance frequency of the sensor. The second resonance frequency reflects the hybridization of target nucleic acid to the probe material immobilized on the sensor. The third resonance frequency reflects a change in fluid dynamics of the sensor in response to the increased voltage. The fourth resonance frequency reflects an amount of target nucleic acid rehybridized to the probe material. A difference between the first and second resonance frequency is indicative of an amount of a target nucleic acid hybridized to the probe material. A difference between the first and fourth resonance frequency is indicative of an amount of a target nucleic acid hybridized to the probe material. A difference between the second and fourth resonance frequency is indicative of an amount of a target nucleic acid dehybridized from the probe material. No difference between the second and fourth resonance frequency is indicative of an amount of target nucleic acid rehybridized to the probe material.

Various sensors may be used to dehybridize (or denature) nucleic acids that are hybridized. These sensors include optical sensors, such as SPR, and optical resonator, such as whispering gallery sensors. Dehybridization of a target nucleic acid and a probe material may be accomplished by (a) immobilizing a probe material to a surface of a sensor, wherein the probe material is bindable to the target nucleic acid; (b) exposing the surface of the sensor to the target nucleic acid, wherein the target nucleic acid is present in a fluid flow field; and (c) applying vibration to the sensor surface that introduces surface displacement and acceleration.

BRIEF DESCRIPTION OF THE DRAWINGS

The foregoing summary, as well as the following detailed description, is better understood when read in conjunction with the appended drawings. For the purpose of illustrating nucleic acid detection by a cantilever sensor, there is shown in the drawings exemplary constructions thereof; however, nucleic acid detection by a cantilever sensor is not limited to the specific methods and instrumentalities disclosed.

FIG. 27 is an illustration of the nucleic acids of the probe material ("Probe") (SEQ ID NO:3), the complete complementary target nucleic acid ("cTarget") (SEQ ID NO:4), and the target nucleic acid ("SNP Target") (SEQ ID NO:14) containing a single nucleotide mismatch (underlined) with the cTarget (underlined) and the corresponding region of the probe material (underlined).

DETAILED DESCRIPTION OF ILLUSTRATIVE EMBODIMENTS

Figure 1:
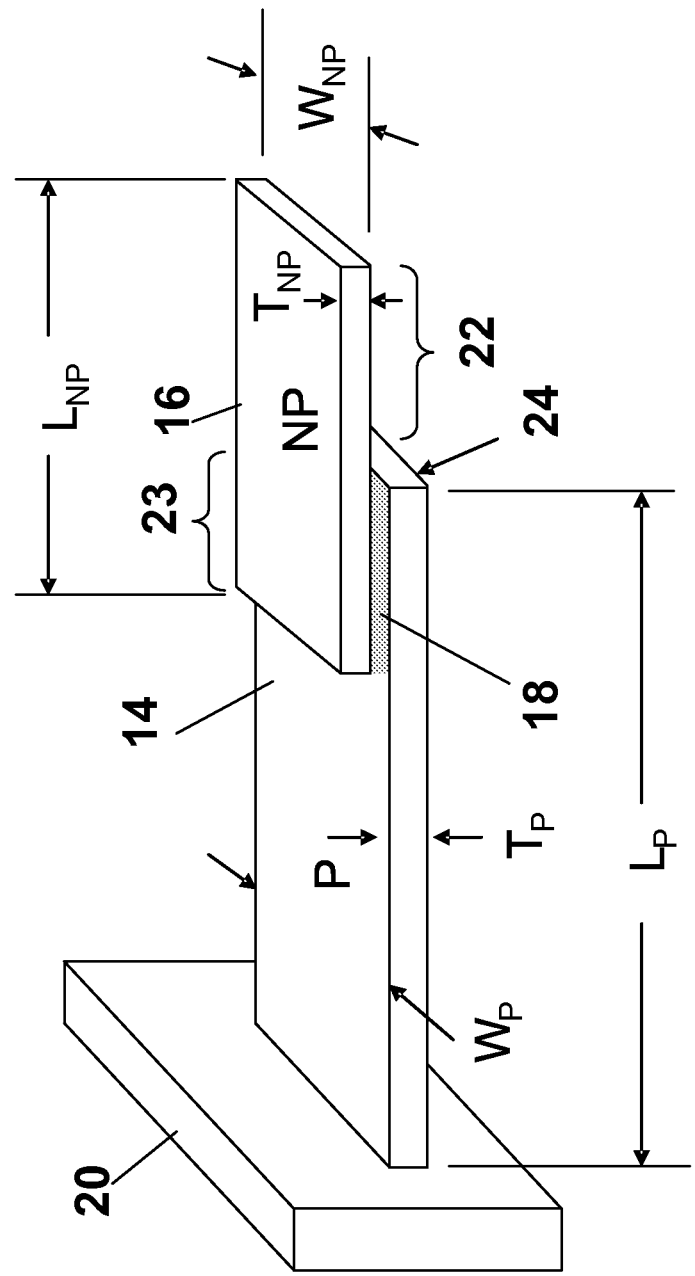
FIG. 1 is an illustration of an example configuration of a piezoelectric cantilever sensor.

As used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

As described herein, the ability to detect incredibly small masses of a target nucleic acids and changes in mass of a target nucleic acid is achieved via the use of a piezoelectric-excited cantilever sensor and binding of a target nucleic acid to a probe material as described herein. Nucleic acids can comprise DNA or RNA, including single stranded DNA or RNA, partially denatured double stranded DNA, cDNA molecule, cRNA molecule, RNA molecule, RNAi molecule, pRNA molecule. The nucleic acids may be labeled with dyes, metals, enzymes, or radioactivity to increase the mass and facilitate detection when bound.

Although detection of a target nucleic via binding of a probe material is described herein with respect to piezoelectric cantilever sensors, it is to be understood however, that any appropriate sensor can be utilized, and that the herein described processes and techniques are not limited to only piezoelectric cantilever sensors. For example, the herein described processes and techniques are applicable to bending mode cantilever sensors and QCM sensors. In an example embodiment, selectivity to a target nucleic acid is achieved by immobilizing probe material to the sensor. The probe material is known to bind (bindable) to a target material.

Sensor Overview

An example piezoelectric cantilever sensor comprises a piezoelectric layer acting as an actuating and a sensing element, and a borosilicate glass surface for nucleic acid attachment. In an example configuration, piezoelectric lead zirconate titanate (PZT) substrates are utilized to provide sensitive responses to small stresses due to the direct piezoelectric effect, and the generation of high strain via the inverse piezoelectric phenomena. Millimeter-sized piezoelectric cantilever sensors are described in some applications herein as applied to enhanced sensitivity of a self-excited piezoelectric cantilever sensor via additional antibody binding, but are not limited thereto. Smaller sized (e.g., micro/nano sized) piezoelectric cantilever sensors are applicable to achieve enhanced sensitivity of a self-excited piezoelectric cantilever sensor via additional antibody binding. In example configurations, piezoelectric-excited millimeter-sized cantilever (PEMC) sensors use the direct piezoelectric effect to excite the cantilever, and the same PZT film is used to sense the response. When an electric field is applied across the thickness of the PZT film, it extends along its length causing the base glass cantilever to bend. If the applied field is alternated periodically, the composite cantilever vibrates. The natural frequency of the cantilever depends on the flexural modulus and the mass density of the composite cantilever. At resonance, the cantilever undergoes significantly higher stresses when the exciting electric field is at resonance frequency. Hence, the PZT layer exhibits a sharp change in electrical impedance, and the resonance state can be followed by the phase angle.

FIG. 1 is an illustration of an example piezoelectric cantilever sensor 12. A piezoelectric cantilever sensor is described herein to provide an understanding of detecting a target nucleic acid via additional binding of specific material. It is to be understood however, that other cantilever sensors are applicable, such as for example, bending mode cantilever sensors and QCM sensors.

The piezoelectric cantilever sensor 12 comprises a piezoelectric portion 14 and a non-piezoelectric portion 16. Piezoelectric portions are labeled with an uppercase letter p ("P"), and non-piezoelectric portions are labeled with the uppercase letters np ("NP"). The piezoelectric cantilever sensor 12 depicts an embodiment of an unanchored, overhang, piezoelectric cantilever sensor. The piezoelectric cantilever sensor 12 is termed "unanchored" because the non-piezoelectric layer 16 is not attached to the base portion 20. The piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric cantilever sensor 12 provides the ability to detect and measure extremely small amounts of a nucleic acid. The piezoelectric cantilever sensor 12 can be utilized to detect and measure a nucleic acid immersed in a liquid and a nucleic acid contained in a gas or vacuum. In various example configurations, the piezoelectric cantilever sensor 12 comprises at least one piezoelectric layer 14 and at least one non-piezoelectric layer 16, wherein the piezoelectric layer 14 is coupled to the non-piezoelectric layer 16. The piezoelectric layer 14, the non-piezoelectric layer 16, or both can be coupled to at least one base 20. The piezoelectric layer and the non-piezoelectric layer can be of varying widths ($W_P$), lengths ($L_P$, $L_{NP}$), and thicknesses ($T_P$, $T_{NP}$).

The piezoelectric cantilever sensor 12 is utilizable to determine the mass of a nucleic acid accumulated thereon. In an example embodiment, a portion of the piezoelectric cantilever sensor is placed in a medium (e.g., liquid, gas, vacuum). While in the medium, a resonance frequency of the piezoelectric cantilever sensor is measured and compared to a baseline resonance frequency. The difference in the measured resonance frequency and the baseline resonance frequency is indicative of an amount of mass of nucleic acid accumulated (e.g., bound, adsorbed, absorbed) on the piezoelectric cantilever sensor.

Nucleic acids can be directly or indirectly bound to the surface of the non-piezoelectric portion 16 of the piezoelectric cantilever sensor 12. Binding of a nucleic acid to the non-piezoelectric portion 16 of the piezoelectric cantilever sensor 12 results in a change in mass of the piezoelectric cantilever sensor 12. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the piezoelectric cantilever sensor 12 is immersed in a liquid, are detectable and measurable. Resonance frequency changes, wherein at least a portion of the piezoelectric cantilever sensor is immersed in a gas or a vacuum, also are detectable and measurable.

The piezoelectric cantilever sensor 12 is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The piezoelectric cantilever sensor 12 is operateable at relative high frequencies in liquid media, gas media, and a vacuum. The piezoelectric cantilever sensor 12 thus provides extreme sensitivity to mass changes.

The piezoelectric cantilever sensor 12 is especially suitable for nucleic acid that are present at very low concentrations in complex media such as in body fluids, water, and food materials, for example.

The piezoelectric cantilever sensor 12 provides the ability to detect changes in mass accumulated thereon as small as 1 femtogram/Hz ($1 \times 10^{-15}$ grams/Hertz) or less when immersed in a liquid media. Thus, with respect to detecting changes in mass, the piezoelectric cantilever sensor 12 is approximately 1 billion times more sensitive than a 5 MHz quartz crystal micro-balance sensor, approximate one million times more sensitive than standard analytical instruments, and over a million-fold more sensitive than conventional assays for detecting nucleic acids.

The piezoelectric cantilever sensor 12 permits detection of extremely small concentrations of nucleic acid that bind to it. The piezoelectric cantilever sensor 12 is operable in media having relatively high flow rates. The piezoelectric cantilever sensor 12 is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of biomarkers in body fluids (e.g., nucleic acids that mark a specific pathology, such as a single nucleotide polymorphism associated with a disease). The piezoelectric cantilever sensor also can be used for the detection of nucleic acids at attogram levels, and for the detection of both steady state and kinetic interactions of nucleic acids.

Detection of DNA, and/or RNA at a concentration less than 1.0 femtogram per mL ($10^{-15}$ grams) and pathogens at less than 1 pathogen/mL, respectively is achievable by measuring directly in liquid using the piezoelectric cantilever sensor immobilized with nucleic acid ("probe") specific to the target nucleic acid at a frequency of about 800 kHz to 1.8 MHz. The piezoelectric cantilever sensor 12 is capable of detecting a target nucleic acid without false positives or negatives even when contaminating entities are present. The piezoelectric cantilever sensor 12 is particularly advantageous when utilized with a raw sample, and no preparation, concentrating step, and/or enrichment of any type. Detection of a target nucleic acid utilizing the piezoelectric cantilever sensor 12 can be conducted directly in raw samples under flow conditions, greater than 15 mL/minute, for example.

As described below, the sensitivity of the piezoelectric cantilever sensor 12 is due in part to the geometric design thereof. The relative lengths and widths of the piezoelectric layer 14 and the positioning of each layer with respect to other layers within the non-piezoelectric layer 16, of the piezoelectric cantilever sensor 12 determine the sensitivity, and also the shape of the peak of the frequency spectrum provided by the piezoelectric cantilever sensor 12. As described in more detail below, the piezoelectric cantilever sensor 12 comprises a piezoelectric layer 14 and a non-piezoelectric layer 16 coupled together.

The sensitivity of the piezoelectric cantilever sensor 12 is due in part to utilizing the piezoelectric layer 14 of the piezoelectric cantilever sensor 12 for both actuation and sensing of the electromechanical properties of the piezoelectric layer 14 of the piezoelectric cantilever sensor 12. At resonance, the oscillating cantilever concentrates stress toward an area of low bending modulus. This results in an amplified change in the resistive component of the piezoelectric layer 14 and a large shift in resonance frequency. Directing this stress to a portion of the piezoelectric layer 14 having a low bending modulus allows for exploitation of the associated shift in resonance frequency to detect extremely small changes in mass of the piezoelectric cantilever sensor 12. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

The piezoelectric portion 14 can comprise any appropriate material exhibiting piezoelectric properties, such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 10 micrometers ($10 \times 10^{-6}$ meters) to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
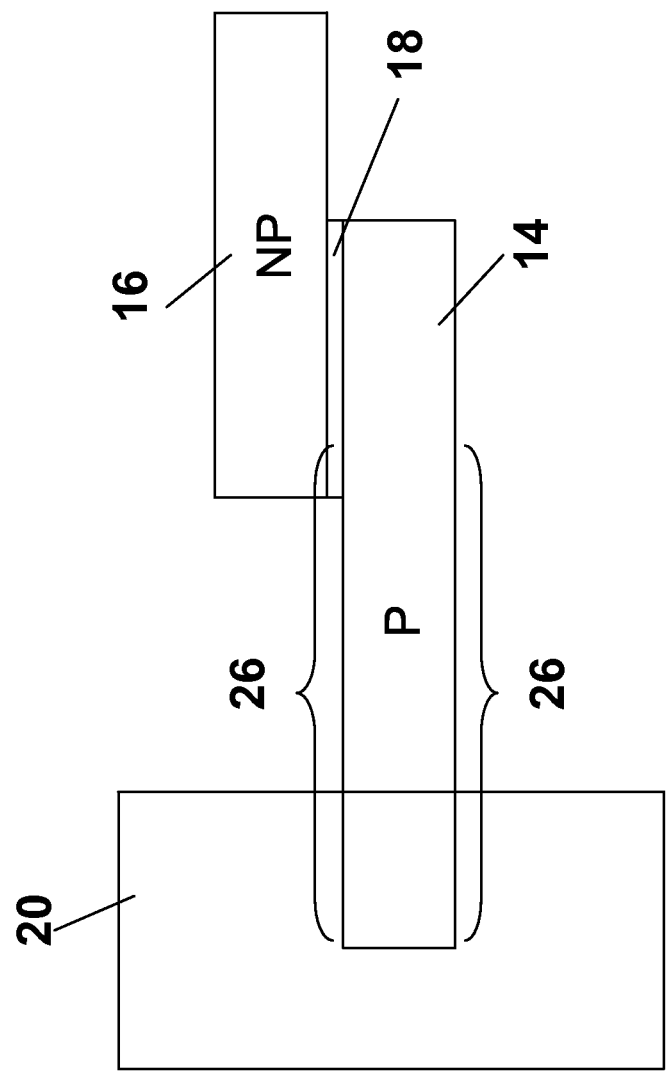
FIG. 2 is a cross-sectional view of an example piezoelectric cantilever sensor depicting electrode placement regions for electrodes operationally associated with the piezoelectric layer.
Figure 3:
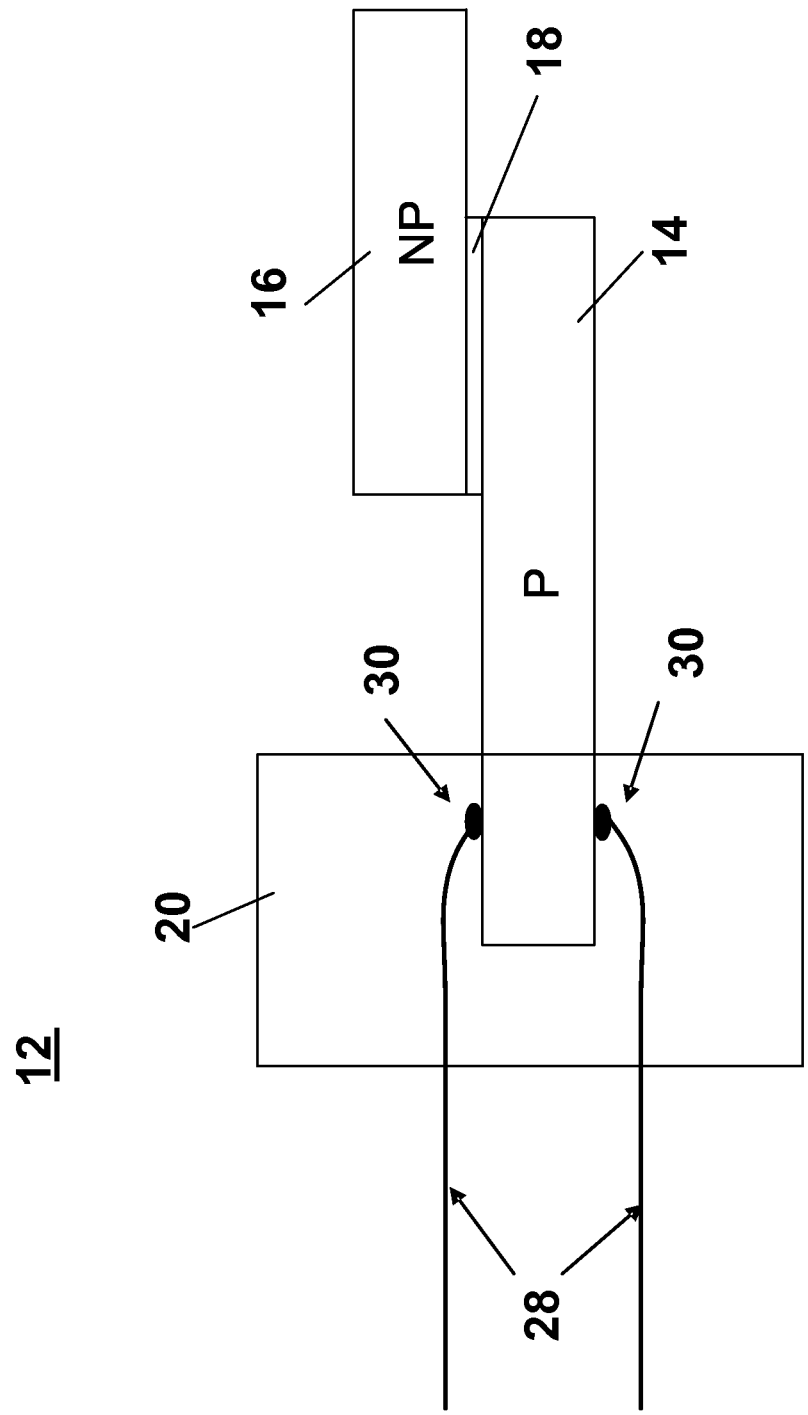
FIG. 3 is a cross-sectional view of an example piezoelectric cantilever sensor showing depicting example electrode placement within a base portion of the self-exciting, self-sensing piezoelectric cantilever sensor.
Figure 4:
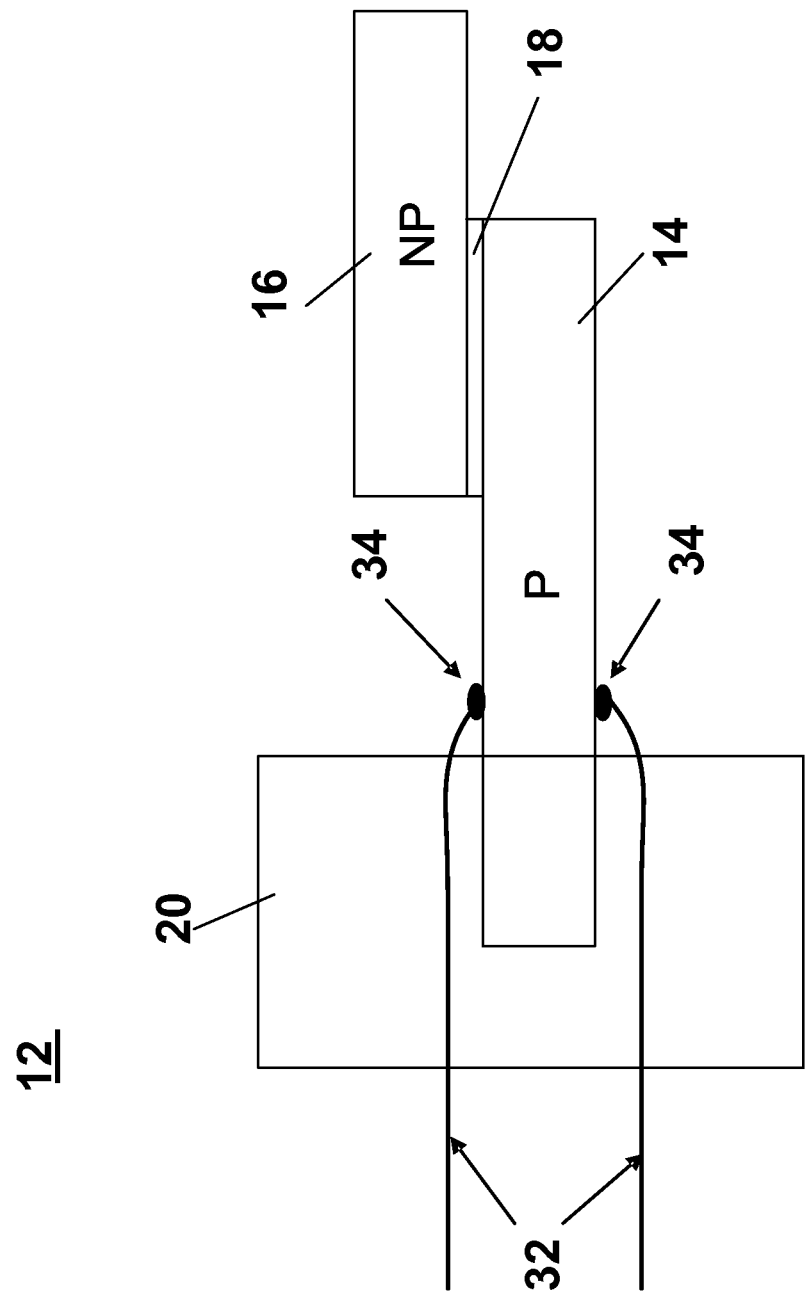
FIG. 4 is a cross-sectional view of an example piezoelectric cantilever sensor depicting example electrode placement not within a base portion of the self-exciting, self-sensing piezoelectric cantilever sensor.

FIG. 2 is a cross-sectional view of the piezoelectric cantilever sensor 12 depicting electrode placement regions 26 for electrodes operationally associated with the piezoelectric portion 14. Electrodes can be placed at any appropriate location on the piezoelectric portion of the piezoelectric cantilever sensor 12 as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location on the piezoelectric cantilever sensor 12. In an example embodiment, electrodes are operatively located near a location of concentrated stress in the piezoelectric layer 14. As described above, the sensitivity of the piezoelectric cantilever sensor is due in part to advantageously directing (concentrating) the stress in the piezoelectric layer 14 and placing electrodes proximate thereto. The configurations of the piezoelectric cantilever sensor described herein (and variants thereof) tend to concentrate oscillation associated stress in the piezoelectric layer 14. At resonance, in some of the configurations of the piezoelectric cantilever sensor 12, the oscillating cantilever concentrates stress in the piezoelectric layer 14 toward the base portion 20. This results in an amplified change in the resistive component of the piezoelectric layer 14 and a large shift in phase angle at resonance frequency at the locations of high stress. Directing this stress to a portion of the piezoelectric layer 14 having a low bending modulus allows for exploitation of the associated shift in resonance frequency to detect extremely small changes in mass of the piezoelectric cantilever piezoelectric cantilever sensor 12. Thus, in example configurations of the piezoelectric cantilever sensor 12, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the piezoelectric cantilever sensor. In other example configurations of the piezoelectric cantilever sensor electrodes are positioned proximate the location of concentrated stress in the piezoelectric layer regardless of the proximity of the concentrated stress to a base portion of the piezoelectric cantilever sensor.

Figure 5:
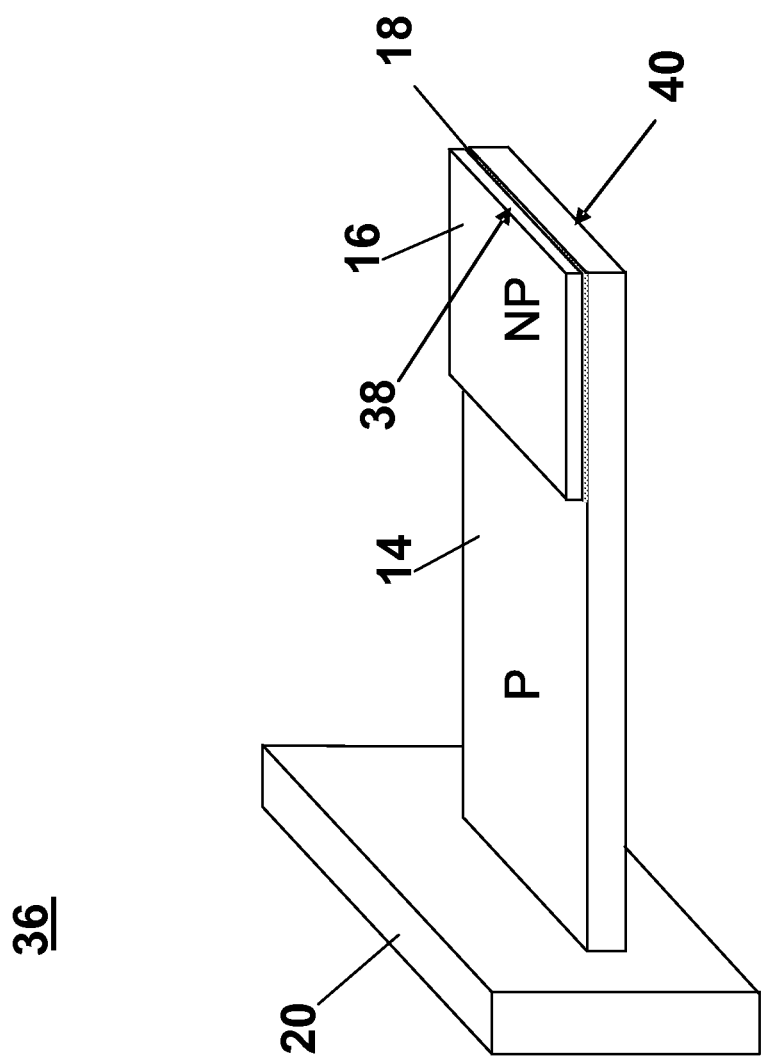
FIG. 5 is an illustration of an example configuration of a piezoelectric cantilever sensor wherein the distal end of the piezoelectric layer is flush with the distal end of the non-piezoelectric layer.
Figure 6:
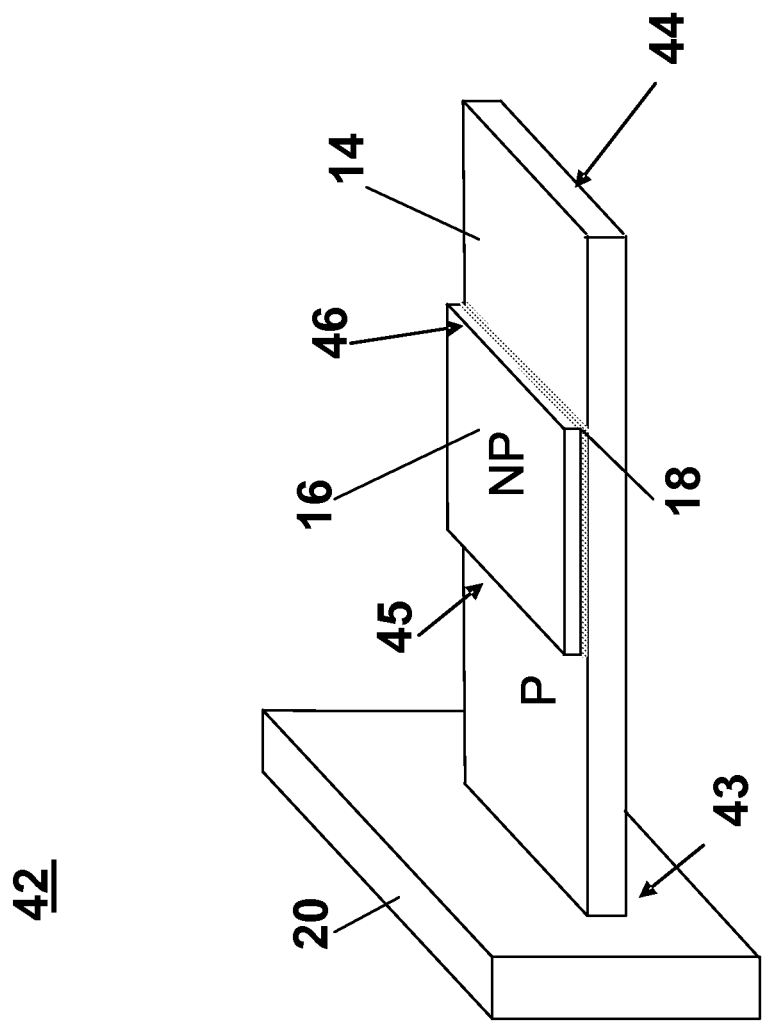
FIG. 6 is an illustration of an example configuration of a piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

The piezoelectric cantilever sensor can be configured in accordance with a plurality of configurations, some of which are depicted in FIG. 5 and FIG. 6. It is to be understood however, that the configurations depicted herein do not represent all possible configurations, but rather a representative sample of configurations of the piezoelectric cantilever sensor. FIG. 5 is an illustration of an example configuration 36 of an unanchored piezoelectric cantilever sensor wherein the distal end 40 of the piezoelectric portion 14 is flush with the distal end 38 of the non-piezoelectric portion 16. The piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

FIG. 6 is an illustration of an example configuration 42 of an unanchored piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

Configurations of the piezoelectric cantilever sensor are not limited to the foregoing descriptions. Various other configurations are utilizable with the processes described herein. For example, various other configurations of the piezoelectric cantilever sensor utilizable with the herein described processes for detecting nucleic acids are detailed in U.S. patent application Ser. No. 11/747,183, entitled "SELF-EXCITING, SELF-SENSING PIEZOELECTRIC CANTILEVER SENSOR FOR DETECTION OF AIRBORNE ANALYTES DIRECTLY IN AIR," filed on May 10, 2007, which is hereby incorporated by reference in its entirety.

Nucleic Acid Detection Overview

Figure 7:
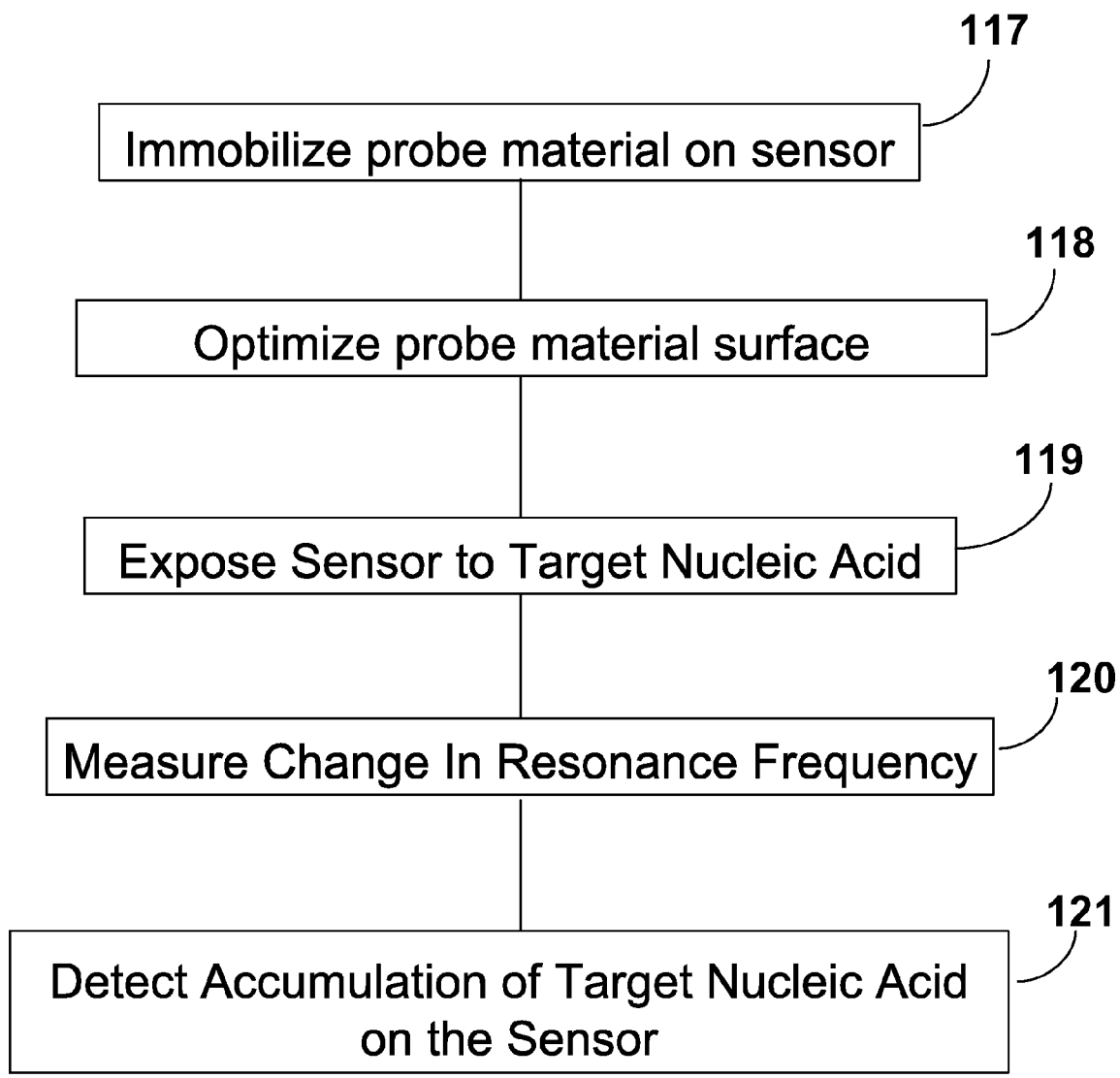
FIG. 7 is a flow diagram of an example process for detecting nucleic acids using a cantilever sensor.
Figure 8:
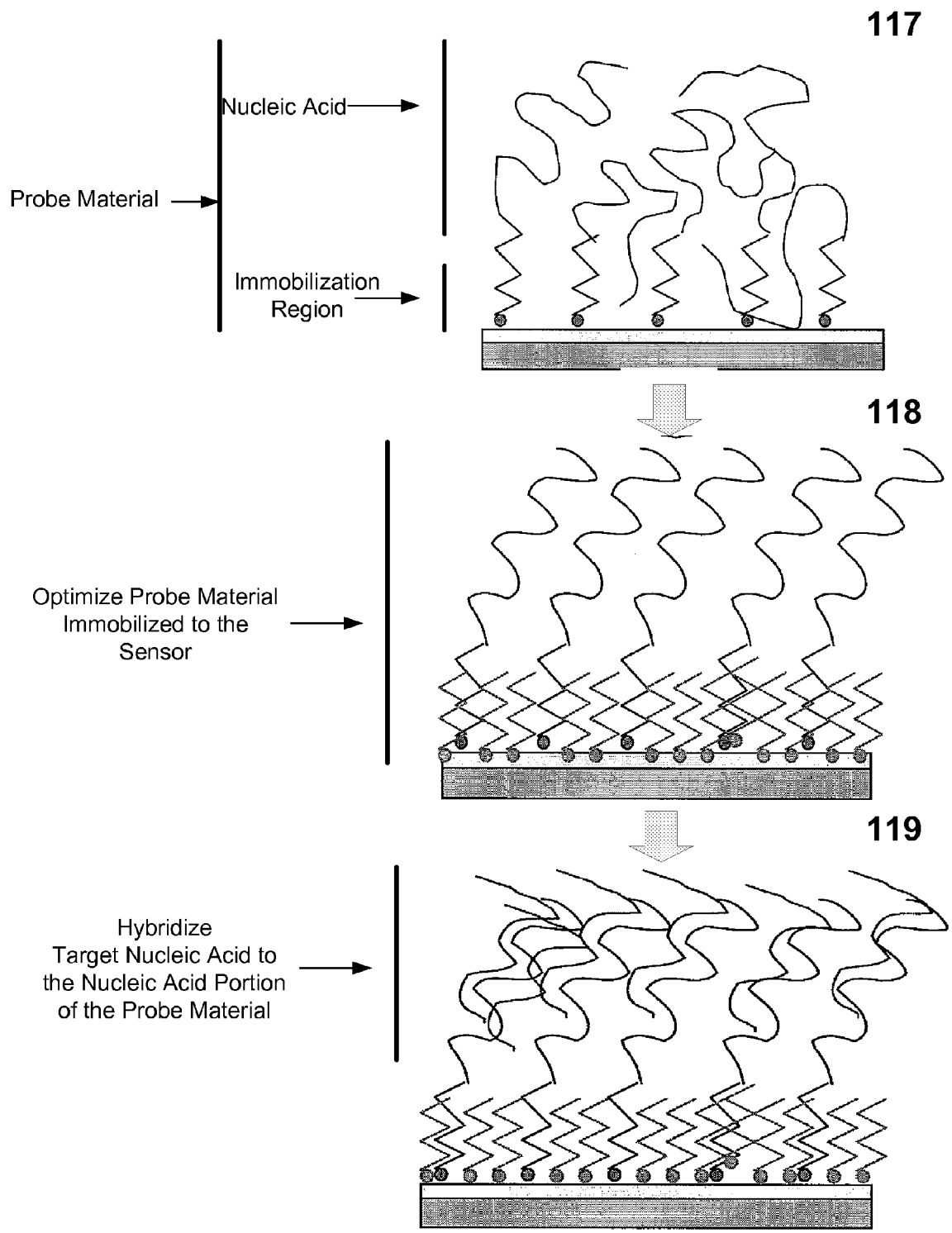
FIG. 8 is a illustration of the process of immobilizing probe material to the sensor, optimizing the sensor surface; and hybridizing target nucleic acid to the probe material on the sensor surface.

FIG. 7 is a flow diagram of an example process for using a self-excited piezoelectric cantilever sensor with nucleic acid binding. The sensor is first cleaned and dried whereupon the cantilever is ready for probe material immobilization. The probe material is generally composed of a nucleic acid of sequence that is complementary to the target nucleic acid that is to be detected and it can be ordered from a vendor. The probe material may be produced so that it has an immobilization region (such as a thiol groups) that can bind to the sensor surface. See FIG. 8. The probe material may also contain a linker region (such as C6) between the immobilization and nucleic acid regions of the probe material. Use of a linker renders the nucleic acid portion of the probe material more distant to the sensor surface, which may increase the probability of the nucleic acid portion of the probe material coming into contact with the target nucleic acid. The concentration of the probe material to be used depends upon the sensing area, the length of the probe and target sequences among other things. In some embodiments that 2 mL of 0.1-1 pM of probe material is suitable for a sensing area of 1.8-2.2 $mm^2$ for 15-25-mer oligonucleotide probe at 23-46° C. and at NaCl solution concentration of 50-1,000 mM. The density of probe material can directly affect hybridization efficiency. In some embodiments probe material density of $1.2 \times 10^{14}$ to $2.1 \times 10^{14}$ molecules/$cm^2$ is suitable.

At step 117, the non-piezoelectric portion of a piezoelectric cantilever sensor is treated to immobolize the probe material on the sensor. Utilization of a piezoelectric cantilever sensor permits detection of extremely small concentrations of nucleic acids that bind to the non-piezoelectric portion thereof. The self-excited piezoelectric cantilever is utilized to detect amounts of nucleic acid in a liquid medium, by placing probe material containing a specific nucleic acid region, containing complementarity to the target nucleic acid, on the sensor surface. The target nucleic acid binds to the complementary portion of the nucleic acid of the probe material, adding mass to the sensor surface. This added mass changes the resonance frequency to the self-excited piezoelectric cantilever sensor, allowing for the change in mass to be measured by the change in frequency.

At step 118, the sensor surface is optimized to facilitate binding of the target nucleic acid to the probe material using reducing agents, such as small thiol molecules, that can replace the weakly bonded probe strands to the sensing surface. The negatively charged backbone of the single stranded nucleic acid portion of the probe material renders many of these molecules bent and weakly adhered to the sensor surface thereby reducing the amount of probe material that may come into contact with the target nucleic acid. Reagents, such as 6-mercapto-1-hexanol (MCH) at 1 μM, fills the void left by the non-specifically adsorbed probe material molecules. The optimization may increase hybridization of target nucleic acid from 3-12%, but it can omitted if desired.

At step 119, the gas or liquid medium to be tested for the desired target nucleic acid is released into the chamber containing the sensor at a selected flow rate. If the desired target nucleic acid is present in the medium, the desired target nucleic acid binds (or hybridizes via the hydrogen bonding between complementary bases of the nucleic acids) to the probe material that was immobilized on the piezoelectric cantilever sensor. Skilled artisan would appreciate that the target nucleic acid can also be purified using known techniques. Hybridization is formation of sequence-specific base-paired duplexes from complementary single strands. Hybridization results from construction of hydrogen bonds between the complementary base pairs, A=T and G≡C; where bases A, T, G, and C stand for Adenine, Thymine, Guanine, and Cytosine. Double stranded nucleic acids can denatured using known methods, such as heat or heating and chemicals (e.g., urea and NaOH). It is understood that nucleic acids may hybridize to one another even in the presence of a base pair mismatch (noncomplementarity) as described further.

At step 120, the resonance frequency of the sensor is measured as the target nucleic acid hybridizes to the probe material on the sensor's surface. As the target nucleic acid hybridizes to the probe material, the mass of the sensor begins to increase, resulting in a change of the resonance frequency. The resonance frequency is continued to be measured until it stabilizes, at step 121.

Figure 9:
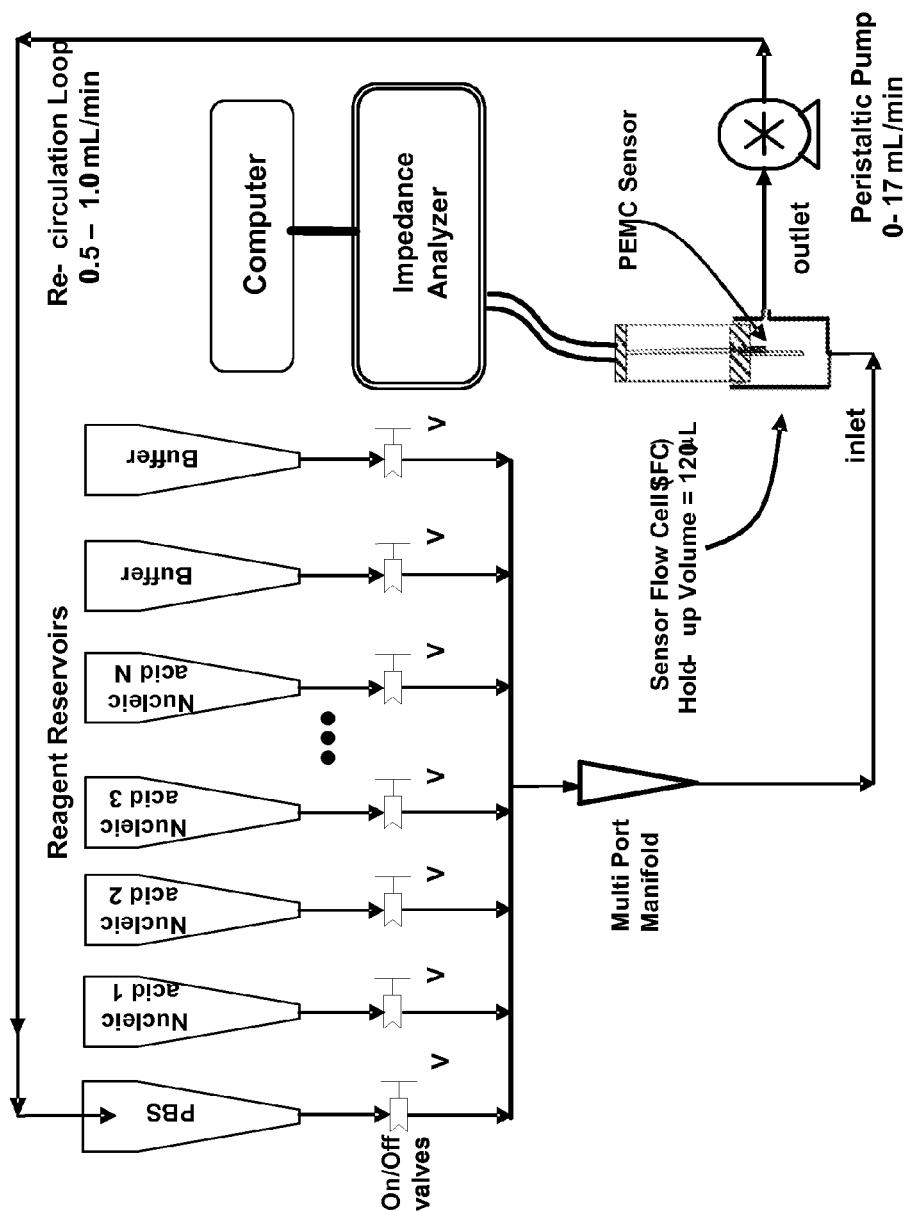
FIG. 9 is a schematic of experimental apparatus utilizing a piezoelectric cantilever sensor.

A schematic of the experimental setup is given in FIG. 9. The experimental setup included various fluid reservoirs, a peristaltic pump, and a sensor flow cell (SFC). Although a system having five reservoirs was used, FIG. 9 depicts multiple reservoirs for multiple target nucleic acids, from nucleic acid 1 to nucleic acid N, wherein N is an appropriate integer. A reagent reservoir manifold containing five chambers was connected via a five port manifold to the inlet of the SFC. A peristaltic pump was connected to the outlet of the SFC and was used to maintain the flow rate between 0.5 and 1.0 ml/min. The PEMC sensor was inserted into the SFC and the electrodes were connected to an impedance analyzer interfaced with a computer to obtain impedance and phase angle measurements in the frequency range of 10 kHz and 1.8 MHz. The experimental apparatus allowed for a single pass through the SFC as well as recirculation of reagent during probe immobilization. The sensor flow cell (SFC) had a well diameter of 7.0 mm with a hold-up volume of 120 μL after the sensor was installed. The inlet and outlets were located at the bottom and on the side of the cell, respectively, approximately 4 mm apart. The liquid reservoirs were connected to the inlet of the SFC via a five-entrance port manifold with a single outlet. The outlet of the flow cell was connected to a peristaltic pump, which controlled the flow of the desired fluid into and out of the SFC.

The functionalized sensor was installed vertically into the SFC filled with PBS. The cantilever electrodes were connected to an impedance analyzer interfaced to a PC comprising an application for recording impedance and phase angle measurements in the frequency range of 40 kHz to 1.5 MHz. Resonant frequency values were recorded every 30 seconds and the mean value was calculated over a 2.5 minute period. The SFC was maintained at 30±0.1° C. by circulating (17 mL/min) constant temperature water 38±0.1° C. through a jacket surrounding the SFC. Valves located at the bottom of each of the fluid reservoirs enabled the selection of the fluid for flow into the SFC or for circulation. Switching the outlet line from the peristaltic pump into the desired fluid reservoir enabled total recirculation, when needed.

The sensors used in the experiments were used directly after gold coating the glass surface of the sensor. The sensor was installed in the sample flow cell and stabilized with buffer for 10 minutes. The gold sensor surface was exposed to probe material, and in some cases followed by optimization with reducing agents, and then exposure to target nucleic acid. After each detection experiment, the sensor surface was cleaned and re-used. After three such re-uses, it was recoated.

The detection experiments were carried at flow rates of 0.5-1.0 mL/min. Buffer solution was re-circulated through the SFC to ensure the tubing and SFC was flushed prior to a detection experiment. The measured resonant frequency of the cantilever sensor was monitored until it stabilized before probe immobilization and subsequent target nucleic acid detection. After stabilizing the sensor in buffer, the probe material would be immobilized on the sensor followed by exposure to target nucleic acid. Detection was initiated by flowing the sample past the sensor surface at 0.5-1.0 mL/min in recirculation mode until steady state was reached. Steady state was assumed to have been reached if the sensor resonance frequency was within ±30 Hz for a minimum of 10 minutes. Since the total volume in the flow circuit was approximately 3 mL, a ten minute time course would allow 3-4 fluid exchanges, which is sufficient to ensure the previous solution has been cleared from the circuit. After this, the flow circuit was rinsed with buffer followed by the release buffer to release the bound antigen. Finally, a buffer flush was carried out until the resonant frequency value reached steady state to remove weakly attached and suspended particles.

Figure 10:
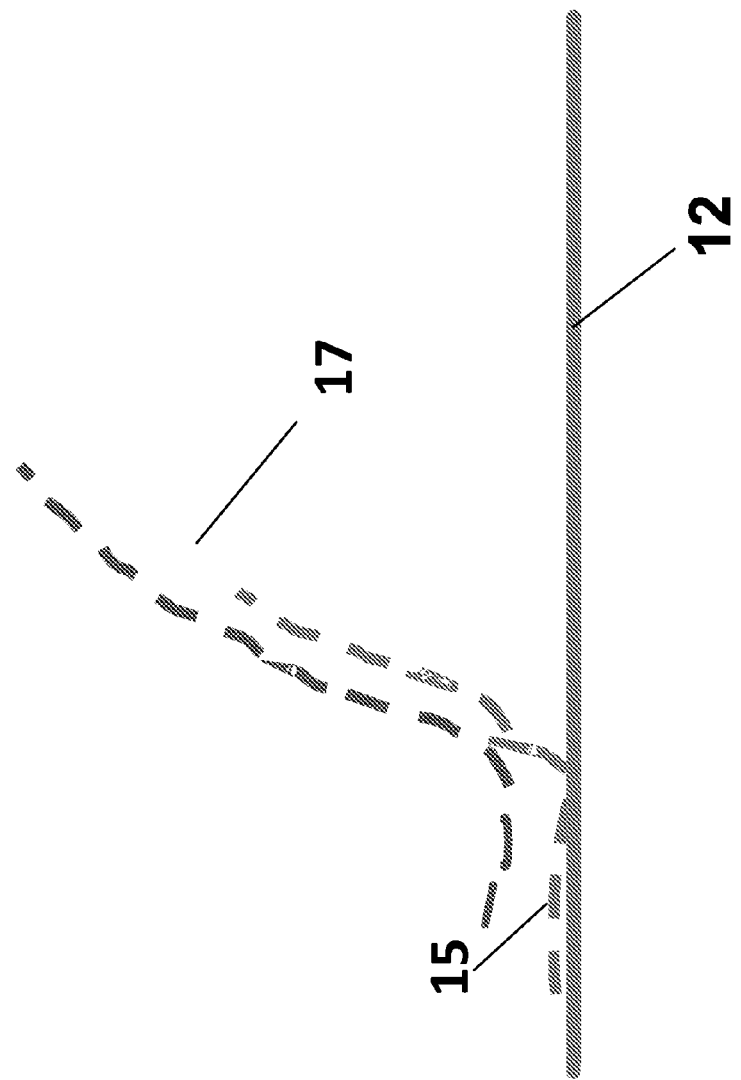
FIG. 10 is an example diagram illustrating the interaction of target nucleic acid with the nucleic acid portion of probe material.

FIG. 10 is a diagram illustrating the interaction of target nucleic acid with probe material. The probe material 15 comprises a nucleic acid strand immobilized on the sensor surface 12. The target nucleic aid 17 comprises a complementary strand of nucleic acid bound (or hybridized) to the nucleic acid portion of the probe material 15.

Applications to Detect Specific Target Nucleic Acids in Various Preparations

Detection of the APP Gene

Figure 11:
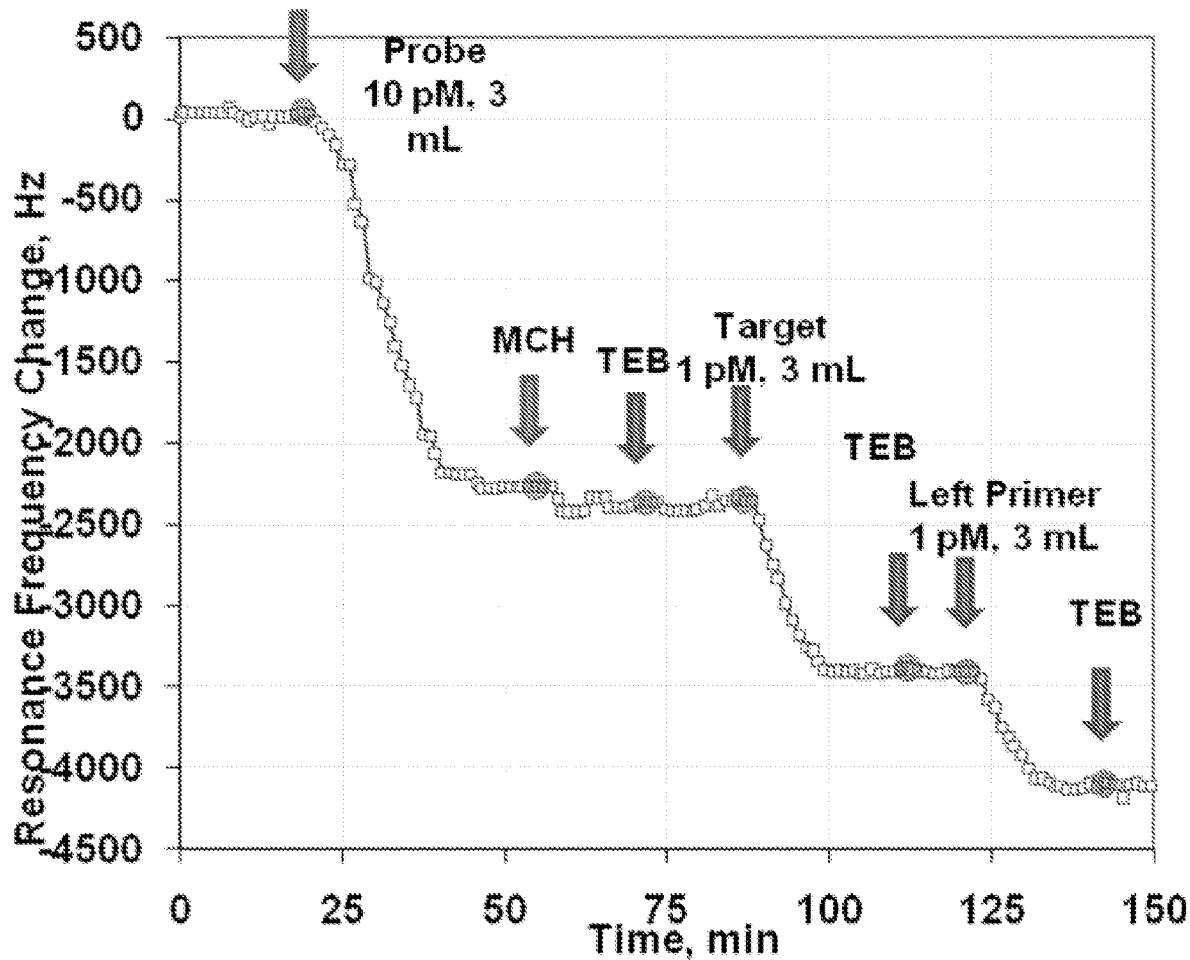
FIG. 11 is a plot illustrating example results of the detection of DNA via hybridization of unlabeled DNA.

FIG. 11 is a plot illustrating the addition of mass to a cantilever sensor by hybridizing unlabeled single stranded DNA ("ssDNA") to complementary strands that extend from the sensor surface. A gold-coated cantilever sensor (Resonance Frequency 826 kHz) was immobilized with a thiolated single strand DNA (ssDNA) with an 18-mer sequence HS-$(CH_2)_{6-5}$'CTC CAGGG CCAGG CGGCG3' (SEQ ID NO:1) by introducing at t=20 min (labeled A) and circulated in the flow apparatus prepared in TRIS-EDTA buffer+50 mM NaCL at 10 pM and 3 mL sample. The immobilization caused a shift down of nearly 2200 Hz in resonance frequency. After reaching equilibrium, 1.5 mL 1 μM mercaptohexanol (labeled B) was circulated to orient the immobilized ssDNA and a small resonance shift down is noted. Subsequently, 2 mL of 1 pM solution of freshly denatured 288-mer section of the amyloid β precursor protein gene ("APP gene")

(SEQ ID NO: 2)
(5' CATTTCCAGGAGAAAGTGGAATCTTTGGAACAGGAAGCAGCCAACG

AGAGACAGCAGCTGGTGGAGACACACATGGCCAGAGTGGAAGCCATGCTC

AATGACCGCCGCCGCCTGGCCCTGGAGAACTACATCACCGCTCTGCAGGC

TGTTCCTCCTCGGCCTCGTCACGTGTTCAATATGCTAAAGAAGTATGTCC

-continued

GGCGCAGAACAGAAGGACAGACAGCACACCCTAAAGCATTTCGAGCATGT

GCCGCATGGTGGATCCCAAGAAAGCCGCTCAGATCCGGTCCCAG 3')

was circulated (labeled C) which immediately hybridized causing a shift down of 1055 Hz. After reaching steady state, the hybridization was confirmed by introducing and circulating (labeled D) 3 mL of 1 pM of 20-mer strand complementary to APP gene that hybridizes to position 54 to 74 (in bold and double underlined above) in APP gene. Position count is from 5' to 3' position. Note that the probe hybridized to position indicated in bold and underlined above. The response 698 Hz is because of addition of mass due to hybridization in position 54 to 74. Note in the above experiment the probe immobilized on the sensor hybridizes between position 105 and 124 on APP gene. The ratio of second hybridization to the first one is =698/1055=0.66.

Detection of Synthetic Oligonucleotides

Single-stranded thiolated 15-mer oligonucleotide probe from Bacillus 16s-rRNA sequence HS-$C_6H_{12}$-5'-GGAA-GAAGCTTGCTT-3' (SEQ ID NO:3), the complementary 10-mer target 5'-AAGCAAGCTT-3' (SEQ ID NO:4) and a stock 10-mer target of random and unknown sequence were purchased from Integrated DNA Technologies (Coralville, Iowa). The lyophilized DNA samples were reconstituted to a stock concentration of 65.8 µM in Tris-EDTA (TE) buffer (10 mM Tris-HCl, 1 mM EDTA, pH 8.0) containing 1 M NaCl. It was diluted in TE buffer to desired concentration prior to use. 1 M NaCl was used to bring the hybridization temperature of probe-target DNA strands to desired temperature of operation (32° C.), which is 5° C. lower than the melting temperature 37° C. In addition, presence of NaCl in the buffer reduces the anionic electrostatic repulsion between the probe and target oligonucleotides and increases stability of duplexes. 1-mercapto-6-hexanol (MCH) at 1 µM was freshly prepared in TE buffer for each experiment. Pooled normal human plasma (IPLA-2) was purchased from Innovative Research (Southfield, Mich.) and was used as a sample complex matrix.

Thiolated single stranded DNA (ssDNA) probe was supplied in disulfide form and was reduced prior to use. To each aliquot containing 250 µL of 65.8 µM thiolated probe, 3.9 mg of dithiothreitol (DTT) powder was added and reacted at room temperature for 30 minutes. Excess DTT was removed with SephadexB G-25 columns (Pure Biotech LLC, NJ) following the vendor supplied protocol. The effluent, free of DTT, was diluted in TE buffer to desired concentration (1 aM to 100 nM) and used within 1 hour. No attempts were made to optimize probe surface concentration. However, concentrations used in this report are 1 pM, 49 pM, 500 pM and 50 nM.

The sensor was firmly secured in a temperature controlled sensor flow cell (SFC) maintained at 32.1±0.1° C. The PEMC sensor was connected to an impedance analyzer (HP 4192A or HP 4294A) interfaced to a PC running a custom written LabVIEW™ data acquisition program. Impedance, capacitance and phase angle values of the sensor were collected at 10 to 30 s interval in the frequency range of interest. A typical experiment was started by first flowing TE buffer through the SFC until a baseline resonance frequency was established (~5-20 min). Flow rate was kept at a constant value of 0.6 mL/min in all experiments. At 0.6 mL/min, the average bulk velocity in SFC is 0.06 cm/s. Once a stable baseline was established, 1 pM probe solution was flowed through SFC. Upon reaching a stable resonance frequency due to chemisorption of the thiolated probe on the sensor surface, a freshly prepared 1 µM MCH in TE buffer was pumped through the flow cell to fill unoccupied Au <111> sites and to remove any non-specifically attached probe strands from the sensor surface. Immediately thereafter sample solution containing the target ssDNA was flowed in the sequence of buffer, complementary strand and finally TE buffer again. The test sample solutions were circulated for 30-45 minutes until resonance frequency of the sensor reached a constant value. When the same sensor was re-used it was first cleaned in piranha solution (7:3 volume ratio of concentrated $H_2SO_4$ and 30% $H_2O_2$) for 2 minutes, rinsed with copious amount of DI water and ethanol, and finally oven dried at 110° C. Cleaning the sensor reduced the surface area for probe attachment by 8-10% after the fourth cleaning. Where multiple sensors were used, the mass change sensitivity was comparable across the sensors.

Each experiment was repeated at least three times. Although the experiments were conducted using three different sensors, their mass change sensitivity was within 30% of 0.3±0.1 fg/Hz at the mode present near 1 MHz, as measured by known mass addition method. The resonance spectrum of each sensor was examined in air and liquid to determine the most sensitive mode with a suitable Q-value, and is summarized in Table 1 for the three sensors used.

TABLE 1

| Mode | Resonance frequency in air [kHz] | Q factor in air | Resonance frequency in Liquid [kHz] | Q factor in Liquid |
|---|---|---|---|---|
| PEMC - A Low order | 49.525 ± 0.008 | 33 ± 1 | 10.125 ± 0.016 | 30 ± 1 |
| PEMC - A Medium order | 146.500 ± 0.011 | 18 ± 1 | 139.525 ± 0.018 | 15 ± 1 |
| PEMC - A High order | 1007.125 ± 0.012 | 23 ± 1 | 939.250 ± 0.020 | 19 ± 1 |
| PEMC-B High order | 919.725 ± 0.011 | 24 ± 1 | 862.32 ± 0.020 | 19 ± 1 |
| PEMC-C High order | 968.340 ± 0.013 | 22 ± 1 | 899.520 ± 0.018 | 18 ± 1 |

The Q-value is a measure of sharpness of the peak and is defined as the ratio of resonance frequency divided by frequency width at half the peak height. In air PEMC-A exhibited three main resonance modes at 49.52 kHz, 146.500 kHz and 1007.125 kHz. When it was in a flowing TE buffer, the resonance frequencies decreased to 10.125 kHz, 139.525 kHz and 939.250 kHz, respectively. Since the highest mode decreased by 67.875 kHz compared to 39.400 and 6.975 kHz for the first two modes, the peak at 1007.125 kHz was deemed the most sensitive and used for detection. The Q-value in air was 23±1 and in liquid, it decreased to 19±1. Although there was a 17% decrease in Q value, the resonance frequency value can be measured effectively with an accuracy of ±4 Hz in air.

PEMC-B and PEMC-C exhibited high-order resonance at 921.21 and 953.43 kHz and were 10% less sensitive than PEMC-A. Their peak shape factor was reasonably high for detection purpose.

Figure 12:
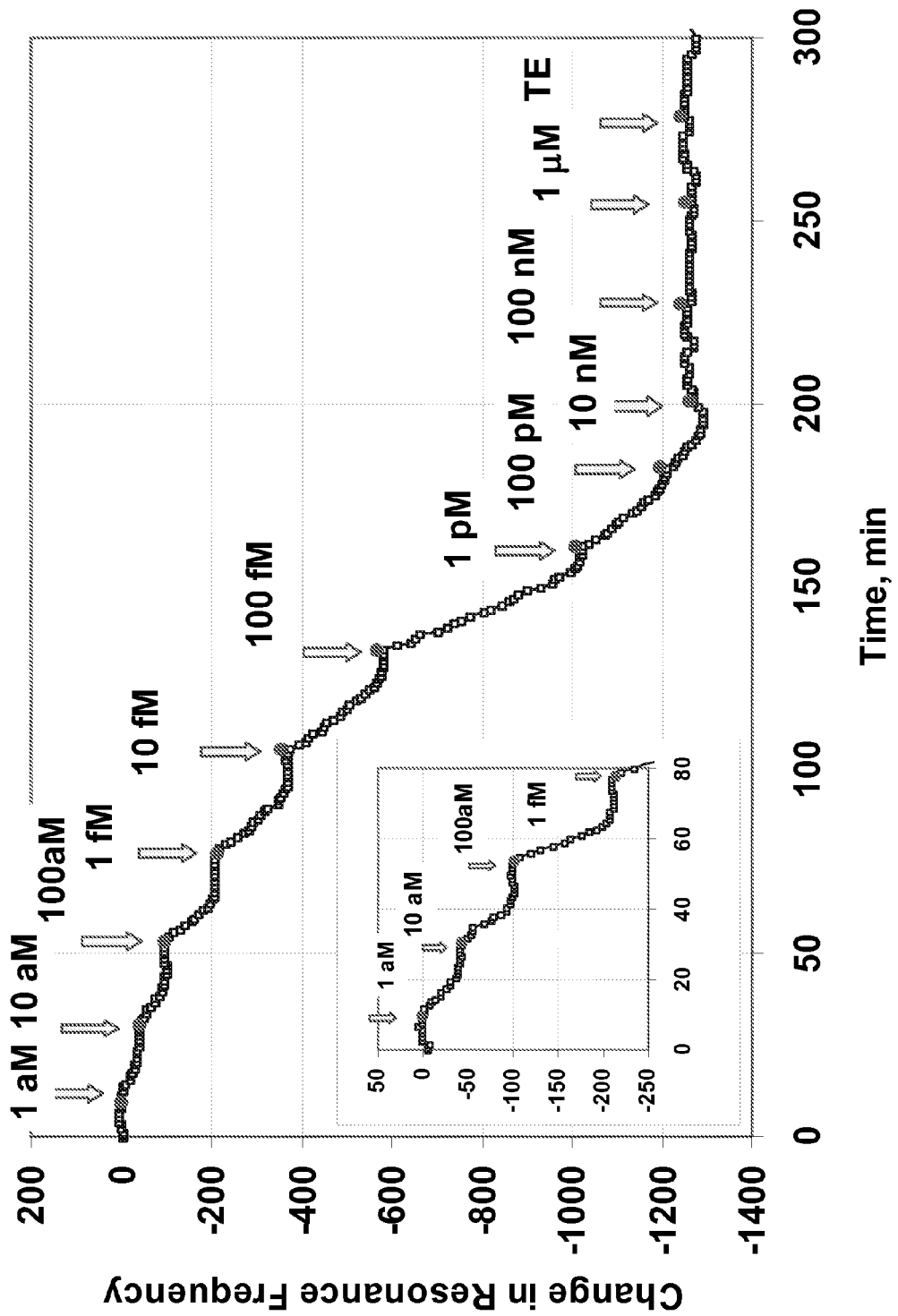
FIG. 12 is a plot illustrating example results of the detection of increasing concentrations of DNA via hybridization of unlabeled DNA.
Figure 13:
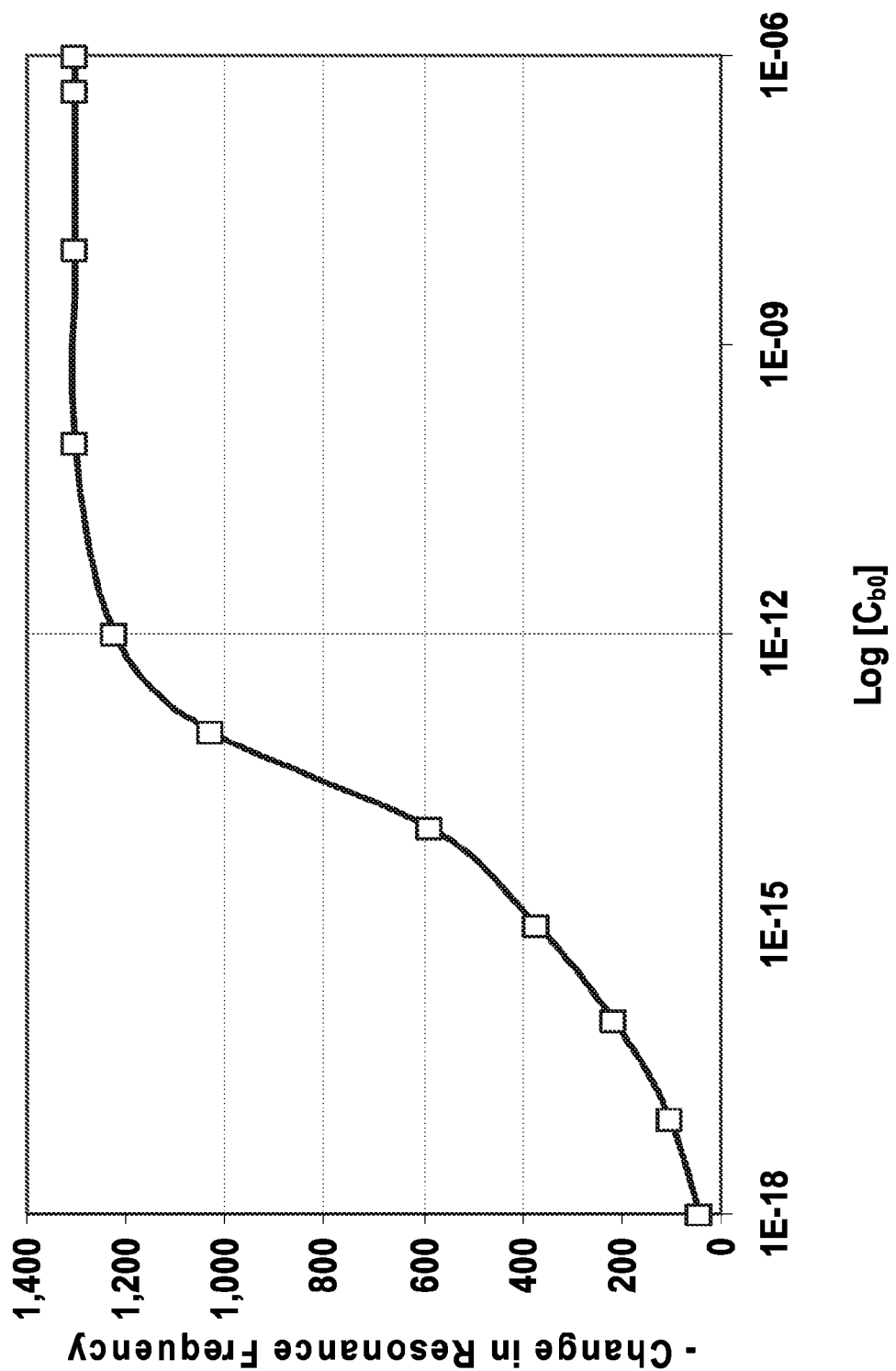
FIG. 13 is a plot illustrating the logarithmic response of various concentrations of probe material immobilized on the sensor surface.

PEMC sensor A, with Au-coated area of 1.8 mm$^2$ was secured to the flow cell, and was stabilized at 0.6 mL/min TE buffer at 32.2±0.1° C. Subsequently, reservoir containing 10 mL of 1 aM probe was pumped through SFC. The first 5 mL of the fluid was sent to waste, and the last 5 mL was put in recirculation mode. The PEMC sensor responded, as shown in FIG. 12, with decrease in resonance frequency as the probe's thiol group became attached to sensor surface. After a transient period of ~13 minutes the sensor reached steady state with a total resonance frequency change of 42 Hz. The inset in FIG. 12 shows that the noise level is ~2 Hz. At 30 min, the sample containing 10 aM was flowed in initially in a once through mode (for 5 mL) to remove previous probe solution, followed by recirculation. Resonance frequency decreased by an additional 47 Hz. The process was repeated in steps of 10× in concentration until there was no measurable change in resonance frequency. Increase of inlet concentration to 10 nM and then to 1 µM lead to no further change in resonance frequency indicating that no further probe immobilization took place. The changes in resonance frequency can be plotted as a function of inlet probe concentration and the resulting curve (FIG. 13) indicates that equilibrium exists between surface and liquid concentrations. The 10 mL of 1 aM contains a total of 6,000 molecules or 51 ag. The mass change sensitivity is ~1 ag/Hz. The sensor is 1.8 mm$^2$ and has 1.1× 10$^{13}$ Au<111> sites, and can accommodate a maximum of ~3.2×10$^{11}$ ssDNA. That is chemisorption of 6,000 strands is a fractional coverage on the order of 10$^{11}$. Note that ssDNA occupies a cross sectional area of 3.14 nm$^2$, and the values calculated are based on maximum packing density. Subsequent increase in concentration by a factor of 10 caused a decrease in resonance frequency by a factor of 2 suggesting a logarithmic sensor response. The calibration was done with the addition of 1 to 5 fg to the sensor surface. FIG. 13 shows that 1 fM gave a sensor response of ~370 Hz for a total probe exposure of 51 fg. If all the entering probe molecules attached to the surface, one would estimate the sensitivity as ~7 fg/Hz, and is the lowest possible mass change sensitivity value. Ten ML of 1 aM sample contains ~104 strands. Since the sensor contains ~10$^{12}$<111> sites, we expect a substantial number of sites on the sensor is vacant when steady state response is reached. At the final step of 10 mL of 10 nM, the number of probe strands introduced is 6×10$^{12}$. It is interesting to note that this is within an order of magnitude of number of Au <111> sites on the sensor. Since we assumed the entire inlet probe DNA chemisorbed, the sensitivity figure would be the least possible value. To the first approximation it appears that not all of the probe strands in the feed attaches to the sensor surface even though substantial sensor surface is "empty". A similar result was observed with thiol compounds. In any case, it is reasonable to conclude that both mass addition method and probe chemisorption approach indicates that PEMC sensors exhibit sensitivity of subfemtogram/Hz.

Figure 14:
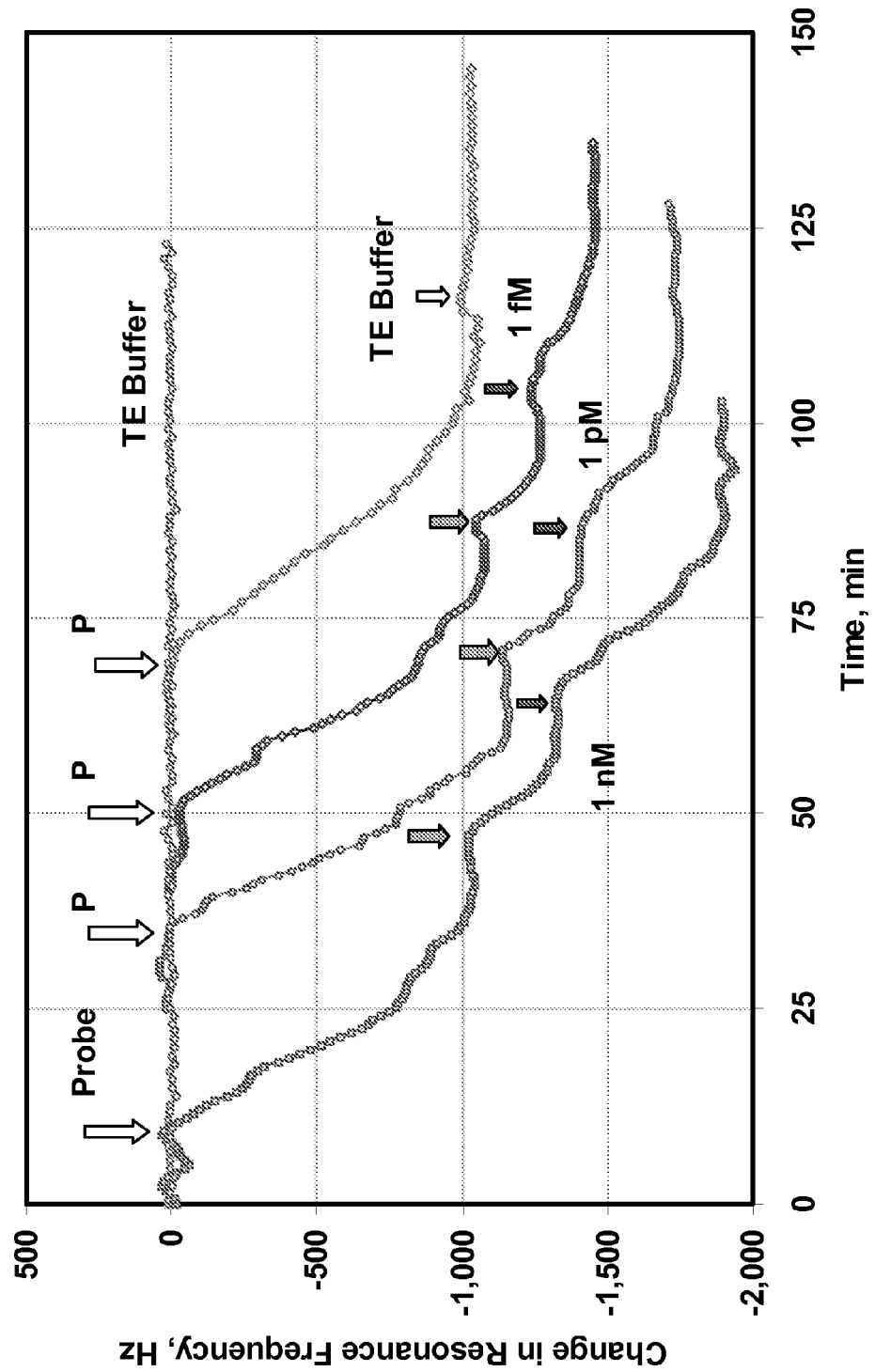
FIG. 14 is a plot illustrating example results of the detection of various concentrations of target nucleic acid binding to various concentrations of probe material.
Figure 15:
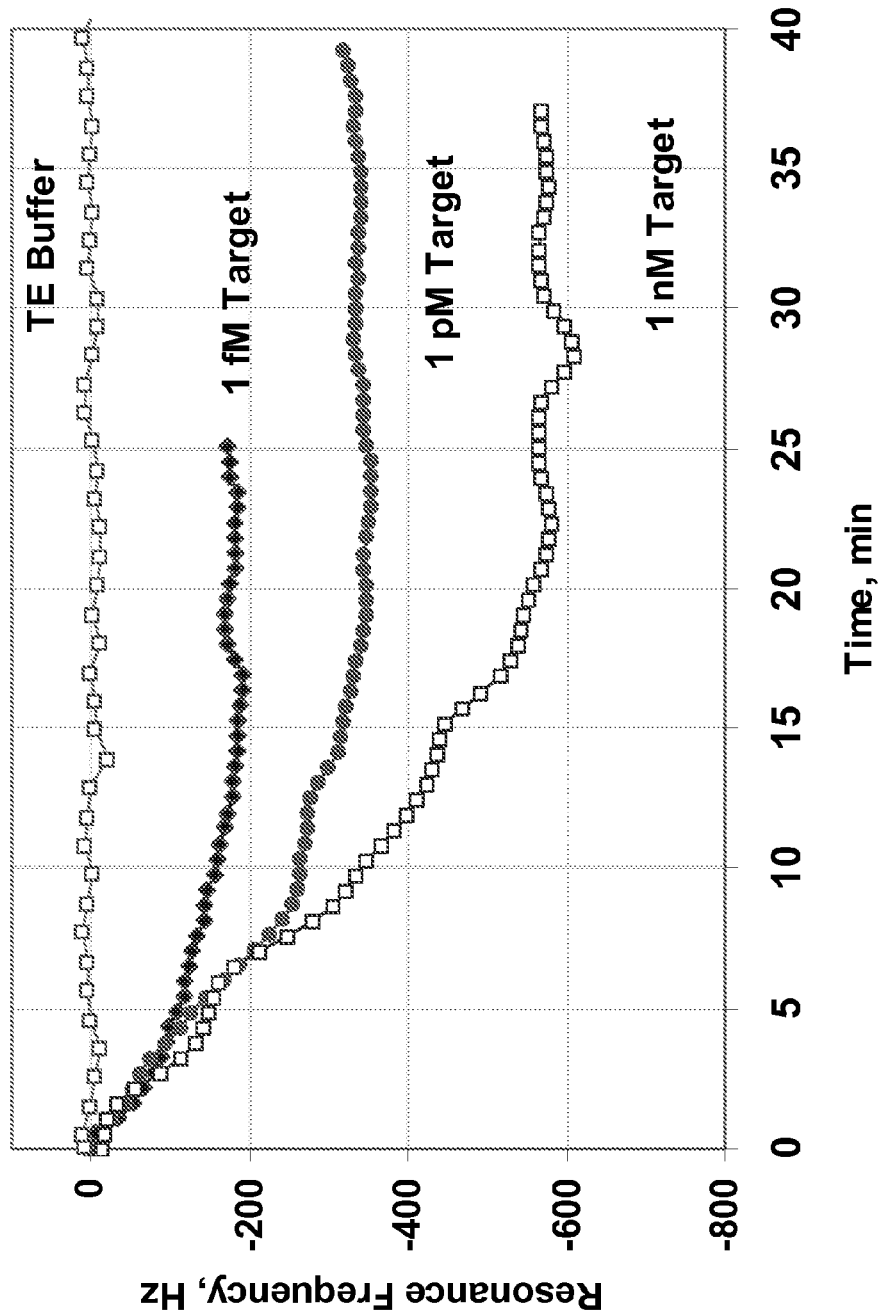
FIG. 15 is a plot illustrating example results of the detection of various concentrations of target nucleic acid at constant temperature.

The response to hybridization of complementary strand at three concentrations of 1 fM, 1 pM and 1 nM is shown in FIGS. 14 and 15. After stabilizing the sensor in TE buffer thiolated probe (9 mL) in TE buffer at 1 pM was initiated in a recirculation mode, after an initial 5 mL flush. As soon as the probe solution entered the SFC, the resonance frequency decreased exponentially and reached steady state in ~27 minutes with a total decrease of 1,037±21 Hz (±Standard Deviation (SD) over 10 minutes). Subsequently 10 mL of 1 µM MCH was flowed through the sensor in a once-through mode which lasted 15 minutes during which there was a further decrease of ~305 Hz. The smaller MCH molecules compete with the probe bases weakly adhered to the sensor surface while keeping the covalently bonded thiolated probe molecules intact. The MCH treatment also helps to extend the DNA strands away from the sensor surface and into the solution, thereby, increasing the probability of coming into contact with the target strands. Additionally, the smaller MCH molecules scattered in between the larger probe DNA strands enhance the accessibility of the probe strands to the target thereby improving the final hybridization efficiency. Once the MCH treatment was complete, 30 mL of 1 fM of 10-mer complementary strand was introduced in an one-through mode without recirculation. As soon as the sample entered the chamber, there was a slow decrease in resonance frequency and reached steady state in ~17 min. After ~25 minutes of target flow and a change of ~190±19 Hz the sensor resonance frequency reached steady state. The sensor was removed and cleaned according to the protocol described earlier and the sequence of probe attachment and subsequent hybridization with target strand was repeated at 1 pM and 1 nM. The complementary strand at 1 pM elicited a 345±14 Hz decrease in 19 minutes while 1 nM caused a 540±39 Hz decrease. FIG. 14 shows the entire response from sensor stabilization in buffer, probe attachment, probe surface optimization with MCH to hybridization with target strands. The three probe immobilization steps shown in FIG. 14 gave responses of −1,140; −1,068; and −1,038 Hz and are within 9% of each other, and is quite reproducible on the same sensor. In each case nearly the same number of probes were on the surface, and a million-fold change in target concentration resulted in a three-fold hybridization response (FIG. 15).

Since the 1 nM sample reached steady state in 25 minutes, ~15 picomoles of target was exposed to the sensor surface. Response to MCH was a change of 295 Hz. Given that mass ratio of MCH to the probe is (=134/5,070) the response to MCH would suggest that ~8.5% of the sensor surface was occupied by the probe. Since 1.8 mm$^2$ of sensor surface area has 1.1×10$^{11}$ Au1<111> sites the 9 femtomoles (9 mL, 1 pM) of probe introduced would be leave many vacant sites, and is consistent qualitatively with the observed shift with MCH. Ratio of molecular mass of target to that of probe is =3300/5,070=0.65. The response ratio of hybridization to the probe response is 540/1038=0.52, which suggests 80% hybridization, if we assume that all immobilized probes are accessible for hybridization and the sensor response is linear.

Figure 16:
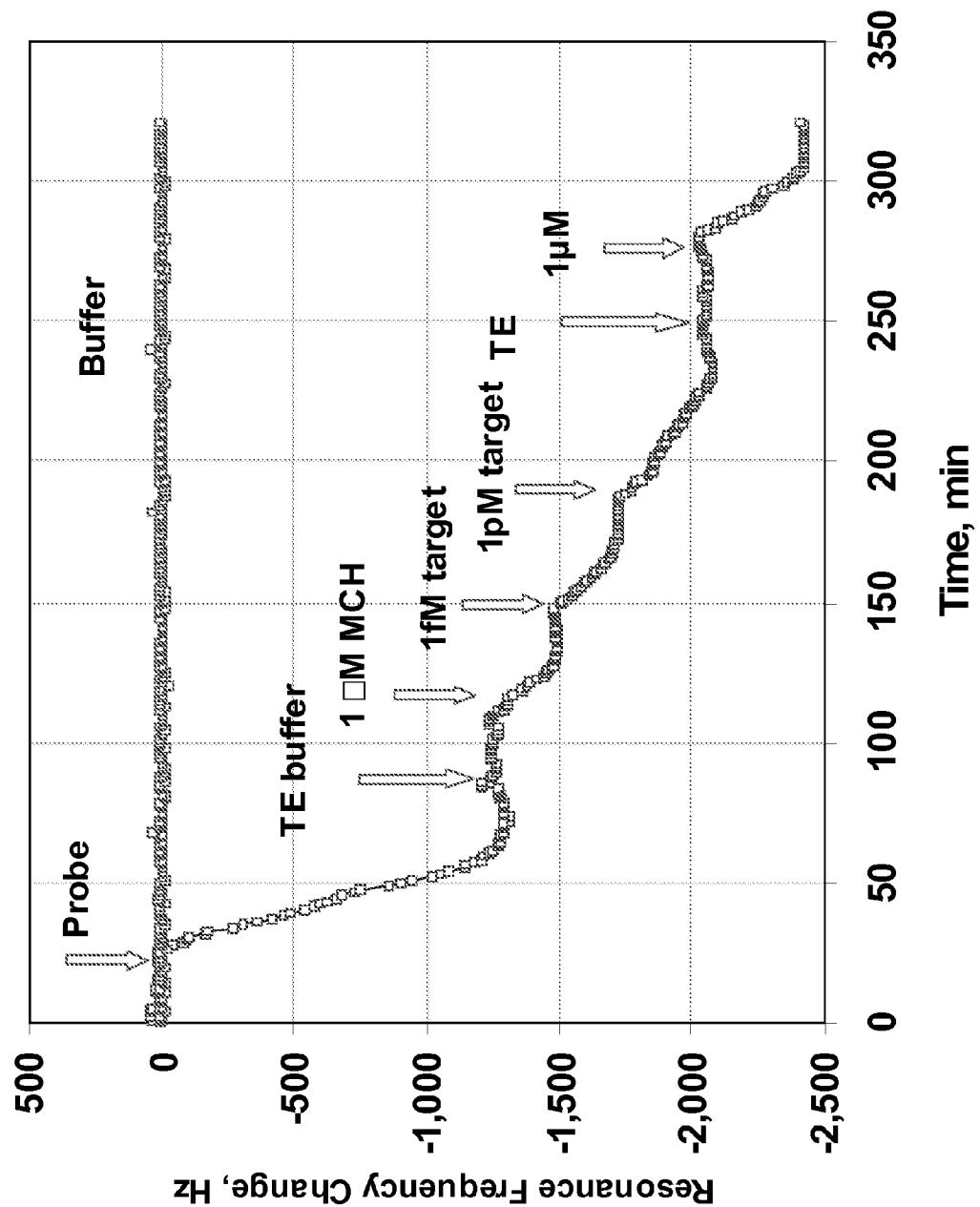
FIG. 16 is a plot illustrating example results of the detection of various concentration of target nucleic acid.
Figure 17:
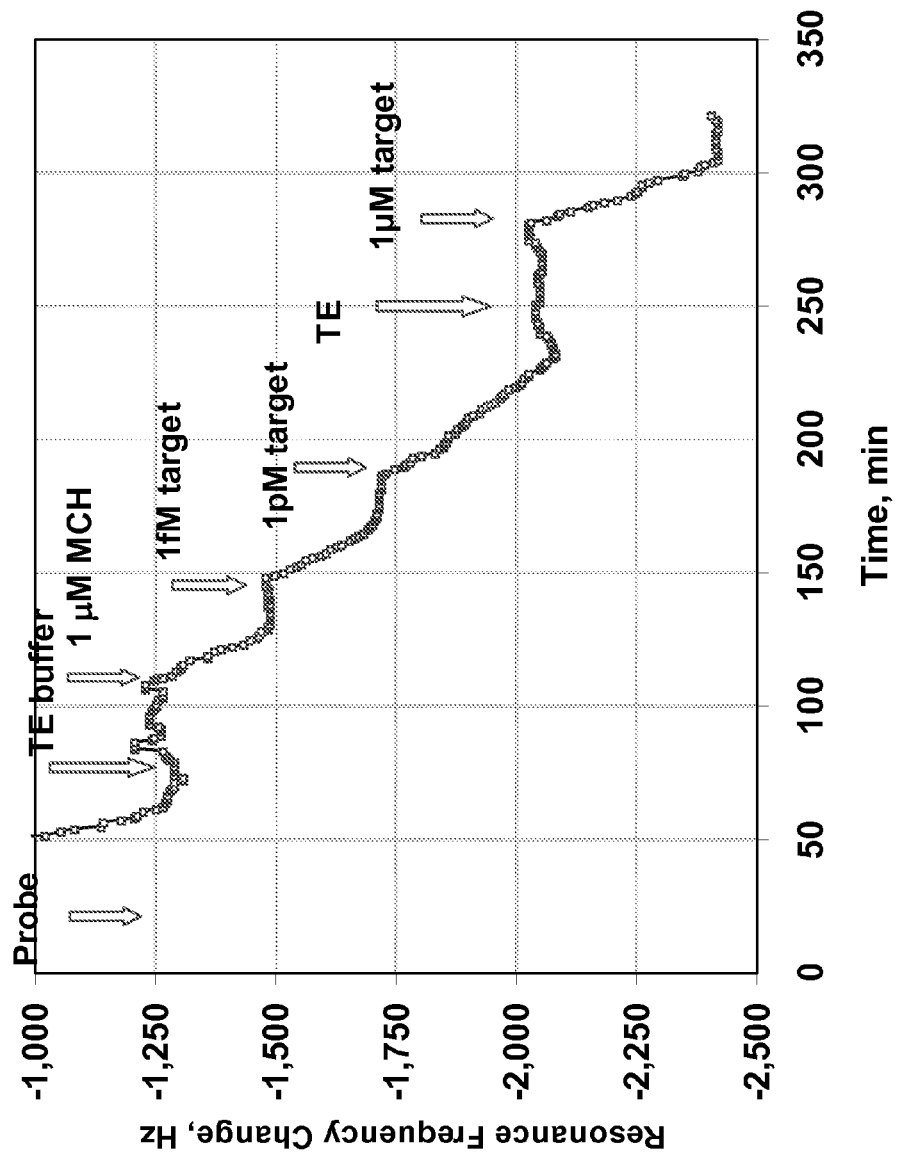
FIG. 17 is a plot illustrating example results of the detection of various concentration of target nucleic acid.

To determine response of immobilized probe to sequential addition of increasing concentrations of complementary target DNA was performed. A PEMC sensor (PEMC-B; 921.12 kHz in air and 862.32 kHz in liquid) with surface area of 1.8 mm$^2$ was immobilized with 10 mL probe of 49 pM and gave a response of 1,290±33 Hz (FIGS. 16 and 17). After a TE buffer flush, 1 µM MCH was flowed in until steady state resonance frequency was reached. This resulted in a 240±13 Hz decrease. Then sequential injection of 1 fM, 1 pM, and 1 µM complementary single stranded DNA containing samples were flowed in. For each of step, 2 mL of sample was loaded into a clean reservoir, and was pumped into the flow circuit in a once through mode. As the content in the reservoir reached close to empty the outlet of the flow cell was returned to the reservoir so that the sample was in a recirculation mode. Since the flow loop volume is 2.2 mL, the circulating sample concentration was diluted by ~10% and the previous sample concentration was diluted by ~90%. The response to 1 fM took ~20 minutes to reach steady state and resulted in a frequency decrease of 258+11 Hz. Subsequent responses to 1 pM and 1 µM caused a further decrease of 320+13 Hz and 390+18 Hz, respectively. A TE buffer flush at 250 minutes resulted in essentially no change in resonance frequency suggesting weakly bound strands, if any, was few or none. The cumulative response to the three target additions was ~931 Hz and is 75% of the probe response (−1,245 Hz). Since target to probe mass ratio is 0.65, we note that hybridization response is higher than expected, if linear response is assumed. This was not the case when probe immobilization was done with 1 pM. If 931 Hz response is taken as complete hybridization, the response to 1 fM and 1 pM may be estimated as 27% and 62%, respectively.

Figure 18:
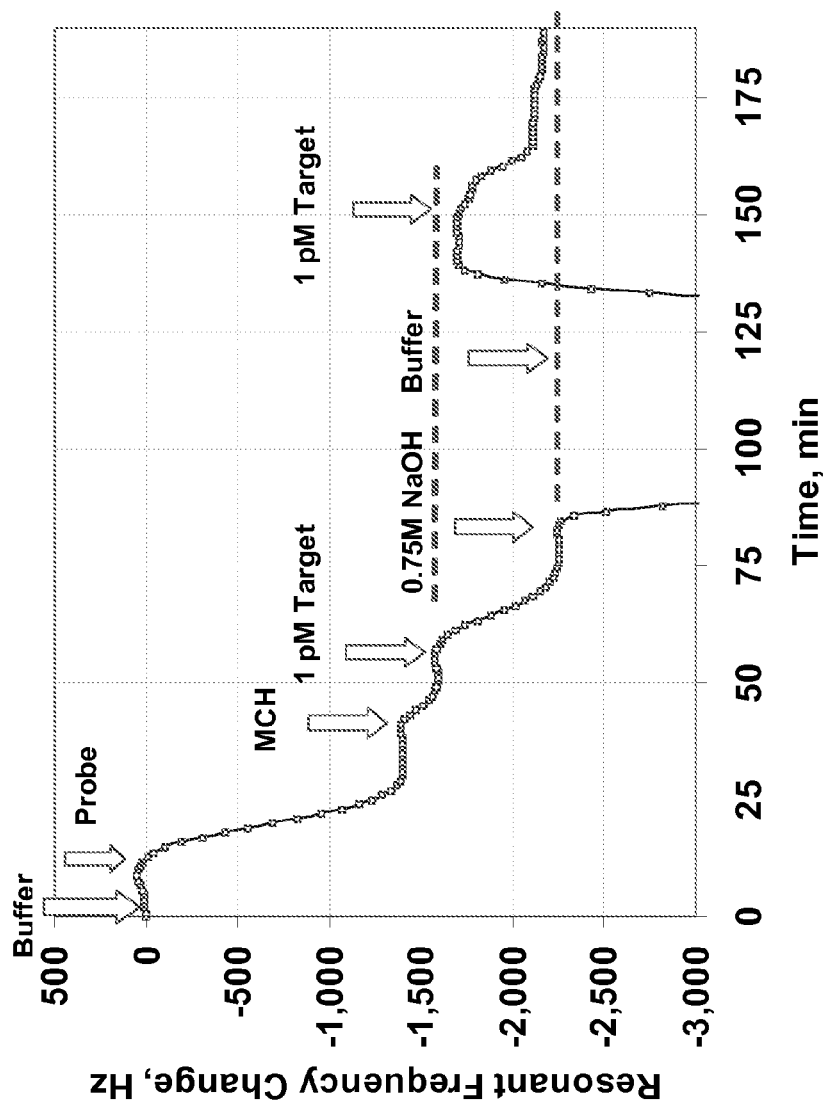
FIG. 18 is a plot illustrating example results of the sequential detection of hybridization, dehybridization (denaturing), and hybridization of target nucleic acid to the probe material on the sensor surface.

Double stranded DNA can be de-hybridized using strong alkali solutions such as urea or NaOH. If hybridized DNA strand is selectively removed without destroying the probe surface, the regenerated surface can be used for further detection. For the set of probe and target oligonucleotides used in this study, dehybridization using various concentrations of NaOH were explored (n=4), and 0.75 M NaOH showed the most promise and was used in further experiments. After immobilizing 2 mL of 1 pM probe, it was treated with 2 mL of 1 μM of MCH. In FIG. 18 response to the entire experimental sequence is shown. At 58 min, 2 mL of 1 pM complementary ssDNA was flowed in and hybridization (−667±23 Hz) was observed. To de-hybridize the target DNA, 0.75M NaOH solution was then introduced which caused an immediate and rapid change in frequency of −8,115±154 Hz. Density of 0.5M NaOH is 1.032 g/mL whereas the density of TE buffer with 1M NaCl is estimated as 1.038 g/mL. Since the density difference is small, the rapid decrease in resonance frequency is thought to be due to temperature increase as a result of release of heat of dilution. At 111 min, the flow was switched to TE buffer to remove NaOH and the resonance frequency recovered and stabilized at 102±14 Hz below the value that was present at the beginning of hybridization. Since hybridization resulted in −677±23 Hz, we estimate 85% of the decrease was recovered due to dehybridization. To the first approximation, this may be interpreted as 85% dehybridization. The flow was then switched to a freshly prepared batch of 2 mL of 1 pM complementary ssDNA which caused a decrease of 415±39 Hz for the second hybridization with the same surface probe. The 38% reduction in sensor response the second time around suggests that the probe surface may not have been fully regenerated. Several attempts (n=3) showed returned no significant improvement. In FIG. 18, the large frequency decrease due to NaOH is not shown to more clearly depict smaller change due to hybridization.

Figure 19:
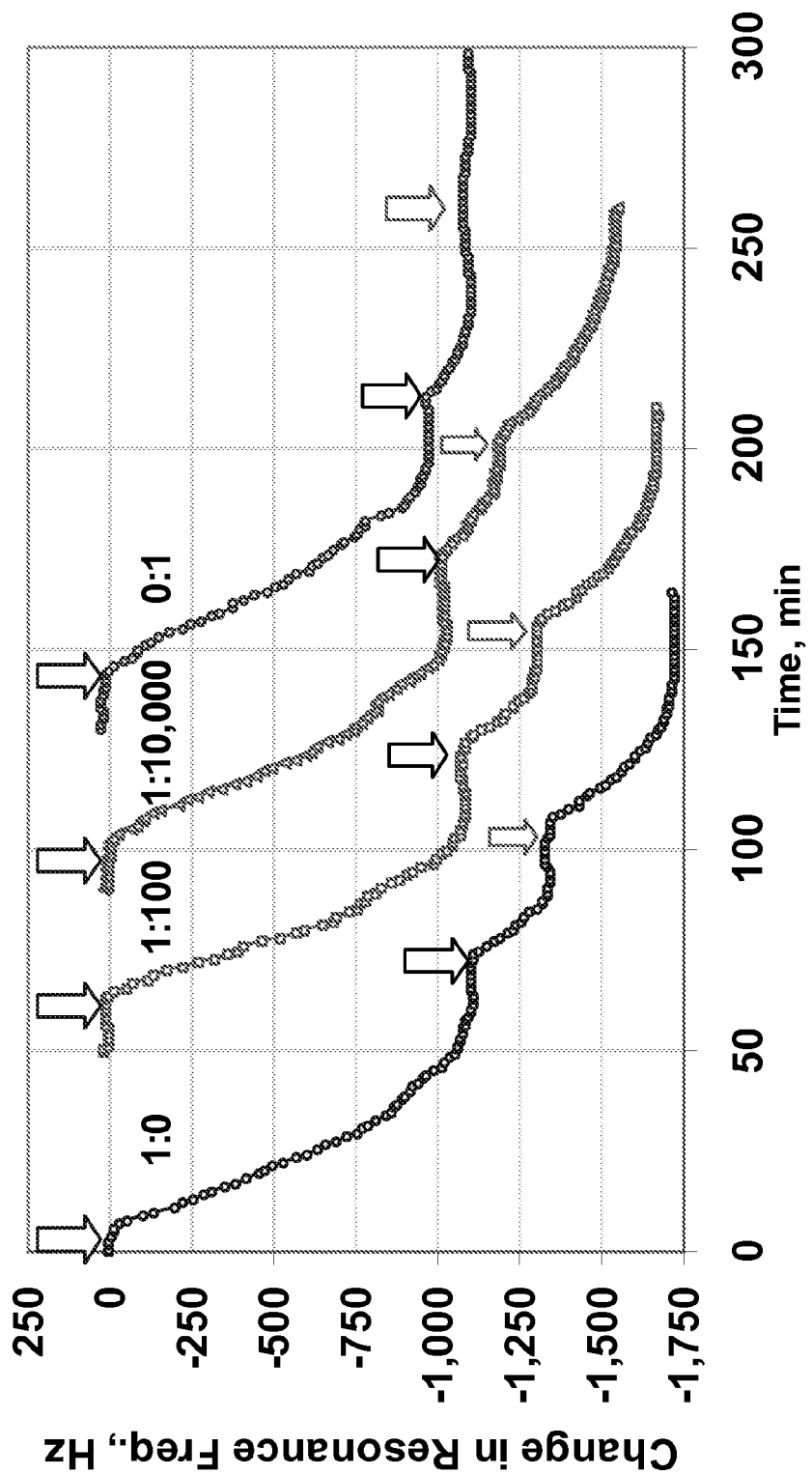
FIG. 19 is a plot illustrating example results of the detection of target nucleic acid in the presence of non-complementary nucleic acids.
Figure 20:
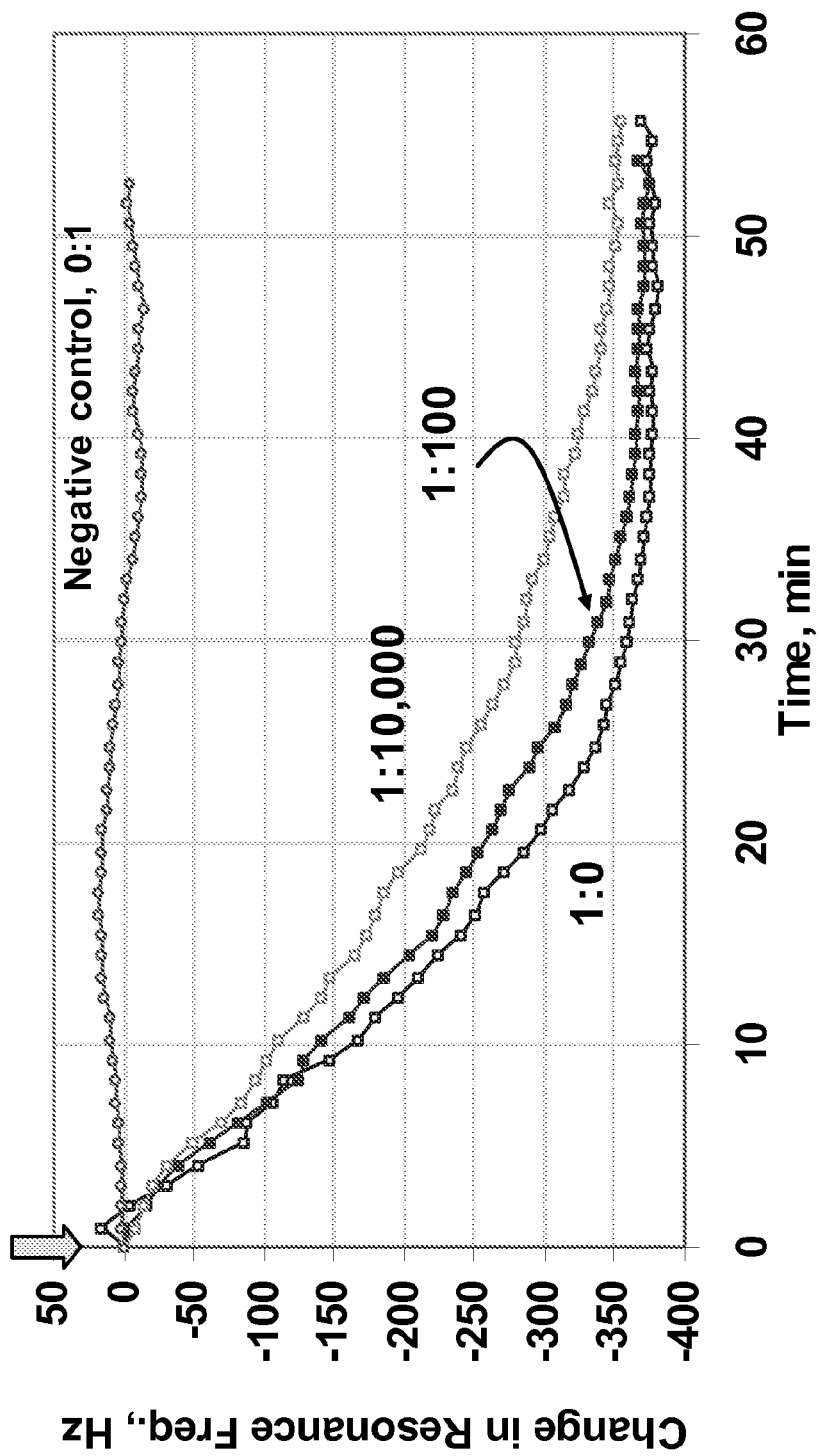
FIG. 20 is a plot illustrating the relative response from four example results of FIG. 19.

Using the experimental protocol used earlier, the PEMC-B sensor was first exposed to 10 mL of thiolated 100 nM probe and then to 1 μM MCH. Samples (30 mL) containing mixtures of complementary and non complementary ssDNA were prepared in mole ratios of 1:0, 1:100, 1:10,000, and 0:1, where the complementary ssDNA concentration was kept constant at 167 fM. The total complementary strand was kept constant at 5 femtomoles in all experiments. The sensor was cleaned after each hybridization experiment, and was re-immobilized with freshly prepared thiolated probe. The detection was done in the order of 1:100, 1:10,000, 1:0 and finally 0:1. As shown in FIGS. 19 and 20, the response is true to target in terms of total frequency change (within ±6%), but hybridization kinetics was slower when large non complementary strands were present. FIG. 19 shows the entire experimental sequence in a time-shifted fashion for clarity, whereas FIG. 20 shows only the hybridization from the point where the target oligonucleotide first entered the sample flow cell chamber. Note that immobilization of thiolated probe on the sensor surface resulted in frequency decrease of 975 to 1,110 Hz for the four cases, and is within ±6% of the mean.

We attribute the variance to sensor surface preparation due to the intervening cleaning step. When the sensor was exposed to target sample consisting of all non complementary ssDNA (sample 0:1) there was no observable shift in resonance frequency. The other samples 1:10,000, 1:100, and 1:0 caused frequency decrease of 353±12,370±9 and 382±17 with response times of 52, 39, and 37 minutes, respectively. The total response is well within the expected variation of ±6%, but the time required for reaching maximum hybridization was affected by the present of non complementary strands. We attribute the small variation in steady state resonance to the continuous flow combined with constant vibration of the sensor surface.

To analyze the kinetics of hybridization we assume a first order Langmuir kinetics. If $\Delta f_\infty$, is the maximum frequency change due to hybridization the sensor response can be represented by $$(\Delta f) = (\Delta f_\infty)(1 - e^{-k_{obs}\tau}) \qquad (\text{Eq. 1})$$

where, $(\Delta f)$ is the resonance frequency change at time t, and due to hybridization and $k_{obs}$ is the overall rate of hybridization. The above equation can be rearranged as $$\ln\left(\frac{(\Delta f_\infty) - (\Delta f)}{(\Delta f_\infty)}\right) = -k_{obs}\tau \qquad (\text{Eq. 2})$$

Using short time data, the sensor response can be plotted as noted in Eq. 2 and the rate constant $k_{obs}$ can be determined with good accuracy. $k_{obs}$ values obtained for sample 1:0, 1:100, and 1:10,000 were 0.047±0.006 min$^{-1}$ ($R^2$=0.99), 0.062±0.006 min$^{-1}$ ($R^2$=0.98), and 0.072±0.008 min$^{-1}$ ($R^2$=0.98) respectively. That is, a 35% reduction in hybridization rate constant was found in presence of 10,000 times extraneous 10-mer. This is not an unexpected result as the non complementary 10-mer would reduce transport of target sequence to the sensor surface. However, the constant vibration of the sensor and the continuous flow of sample allow the complementary strand to finally reach the sensor surface.

Figure 21:
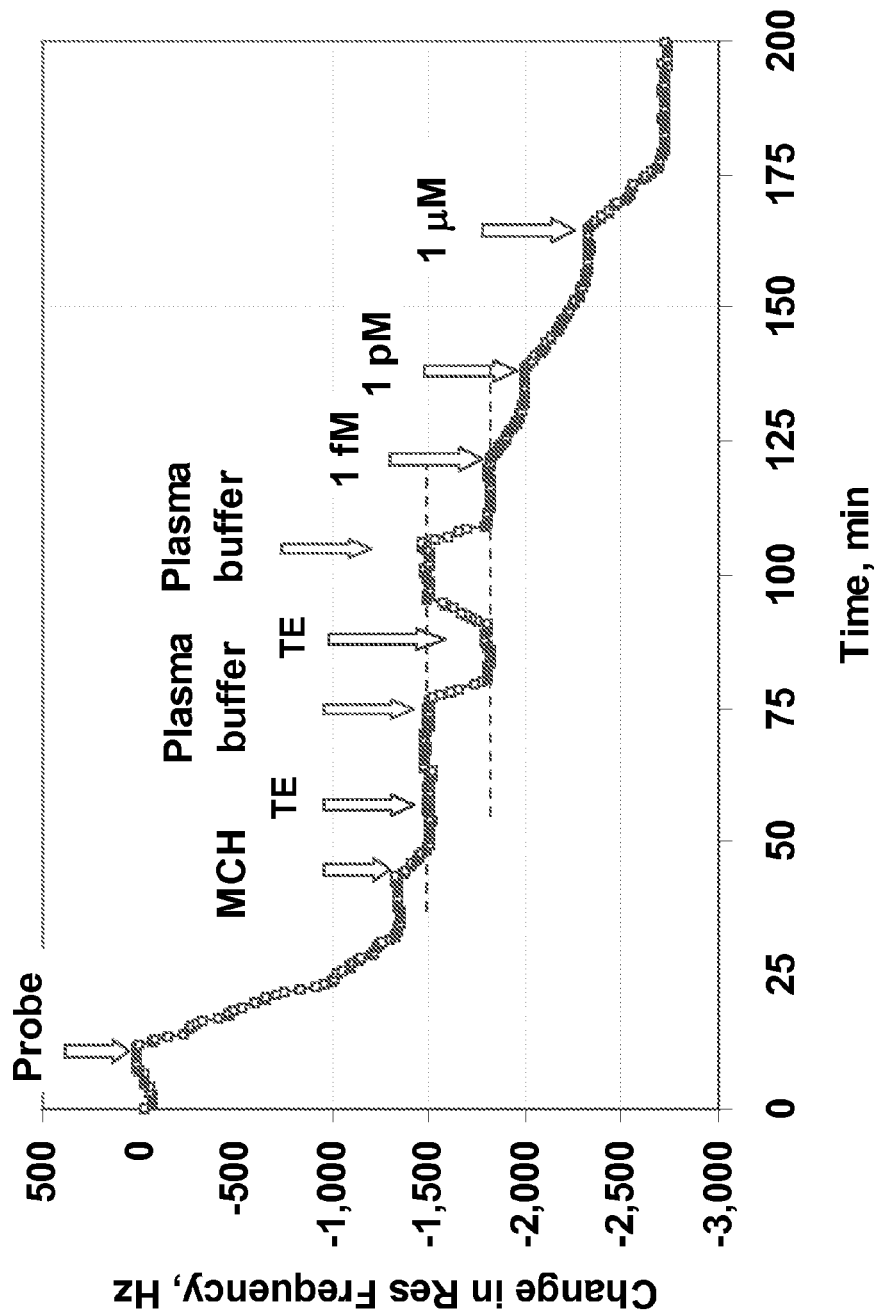
FIG. 21 is a plot illustrating examples results of the detection of target nucleic acid in human plasma.
Figure 22:
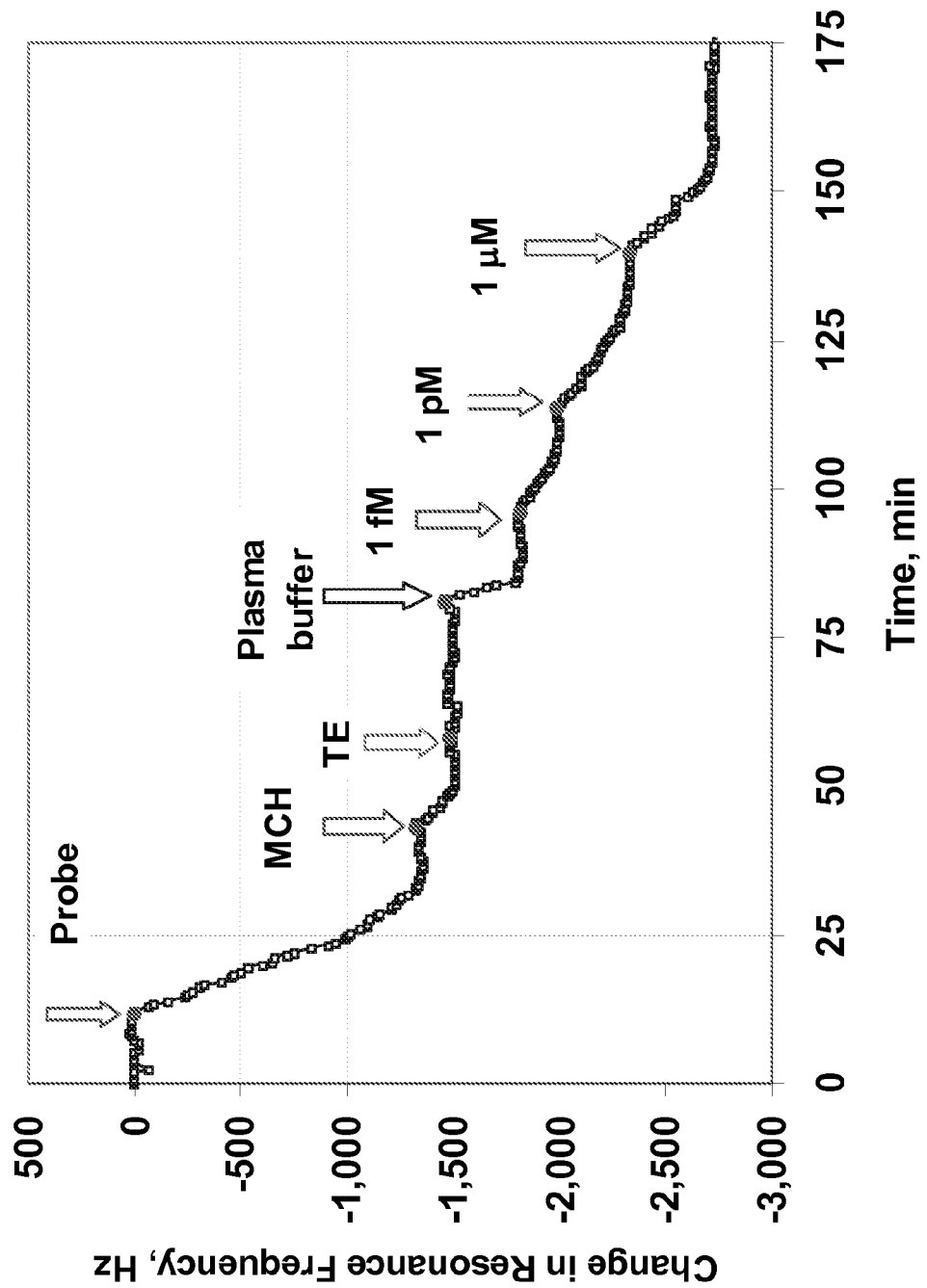
FIG. 22 is a plot illustrating examples results of the detection of target nucleic acid in a buffer containing human plasma.
Figure 23:
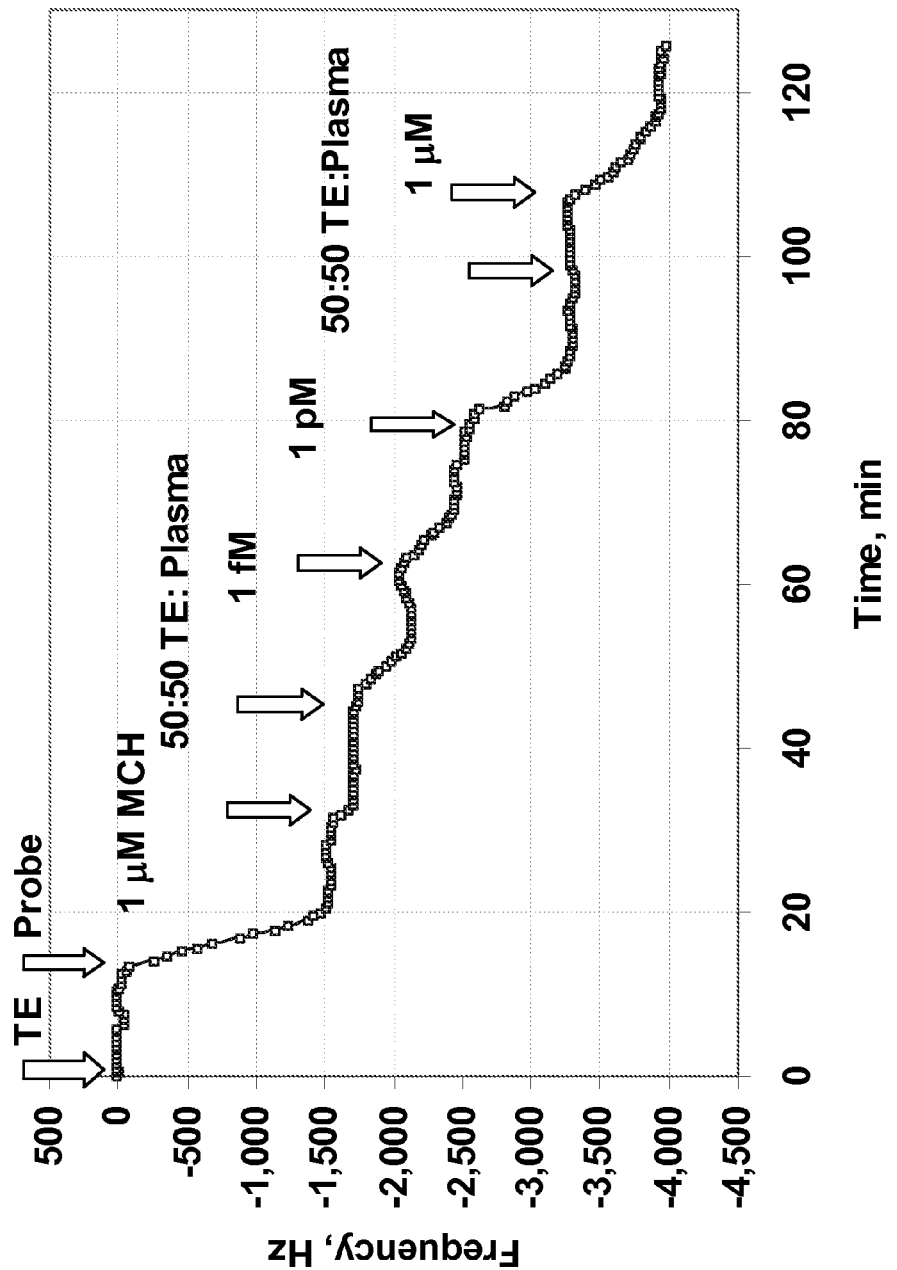
FIG. 23 is a plot illustrating examples results of the detection of target nucleic acid in a buffer containing human plasma.
Figure 24:
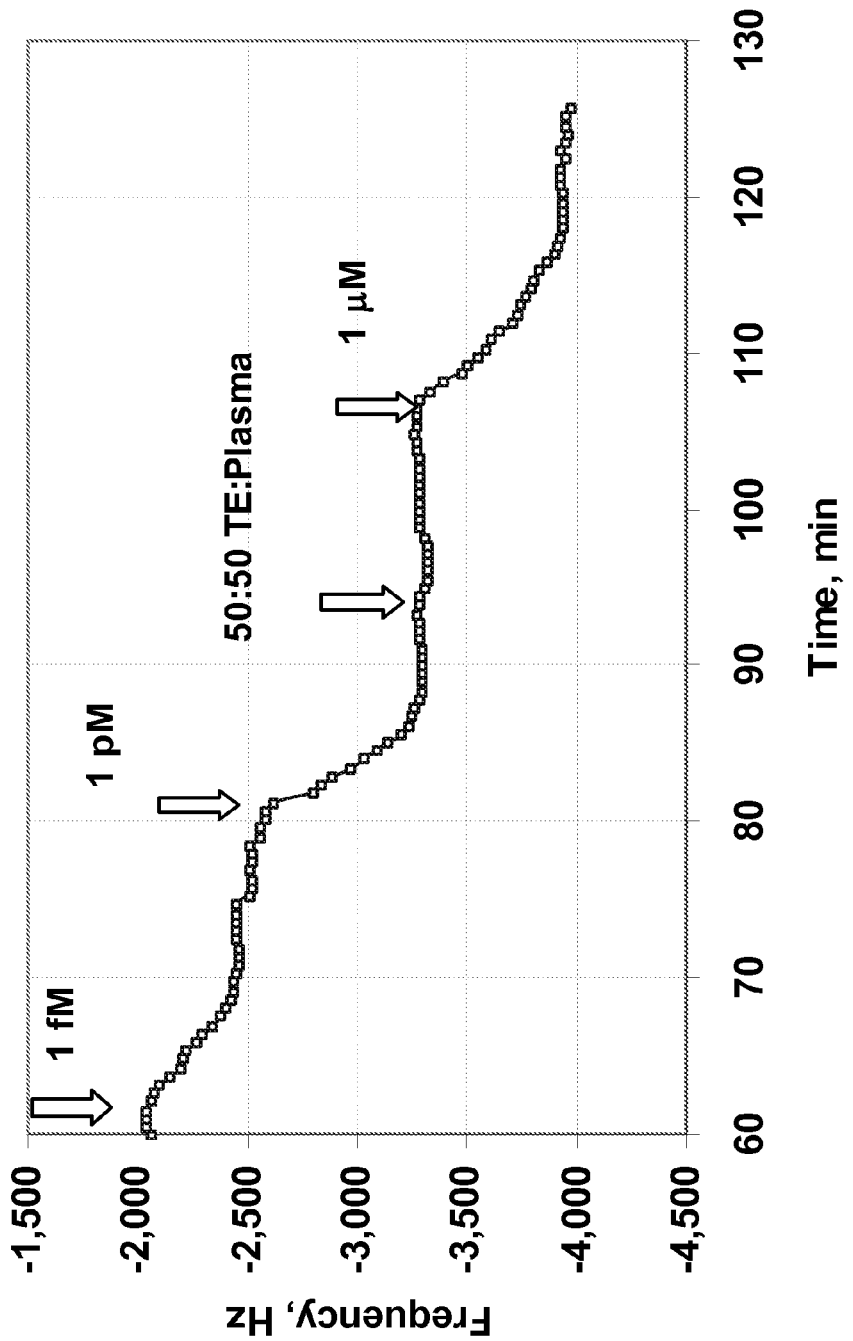
FIG. 24 is a plot illustrating examples results of the detection of 1 fM, 1 pM, and 1 µM target nucleic acid from FIG. 23.

After obtaining a stable baseline in TE buffer, freshly prepared 2 mL 500 pM thiolated probe was pumped through the flow-cell harboring PEMC-C maintained at 32.11±0.1° C. Resonance frequency of PEMC-C was 968.50 kHz in air and 899.52 Hz in TE buffer. As shown in FIG. 21, the probe immobilization resulted in a decrease of 1,3352±28 Hz. A 2 ml of 1 μM MCH in TE buffer was then flowed to optimize the sensor surface. Density of human plasma (~1.025 g/cm$^3$) is greater than TE buffer. The "plasma buffer" consisting of equal volume of TE buffer and human plasma. Since the solids present in the plasma clogged the experimental apparatus (tubing and valves), it was centrifuged at 4,000 g for 3 minutes and the clear fluid was recovered for use. After mixing with TE buffer very small coagulants were formed and were visible, but were not removed. The composition of plasma buffer was adjusted to make the final "plasma buffer" composition as 10 mM Tris-HC 1, 1 mM EDTA with 1 M NaCl. After flowing MCH, TE buffer was introduced followed by the plasma buffer to equilibrate the flow cell and the sensor with the higher density plasma buffer. Flow of plasma buffer resulted in a decrease of 240±14 Hz. At 92 min, TE buffer was reintroduced, and as shown in FIGS. 21 and 22, the resonance frequency recovered to the value prior to the introduction of plasma buffer. The recovery was within 12 Hz which is within the measurement noise level. This recovery and other experiments (n=7) indicate that no plasma components adsorb permanently on a sensor prepared with the thiolated probe and MCH. At 106 min, plasma buffer was reintroduced at 0.6 mL/min, and the resonance frequency decreased by 303±112 Hz and reached a constant value. Samples (2 mL) of complementary strands at 1 fM, 1 pM and 1 μM concentration were prepared in plasma buffer, and were introduced sequentially. As seen in FIG. 21, and magnified in FIG. 14, these three targets caused frequency decreases of 178±18 Hz in 16 minutes, an additional −341±14 Hz in 21 minutes, and finally a further change of −384±16 Hz in 16 minutes, respectively for the three concentrations. That is, similar to the results shown in FIGS. 16, 17, 19, and 20, the vibrating PEMC sensor showed intrinsic specificity of detecting complementary target strands in 50% human plasma. The ratio of hybridization response to probe response (=903/1, 335) is 0.68 and is close to the theoretical value noted earlier of 0.65. The measured shift due to hybridization was measured in plasma buffer while that of the probe attachment was measured in TE buffer. Since the plasma buffer introduced a shift of about 22% of probe+MCH response (from 1,501 to 1,804 Hz, an increase of 22%) it is noted that the two shifts are not on an equal basis. This is due to the physical properties (density and viscosity) of the plasma buffer. Thus correcting for the change in plasma buffer-induced response, the ratio of hybridization to probe (=903/[1.22*1,335]) is 0.55 and therefore one would estimate that 85% hybridization was obtained at the end of the experiment. The cumulative response in plasma (−178±18 Hz, −519±14 Hz and −906±16 Hz) was slightly lower than the response obtained in TE buffer (−210±12 Hz, −618±15 Hz and −968±18 Hz) for the three concentrations of 1 fM, 1 pM, and μM. The slightly lower response in plasma buffer is within the expected variations due to surface preparation and sensor sensitivity (PEMC-C vs. PEMC-A). The overall hybridization rate constant ($k_{obs}$) obtained was 0.061±0.005 min$^{-1}$ ($R^2$=0.950), 0 86±0.006 min$^{-1}$ ($R^2$=0.90), and 0.093±0.005 min$^{-1}$ ($R^2$=0.82) for 1 fM, 1 pM, and 1 μM, respectively. In the experiments shown in FIGS. 14 and 15, the hybridization was performed starting with a fresh probe immobilized sensor each time while in FIGS. 21 and 22, the targets were introduced sequentially. That is, only for the 1 fM sample, the sensor was fresh, and for 1 pM and 1 μM samples the sensor surface contained some hybridized probes due to the preceding step. Therefore, $k_{obs}$ value for 1 fM can be compared on an equal basis. One notes that at 1 fM $k_{obs}$ value in plasma buffer is 34% lower than in TE buffer. In FIG. 22, another hybridization experiment in plasma buffer is shown. Note that the response to probe immobilization (1,348±9 Hz) and to MCH (162±6 Hz) is almost identical to results in FIG. 21. The plasma buffer response is lower (312 Hz) and the three concentrations gave 179±6, 335±7, and 382±6 Hz for a total response of 896 Hz. This represents a hybridization of 85% determined as was done with data in FIG. 21.

In order to determine whether higher sensitivity can be achieved in plasma three experiments were conducted at high probe density. A sample result is shown in FIGS. 21 and 22. Probe immobilization was carried out with 2 mL of 50 nM which caused a 1,557 Hz decrease in resonance frequency which is ~16% higher than in FIGS. 15 and 16. Exposure to 2 mL of 1 μM MCH resulted in a further decrease of 163 Hz. Introduction of plasma buffer caused a shift of 408 Hz, representing almost 26% of probe response. Response to 1 fM, 1 pM and 1 μM were, respectively, 329, 838, and 671 for each of the steps. The smaller response for MCH (163 Hz) compared to earlier result in FIGS. 13 and 14 suggests that more of the gold sites were occupied by the probe. The 1 pM and 1 μM induced a higher sensor response as well. Introduction of plasma buffer after the 1 pM target induced essentially zero response. The total cumulative response to complementary ssDNA is 1,838 Hz. Correcting for plasma buffer effect, hybridization efficiency (1,838/[1.26*1,557]) is 0.94 which is higher than the theoretical value of 0.75.

Detection of Nucleic Acids from *E. coli*

Single-stranded thiolated 19-mer oligonucleotide complementary to stx2 (Gene Accession No: AF 525041.1), HS-C$_6$H$_{12}$-5'-CCA CTC TGA CAC CAT CCT C-3' (SEQ ID NO:5) was purchased from IDTDNA (Coralville, Iowa). The gene sequence of interest was searched using BLAST and a 19-mer hybridization probe was selected using Primer 3. The melting and hybridization temperature and Na$^1$ concentration were determined using OligoAnalyzer 3.0 using the lowest permitted concentration. The lyophilized stx2 probe was reconstituted as a stock solution of 6.42 μM in TE buffer (10 mM Tris-HCl, 1 mM EDTA, pH 8.5) in 50 mM or 1 M NaCl and diluted in TE buffer to the desired concentration prior to use.

Radiation-killed *E. coli* O157:H7 (1×10$^9$ cells/mL) is a gift from Dr. Shu-I Tu (USDA-ERRC, Wynnewood, Pa.). Non-pathogenic wild strain *E. coli* JM101 was obtained locally. Both were reconstituted in TE buffer or PBS at a concentration of 1×10$^6$ and 1×10$^5$ cells/mL. For verification, the stock solution containing 1×10$^5$ cells/mL was analyzed for particle size distribution (PSD) in a Coulter Multisizer II analyzer (Beckman Coulter Inc., CA) with a 30 μm orifice tube, 1 M NaCl electrolyte and a 100 μL sample. Several injections gave results ranging from 71,000 to 123,000 cells per mL with a mean of 94,000 cells per mL, verifying the diluted sample of 1×10$^5$ cells/mL.

Aliquot of 250 μL 65.8 μM thiolated ssDNA probe in disulfide form was reduced with 0.0039 g of dithiothreitol (DTT) for 30 min at room temperature. Unreacted DTT was removed using Sephadex® G-25 columns (PureBiotech LLC, New Jersey) following the vendor supplied protocol. The effluent, free of DTT, was diluted in TE buffer to a concentration of 1 pM or 10 pM and used immediately.

Two sample preparations were used. The first genomic DNA (gDNA) ("Sample I") extraction method, Sample-I from *E. coli* O157:H7 or JM11 was extracted using the protocol adapted from Mao, et al, *Biosensors & Bioelectronics*, 21 (2006) 1178. An aliquot of 1.5 mL TE buffer containing 50,000 *E. coli* cells was centrifuged at 10,000 g for 5 minutes, and the supernatant discarded. To the resulting pellet, 50 μL of 1% Triton X-100 was added, immersed in boiling water for 10 minutes, and then cooled at 2-3° C. for 15 minutes, and centrifuged at 10,000 g for 3 minutes. The supernatant containing gDNA was pipetted into 10 mL TE buffer to make a stock solution. The stock solution was calculated to have gDNA of 22.5 pg/mL using the value of 4.5 fg DNA/cell. The DNA was sheared by squeezing through a 30-gauge ½ inch hypodermic needle 25 times. Such shearing produces DNA strands of 100-300 base pairs. The same procedure outlined above was used to extract gDNA from 50,000 *E. coli* JM101 and was used as control. The stock solutions were stored at −20° C. until use. Just prior to a detection experiment, the stock gDNA solution was denatured by heating in 98° C. bath for 10 minutes, followed by cooling and maintaining at 2-4° C. for 10 minutes. The denatured DNA was then diluted to the desired concentrations in TE buffer.

The second gDNA ("Sample II") was extracted from *E. coli* O157:H7 cells suspended in beef wash. Four grams of ground beef, purchased locally, was suspended in 12 mL TE buffer, vortexed for one minute and allowed to stand at room temperature for 25 minutes. The 25-minute stand period allowed large particles to settled out; 4.0 mL was removed and centrifuged at 1,000 g for 2 minutes, and 1.5 mL of the clear, but reddish supernatant (called beef wash) was removed and radiation-killed 50,000 *E. coli* O157:H7 cells were added and mixed.

DNA was then extracted using the method described for Sample-I. The resulting gDNA was diluted in 10 mL of TE buffer that gave a stock solution containing extracted DNA of 22.5 pg/mL (calculated). The stock gDNA solution was sheared as described earlier and stored at −20° C. until use. Compared to Sample-I, since beef wash contains other cellular material, the sample not only consisted of gDNA of *E. coli* O157:H7 origin but also other cellular DNA from beef.

Resonance frequency of a gold coated PEMC sensor was allowed to come to steady state under 0.5 mL/min TE buffer flow in a temperature controlled flow-cell maintained at 37.3±0.2° C. The electrodes of the sensor were connected to an impedance analyzer (HP4192A or HP 4294A) interfaced to a PC running a custom LabView™ program that acquired resonance frequency values. Three-point moving median value was determined and taken to represent the sensor response. Two mL of freshly prepared probe solution was introduced into the flow circuit, initially in a once through mode for 4 minutes and then in a recirculation mode. The flow loop has a hold-up volume of 2.2 mL and thus the probe was diluted in the flow loop by 10%. The probe chemisorbed to sensor gold surface via the thiol group, and sensor responded by a decrease in resonance frequency. After the sensor resonance frequency reached steady state, TE buffer was flowed in a once through mode to flush the flow circuit followed by the introduction of either a control or a test sample. In some experiments we included a fill step with 1-mercapto-6-hexanol (MCH) between the probe immobilization and the target sample introduction.

Initial tests were conducted at two probe concentrations (1 and 10 pM) and at various gDNA concentrations (1 to 10 pg/mL). The concentration of gDNA was chosen based on more than 18 experiments at various concentrations. The sample at 1 pg/mL is equivalent to ~220 cells/mL. Both 1 and 10 pM probe concentrations are suitable for sensor detection. The hybridization was monitored by collecting resonance frequency of the PEMC sensor. The sample was prepared by heating at 98° C. for 10 minutes to denature the double stranded DNA, followed by rapid cooling at 2-3° C. for 10 minutes to preserve the single strands formed. The fragmented and denatured DNA was then used immediately in detection experiments.

Figure 25:
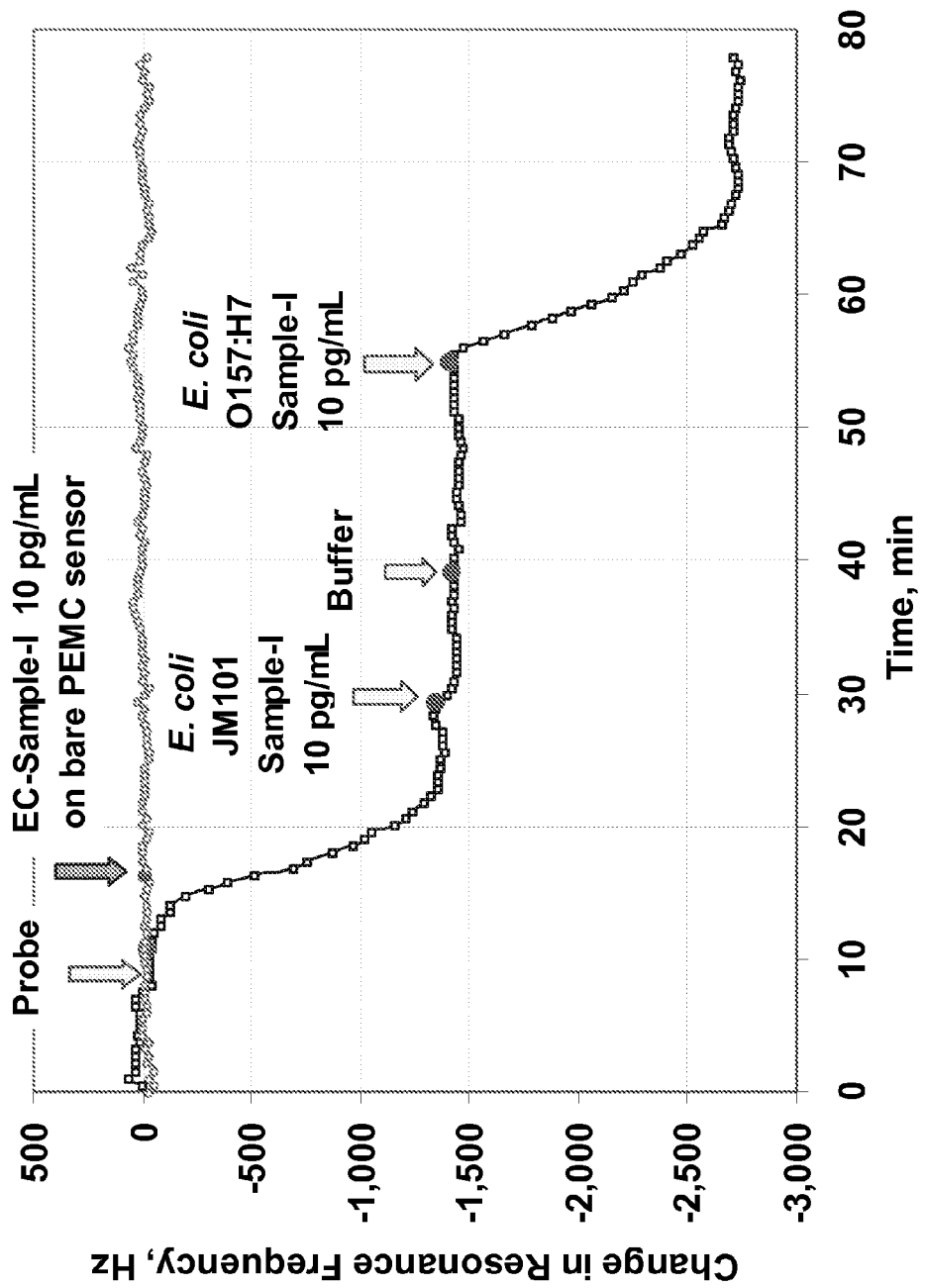
FIG. 25 is a plot illustrating example results of the detection E. coli DNA in a beef preparation.

The Sample-I contains gDNA in presence of *E. coli* protein. After the sensor PEMC-B was prepared with 2 ml of 10 pM probe, the flow circuit was flushed with TE buffer. FIG. 25 shows that the flow of probe solution resulted in a shift of −1,398±28 Hz, and was complete in 10 minutes. At t=28 minute, the flow was switched to 2 mL of freshly denatured 10 pg/mL gDNA (equivalent to 4,450 cells) extracted from *E. coli* JM101 (control Sample-I). The *E. coli* JM101 DNA used as a negative control caused a change of −78±11 Hz, which is not significant. This was followed by buffer flush step that caused no change in resonance frequency, and the response remained within the noise level of ±20 Hz. At t=54 minute, 2 mL of 10 pg/mL crude *E. coli* O157:57 gDNA (Sample-I) was injected which caused a rapid response of 1,255±19 Hz in 12.5 minutes with a first order rate constant of 0.18 min$^{-1}$. The response in FIG. 25 shows that sensor response occurs only when gDNA of *E. coli* O157:H7 origin is present, and not for the wild strain. Hybridization rate is not compromised in presence of contaminating cellular protein. FIG. 25 shows the control response of plain Au-coated PEMC-B carried out at a different time, exposed to 2 mL of 10 pg/mL gDNA extract (Sample-I) which gave zero response.

Figure 26:
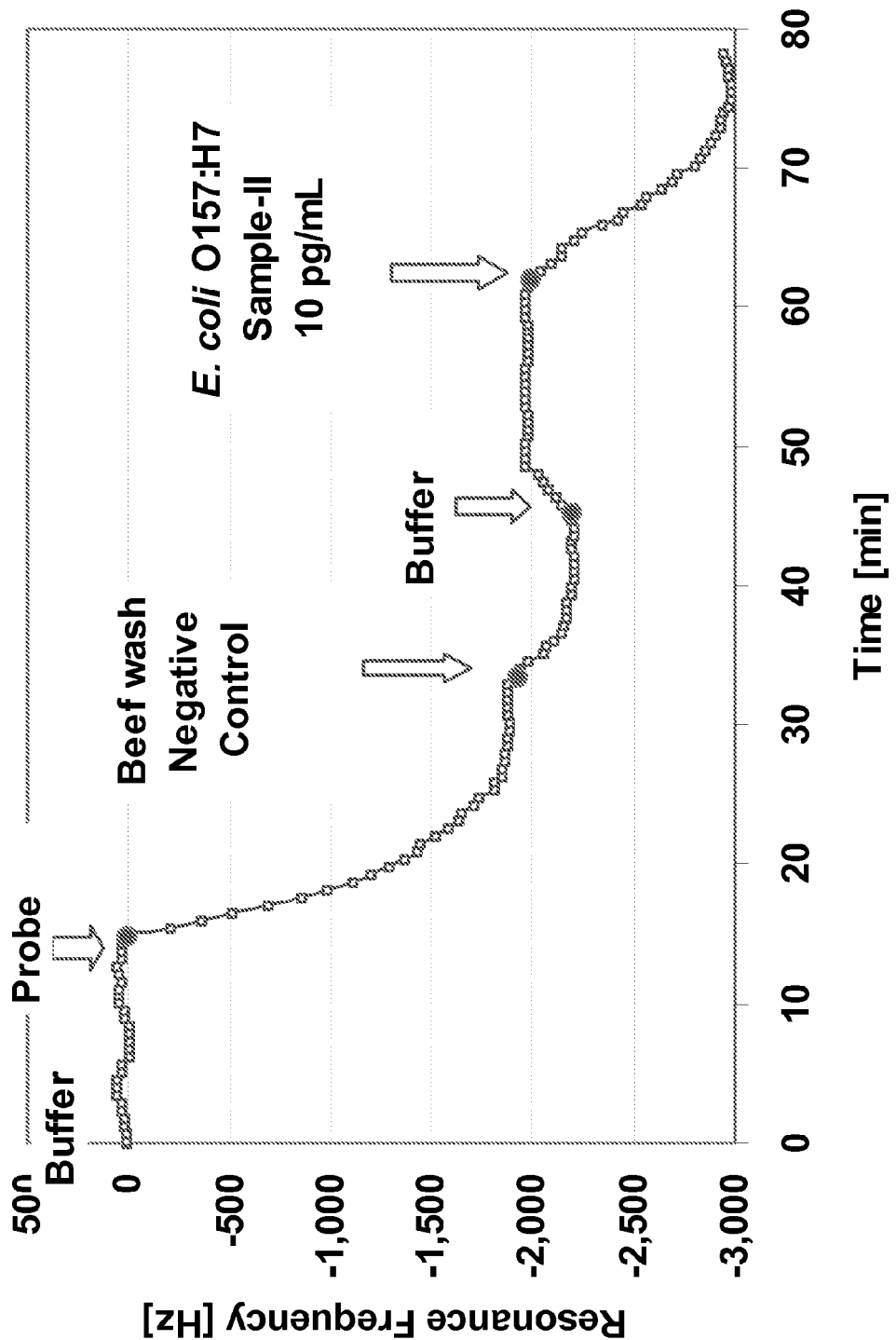
FIG. 26 is a plot illustrating example results of the detection E. coli DNA in a beef preparation after exposing the sensor to a beef wash.

Sample-II prepared with beef wash were of pale yellow color, due to the lysed beef blood cells. Unpurified samples were tested at 10 pg/mL (equivalent to 2,225 cells/mL). For negative control beef wash was used with sensor prepared with the stx2 probe. All four experiments prepared with the starting beef wash sample gave positive detection obtained with PEMC-B. FIG. 26 (representative result). Introduction of 1 pM probe resulted in a resonant frequency change of −1,449±21 Hz. MCH was not used in this series of experiments. After the probe immobilization, beef wash sample was introduced as negative control. Beef wash sample was prepared by mixing 200 μL of solution labeled as "beef wash" with 2 mL TE buffer, thus forming a 9% beef wash in TE buffer. The beef wash negative control caused a response of −327±11 in ~7 minutes, and is due to its density difference from PBS. When buffer was re-introduced the frequency recovered by +236±14 Hz, resulting in a net change of −91±11 Hz. The lack of full recovery of resonance frequency suggest that a small amount of proteinaceous matter either adsorbed onto the sensor and/or onto the immobilized probe. After obtaining a stable baseline in buffer, 2 mL of 10 pg/mL of *E. coli* O157:H7 gDNA (Sample-II) was introduced, and resulted in a response of 1,005±15 Hz in 14.2 minutes with a hybridization rate constant of 0.13 min$^{-1}$. Three repeat experiments with the same surface preparation gave a response in the range of 940±16 to 1090±21 Hz with a mean of 1024 Hz (n=4). Hybridization time was 13 to 15 minutes, with an average rate constant of 0.14 min$^{-1}$.

Detection of Single Nucleotide Polymorphism

The uniform width of the sensor was 1 mm, and the lengths of PZT (Type 5A, $d_{31}$=−190×10$^{-12}$ m/V, 127 μm thick) and quartz (160 μm thick) were 5 and 4 mm, respectively. The PZT was anchored in a 6 mm glass tube, and the quartz piece was bonded on the PZT such that 0.8±0.1 mm of quartz was overhanging off the PZT. The overhanging section of quartz acted as the sensing surface. The quartz was not anchored on the glass tube and the distance between the glass tube and the quartz was 0.5±0.1 mm. The overhanging sensing surface was sputtered on both sides with a 100 nm gold layer in a Denton Desk II System (Denton Vacuum, New Jersey) at 1 mTorr. The gold film yielded predominantly (>95%) a polycrystalline Au <111> surface as determined by X-ray diffraction.

Single-stranded thiolated 15-mer oligonucleotide probe sequence of 5'-thiolMC6-GGA AGA AGC TTG CTT-3' (SEQ ID NO:3) was purchased from IDTDNA (Coralville, Iowa). Three different targets of lengths 20 bases, 30 bases, and 60 bases were chosen such that all of them contained 15 bases complementary to the probe. Another set of targets of same lengths as above but containing a SNP was also chosen and in the case of 60 bases, the SNP sequences consisted of one with base G and another with base C (i.e., SNP or base pair mismatch) at the location that would have consisted of a T for complementarity to the A in the corresponding region of probe material. Table 2 shows a list of all target sequences and the probe.

TABLE 2

| Target Reference | Target Description | Sequence |
|---|---|---|
| A | 60 base complementary Sequence | 5'-ACC CGT CCG CCA CTC GTC AGC AAA GAA GCA AGC TTC TTC CTG TTA CCG TTC GAC TTG CAT-3' (SEQ ID NO: 6) |
| B | 60 base sequence with SNP G | 5'-ACC CGT CCG CCA CTC GTC AGC AAA GAA GCG AGC TTC TTC CTG TTA CCG TTC GAC TTG CAT-3' (SEQ ID NO: 7) |
| C | 60 base sequence with SNP C | 5'-ACC CGT CCG CCA CTC GTC AGC AAA GAA GCC AGC TTC TTC CTG TTA CCG TTC GAC TTG CAT-3' (SEQ ID NO: 8) |
| D | 30 base complementary sequence | 5'-GTC AGC AAA GAA GCA AGC TTC TTC C TG TTA-3' (SEQ ID NO: 9) |
| E | 30 base sequence with SNP G | 5'-GTC AGC AAA GAA GCG AGC TTC TTC C TG TTA-3' (SEQ ID NO: 10) |
| F | 20 base complementary sequence | 5'-CAA AGA AGC AAG CTT CTT CC-3' (SEQ ID NO: 11) |
| G | 20 base sequence with SNP G | 5'-CAA AGA AGC GAG CTT CTT CC-3' (SEQ ID NO: 12) |
|  | Probe | 5'- HSC$_6$H$_{12}$-GGA AGA AGC TTG CTT-3' (SEQ ID NO: 3) |

The melting temperature and subsequently hybridization temperature and Na$^+$ concentration for hybridization were determined using Primer 3 and OligoAnalyzer 3.0 software available at IDTDNA website (http://www.idtdna.com/analyzer/Applications/OligoAnalyzer/). The hybridization conditions were selected for the complementary probe and target pair and the same conditions were used for the SNP sequences as well. The lyophilized DNA oligonucleotide probe was reconstituted at a stock concentration of 6.4 µM in TE buffer (10 mM Tris-HCl, 1 mM EDTA, pH 8.5) in 75 mM NaCl and diluted to desired concentrations prior to use. The lyophilized target DNA were reconstituted in 5 mL TE buffer resulting in concentrations in the micromolar range with differences resulting from actual amount of oligos for each target. At 75 mM concentration of NaCl, the melting temperature, Tm of the complementary 15 bases is 36.5° C., therefore, a hybridization temperature of 30.5±0.1° C. was used as the flow-cell temperature. 0.22 micron filtered DI water (Milli-Q plus ultra pure water system, 18.2 M Ω) was used to prepare TE buffer which was de-aerated before use. All other chemical reagents described in this paper were purchased from Sigma-Aldrich.

Thiolated probe ssDNA was obtained in disulfide form and was reduced prior to use by adding 0.00039 grams of dithiothreitol (DTT) powder to each aliquot containing 250 µL of 6.4 µM thiolated probe and reacting at room temperature for 30 minutes. Excess DTT which can compete with the probes for gold surface was removed using Sephadex® G-25 columns (PureBiotech LLC, New Jersey), following the vendor supplied protocol. The effluent, free of DTT, was diluted in degassed TE buffer to a concentration of 1 pM and used within 2-3 minutes for probe immobilization.

Figure 28:
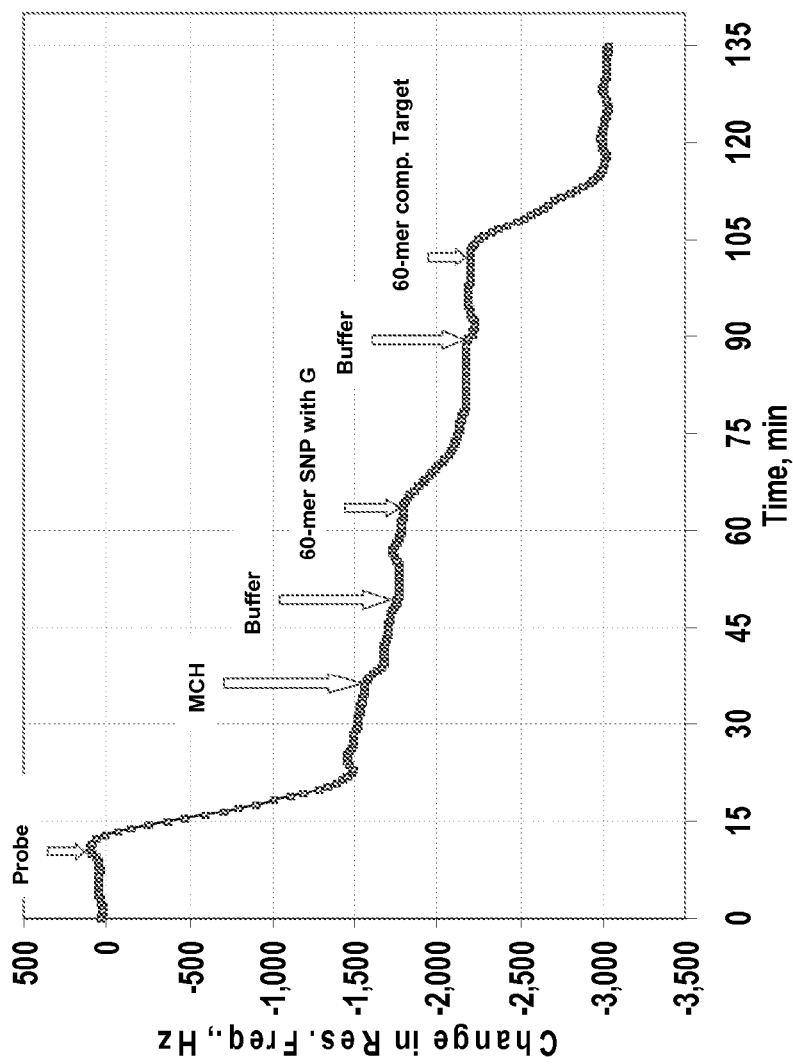
FIG. 28 is a plot illustrating example results of the binding of a 60-mer target single stranded DNA containing a SNP ("60-mer SNP with G"), to a probe material, containing a 15-mer ssDNA. The binding of 60-mer SNP with G is followed by the binding of a 60-mer target ssDNA that does not have the SNP (e.g., has complete complementarity to the corresponding region on the probe material).

The probe sequence of 5'-HS-C$_6$H$_{12}$-GGA AGA AGC T TG CTT-3' (SEQ ID NO:3) where the fifth base from the 3' end (bolded and underlined above) is "T" which means it's complementary base on the target is an "A". The sensor was first secured in flow-cell maintained at 30.5±0.1° C. and equilibrated in running TE buffer. 2 mL of 1 pM probe solution was then flowed through the sensor. The flow of probe through the sensor resulted in an immediate and sharp decrease in resonant frequency due to attachment of thiolated DNA on the sensor surface. The probe DNA molecules bind with the Au<111> sensor surface forming a strong thiolated bond. FIG. 28. 2 mL of 1 µM MCH solution is then flowed through the sensor to optimize the sensor as discussed in the earlier section of this report. The sensor was then flushed with TE buffer such that any remaining MCH or probe molecules were flushed out of the flow-cell and the tubing. 2 mL of 10 pM 60 bases target containing a SNP with base G (target B in Table 2) is then flowed, this resulted in a decrease of 366±18 Hz in 9.4±0.5 minutes. The flow-cell was then purged with TE buffer and at t=104 minute, 2 mL of 10 pM target (target A) containing a segment complementary to the probe sequence was flowed through. This resulted in an immediate decrease of 804±32 Hz in 12.6±0.5 minutes. FIG. 28 shows that the sensor responds to targets with one SNP, but to a lesser degree than the response for the complementary sequence.

Figure 29:
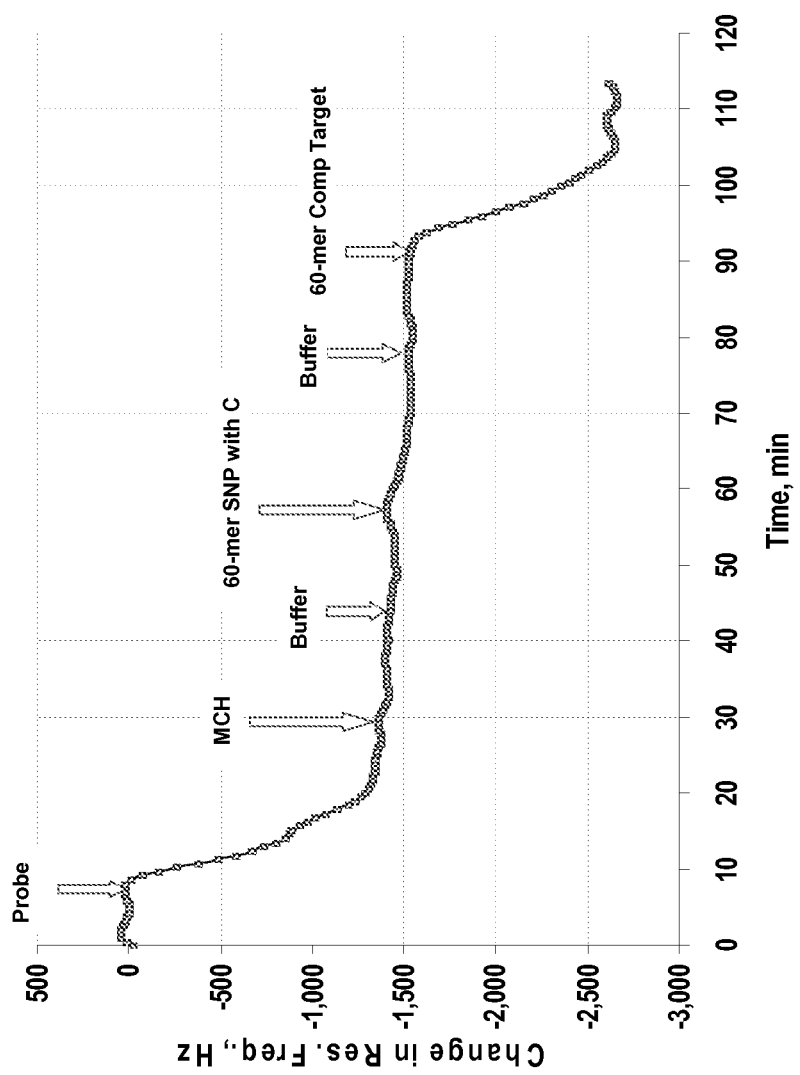
FIG. 29 is a plot illustrating example results of the binding of a 60-mer target single stranded DNA containing a SNP ("60-mer SNP with C"), to a probe material, containing a 15-mer ssDNA. The binding of 60-mer SNP with C is followed by the binding of a 60-mer target ssDNA that does not have the SNP (e.g., has complete complementarity to the corresponding region on the probe material).

FIG. 29 repeats the experiment presented in FIG. 28 but using target nucleic acid having a C (Target C in Table 2). The flow of 2 ml of 10 p SNP DNA solution resulted in a decrease of 121±22 Hz in 10.1±0.5 minutes. The flow-cell was then flushed with TE buffer and 2 mL of 10 pM complementary solution, this resulted in a change of 1,058±62 Hz in 11.2±0.5 minutes. FIG. 29 shows that the SNP sequence showed a lower response than in FIG. 28; but the total responses in FIGS. 28 and 29 were similar.

Figure 30:
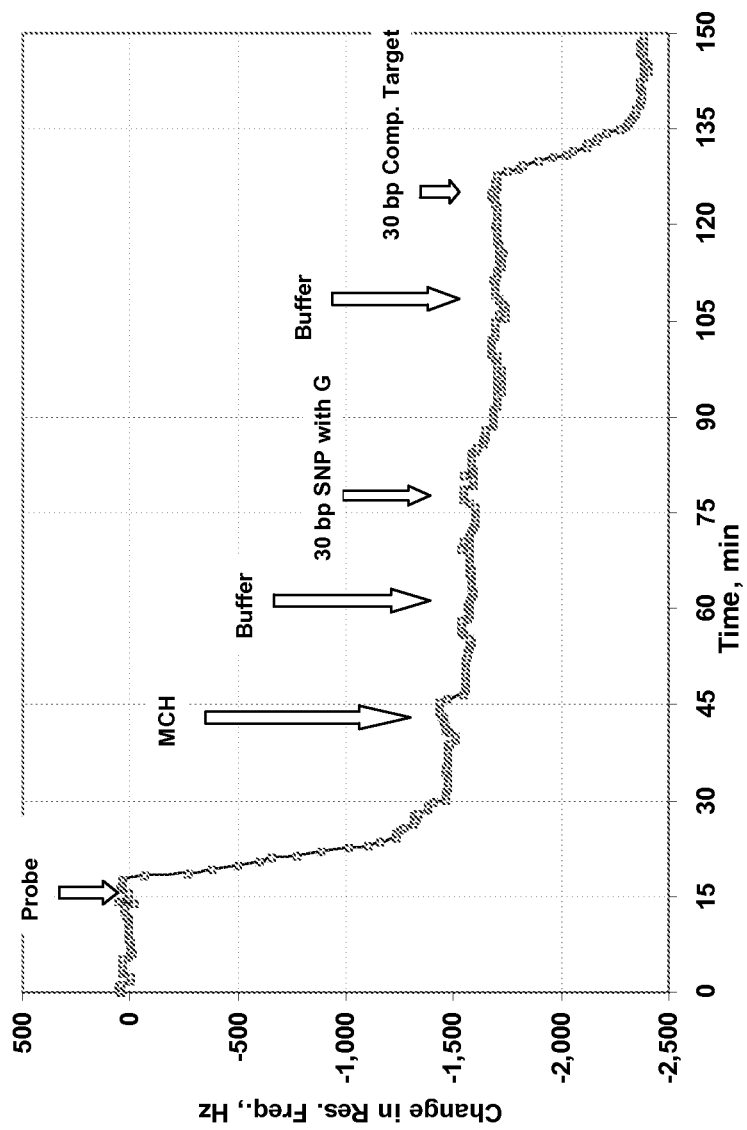
FIG. 30 is a plot illustrating example results of the binding of a 30-mer target single stranded DNA containing a SNP ("30-mer SNP with G"), to a probe material, containing a 15-mer ssDNA. The binding of 30-mer SNP with G is followed by the binding of a 30-mer target ssDNA that does not have the SNP (e.g., has complete complementarity to the corresponding region on the probe material).

FIG. 30 repeats the experiment presented in FIG. 28 but using 30 bp target nucleic acid. 2 mL of 10 pM 30 bases long target strand with a SNP base of G instead of T (Target D in Table 2) through a sensor immobilized with thiolated 15-mer probe. Flow of 30 bp SNP sequence showed a decrease of 107±21 Hz in 8.7±0.5 minutes but the flow of 2 ml of 10 pM complementary target (Target E in Table 2) showed a frequency decrease of 656±61 Hz in 8.7±0.5 minutes.

Figure 31:
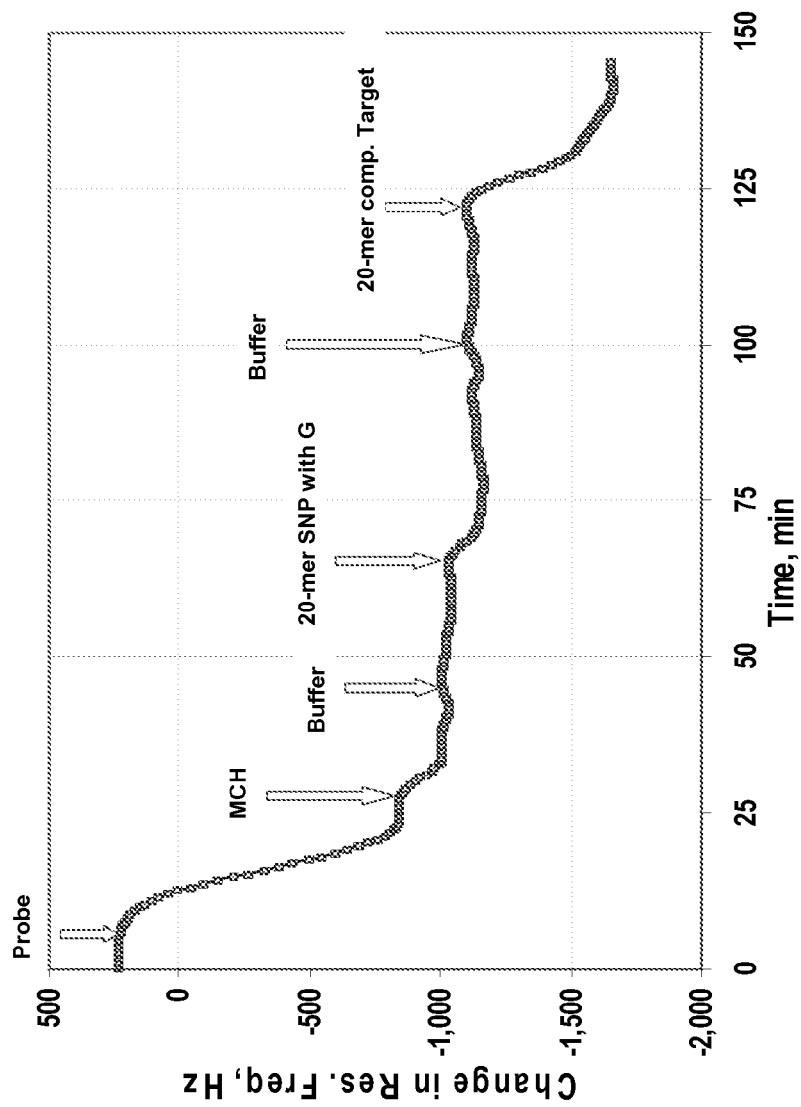
FIG. 31 is a plot illustrating example results of the binding of a 20-mer target single stranded DNA containing a SNP ("20-mer SNP with G"), to a probe material, containing a 15-mer ssDNA. The binding of 20-mer SNP with G is followed by the binding of a 20-mer target ssDNA that does not have the SNP (e.g., has complete complementarity to the corresponding region on the probe material).

FIG. 31 repeats the experiment presented in FIG. 30 but using 20 bp target nucleic acid. The same SNP and complementary sequences used above were now reduced from 30 bp to 20 bp such that the 15 bp on the target still remained complementary to the probe except in the case of SNP sequence where the SNP base of G instead of T was used.

Flow of 2 mL of 10 pM of 20 bp DNA target with a SNP (Target F in Table 2) resulted in a decrease of 89±16 Hz in 6.4±0.5 min. After flushing the flow-cell with TE buffer, 2 mL of 10 pM complementary 20 base DNA (Target G in Table 2) solution was flowed through and it resulted in a decrease of 583±41 Hz in 14.6±0.5 minutes.

Figure 32:
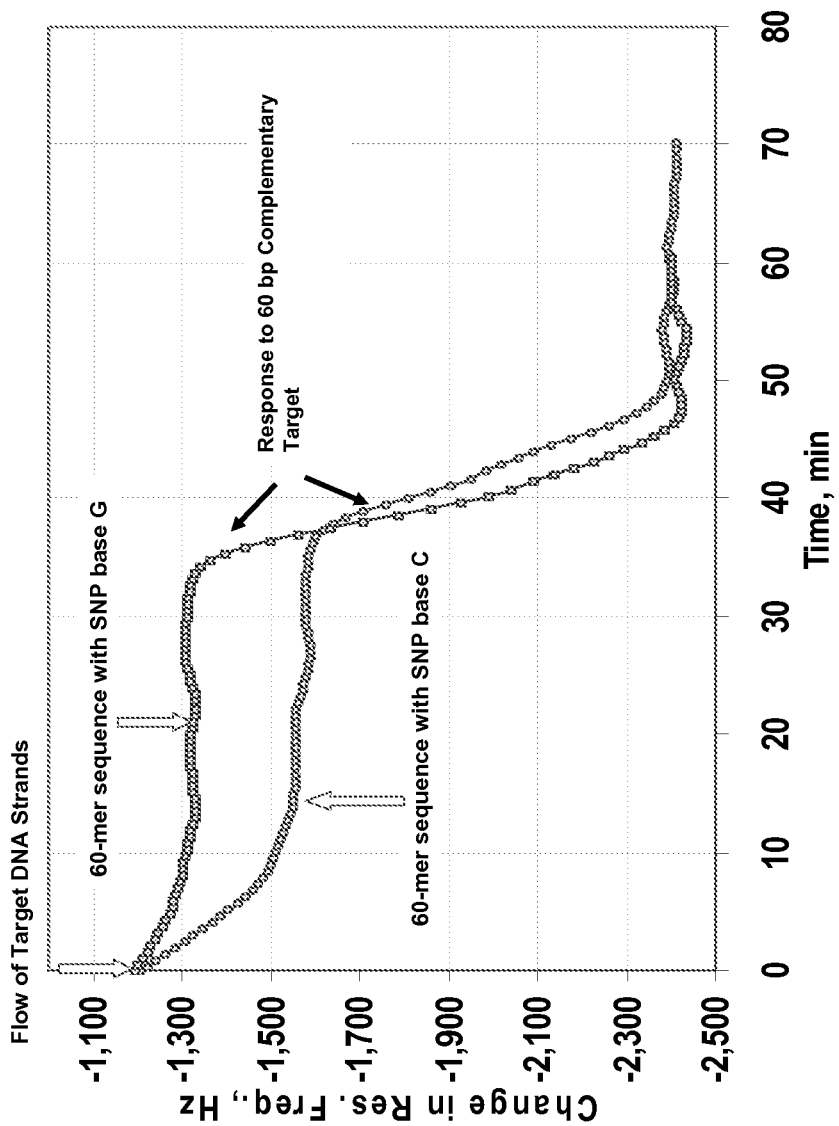
FIG. 32 is a plot illustrating example results from FIGS. 28 and 29.

The thermal stability of a double stranded ("dsDNA") depends on the base composition with percentage of GC content increasing the melting point, Tm of the strands. However, any mismatches on the dsDNA reduces its stability. Each base pair match can reduce the Tm by up to 5° C. for dsDNA of 14-20 bp in length. FIG. 32 shows the response by two 60 bp mismatched pairs; instead of the target having a base A to complement the base T on the probe, one target contained the base G (refereed to as SNP with G) and the other with base C (referred to as SNP with C). The plot for SNP with G has been shifted up to align with the chart for SNP with C for better comparison. FIG. 32 shows that when the DNA solution with SNP with C was flowed through, the sensor response was decreased of 121±22 Hz. When the same concentration of SNP with G was flowed through a similar sensor, the response was 366±18 Hz. This difference in response is due to the stability of A-C and A-G base pairs. The higher response for SNP with G is due to higher stability of A-G pair compared to that of A-C. The response actually matches what has been confirmed that the order of stability of mismatches has been determined to be A:T>G:A, G:T>T:T, A:A, C:T and C:A. FIG. 32 shows that when complementary target solution was flowed after flushing the sensor with TE buffer the total response for SNP with C was 1179±62 Hz compared to 1170±32 Hz for SNP with G; i.e. the unspecific hybridization of targets with SNPs still left equal number of sites (probes) for complementary targets to hybridize.

Figure 33:
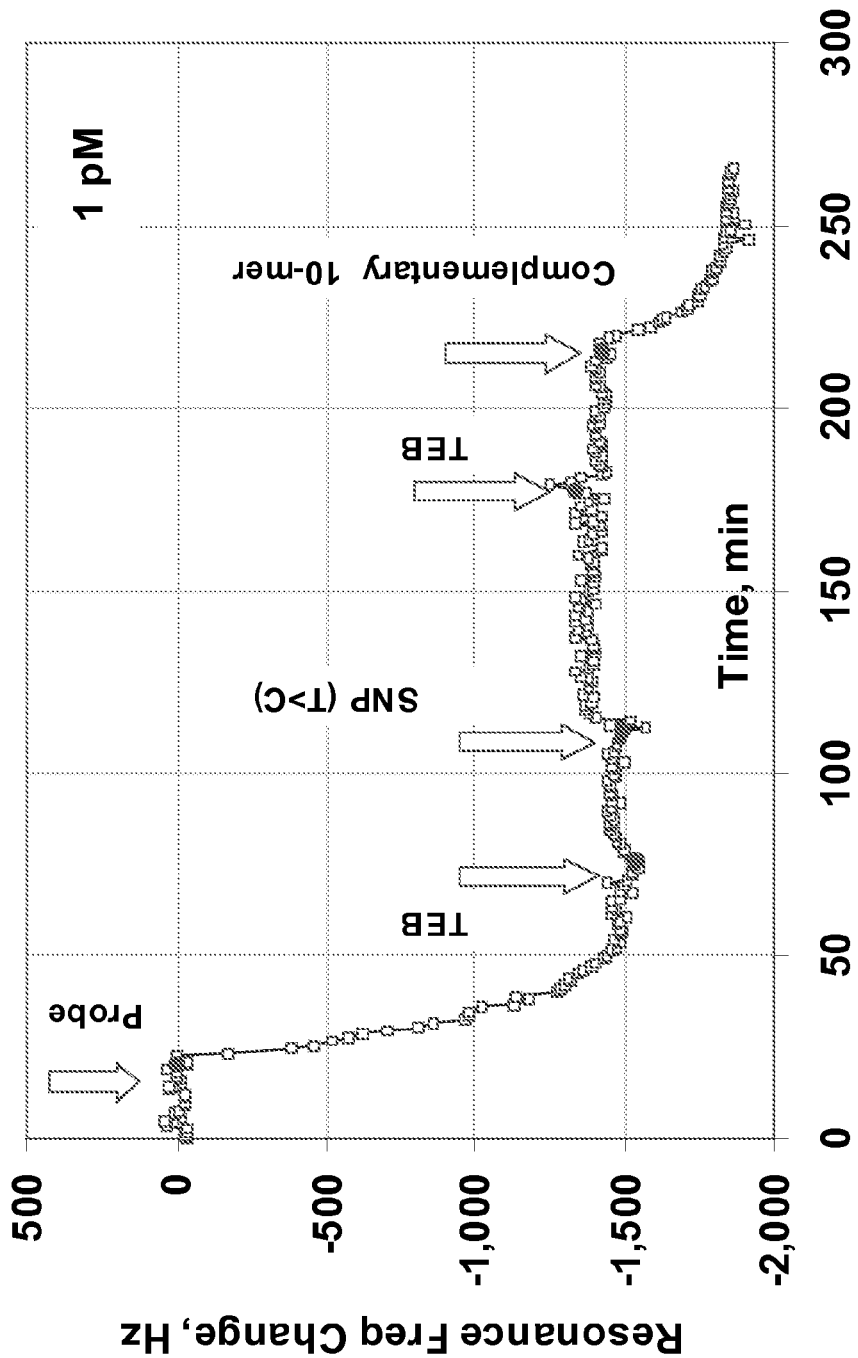
FIG. 33 is a plot illustrating example results of the detection of 1 pM 10-mer containing a SNP ("Mismatch 10-mer") as compared to the detection of a 10-mer without the SNP ("Complementary SNP").
Figure 34:
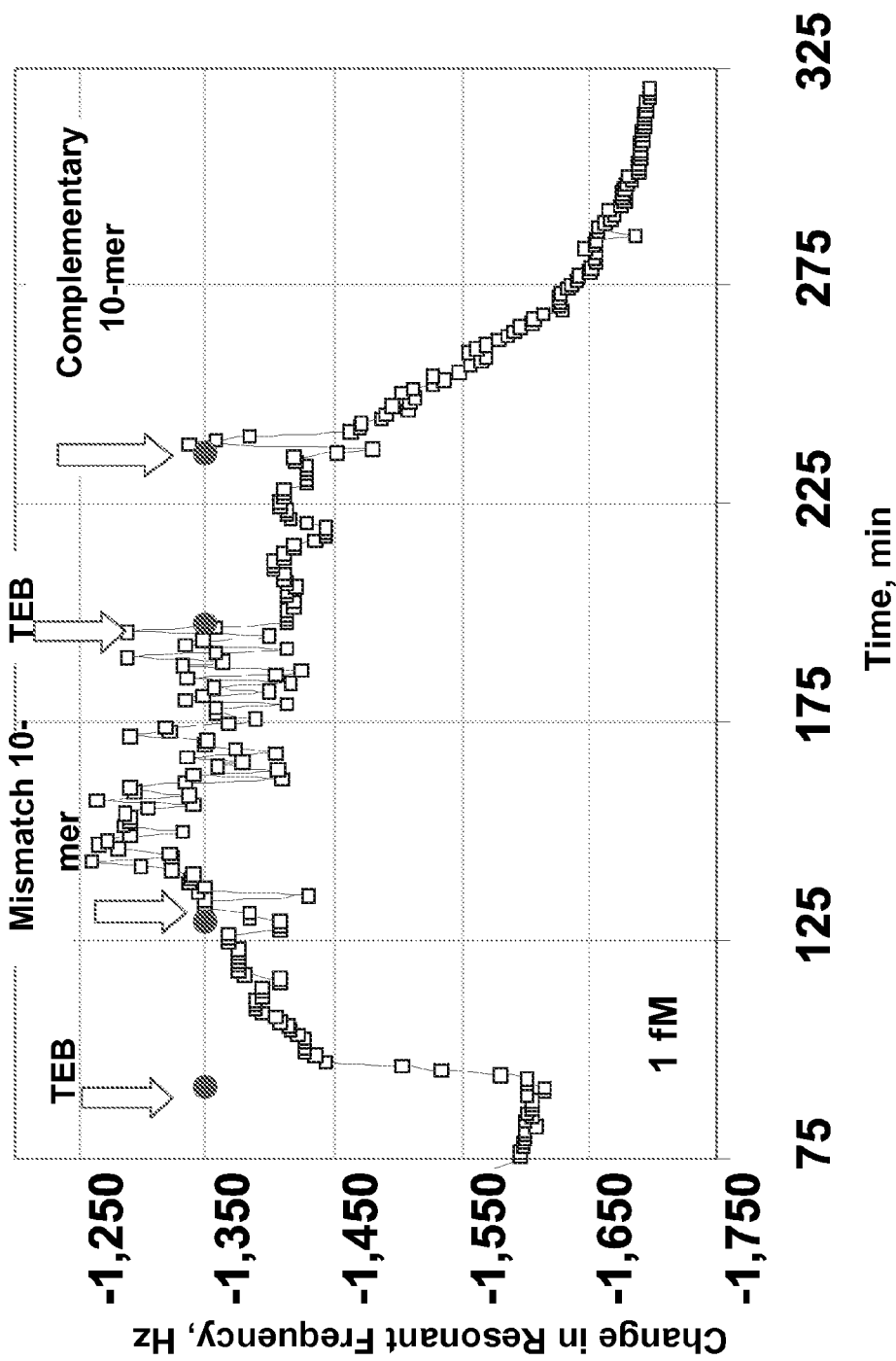
FIG. 34 is a plot illustrating example results of the detection of 1 fM 10-mer containing a SNP ("Mismatch 10-mer") as compared to the detection of a 10-mer without the SNP ("Complementary SNP").
Figure 35:
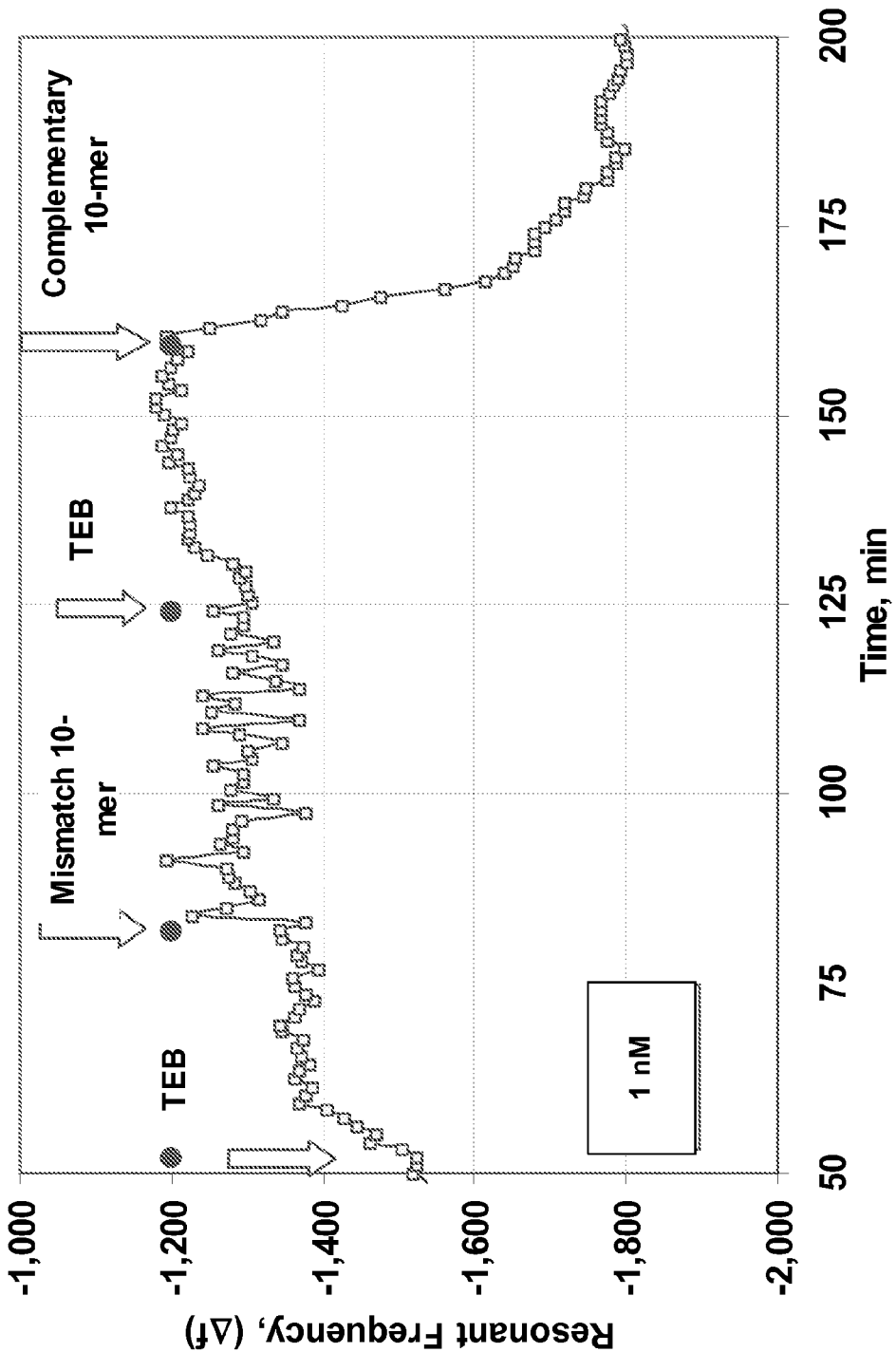
FIG. 35 is a plot illustrating example results of the detection of 1 nM 10-mer containing a SNP ("Mismatch 10-mer") as compared to the detection of a 10-mer without the SNP ("Complementary SNP").

FIG. 33 shows that 1 pM of a 10-mer target nucleic acid having the same base pair mismatch ("SNP T→C") (FIG. 27) as in do not bind to the probe material. Upon addition of the fully complementary 10-mer (i.e., the 10-mer without the T→C mismatch), there is a decrease in resonance frequency indicating that the fully complementary 10-mer hybridizes to the probe on the sensor. FIG. 33 and FIG. 35 are similar experiments as in FIG. 33 except that the target nucleic acid was present at either 1 fM or 1 nM, respectively. Further, FIG. 33 and FIG. 35 are similar experiments as in FIG. 33 do not depict the resonance frequency when the probe is added to the sensor as is shown in FIG. 33. The absence of a decrease in resonance frequency in the presence of the mismatch-containing target confirms that the target contains a SNP to the probe on the sensor. Moreover, the presence of a decrease in resonance frequency in the presence of the complementary 10-mer confirms the sequence of the probe nucleic acid.

The data in FIGS. 29-35 show the response to SNP Target (FIG. 27) and then to cTarget (FIG. 27) at various concentrations (1 fM, 1 pM, and 1 nM, respectively). The response to SNP Target shows a noisy response and when the buffer is introduced the sensor response shows much lower noise level, and when cTarget is introduced rapid resonance frequency decrease occurs indicating an increase in sensor mass due to hybridization. Accordingly, cantilever sensors may be used to determine whether target nucleic acid contains a SNP to the probe nucleic acid. It is to be understood that a two-step process may be used to determine whether a sample contains a target nucleic acid with a SNP of the probe nucleic acid. The first step comprises exposing a probe-containing sensor to target nucleic acid and measuring the resulting resonance frequency. The second step comprises exposing the probe-containing sensor to nucleic acid known to be complementary to the probe nucleic acid and measuring the resulting resonance frequency. Comparing the resulting resonance frequencies from steps 1 and 2 reveal the presence or absence of a SNP in the target nucleic acid. Where there is both (a) no decrease in resonance frequency after step 1 and (b) a decrease in resonance frequency after step 2; the target nucleic acid in step 1 contains a SNP of the probe nucleic acid. See FIGS. 32-35. Where there is (a) decrease in resonance frequency after both steps 1 and 2 and (b) the decrease in response to step 1 is to a lesser degree than the decrease in step 2; the target nucleic acid in step 1 contains a SNP of the probe nucleic acid. See FIGS. 28-32. Where there is a (a) decrease in resonance frequency after both steps 1 and 2 and (b) the decrease in response to step 1 is of the same magnitude as the decrease in step 2; the target nucleic acid does not contain a SNP of the probe nucleic acid.

Detection Using a Polymerase

Figure 36:
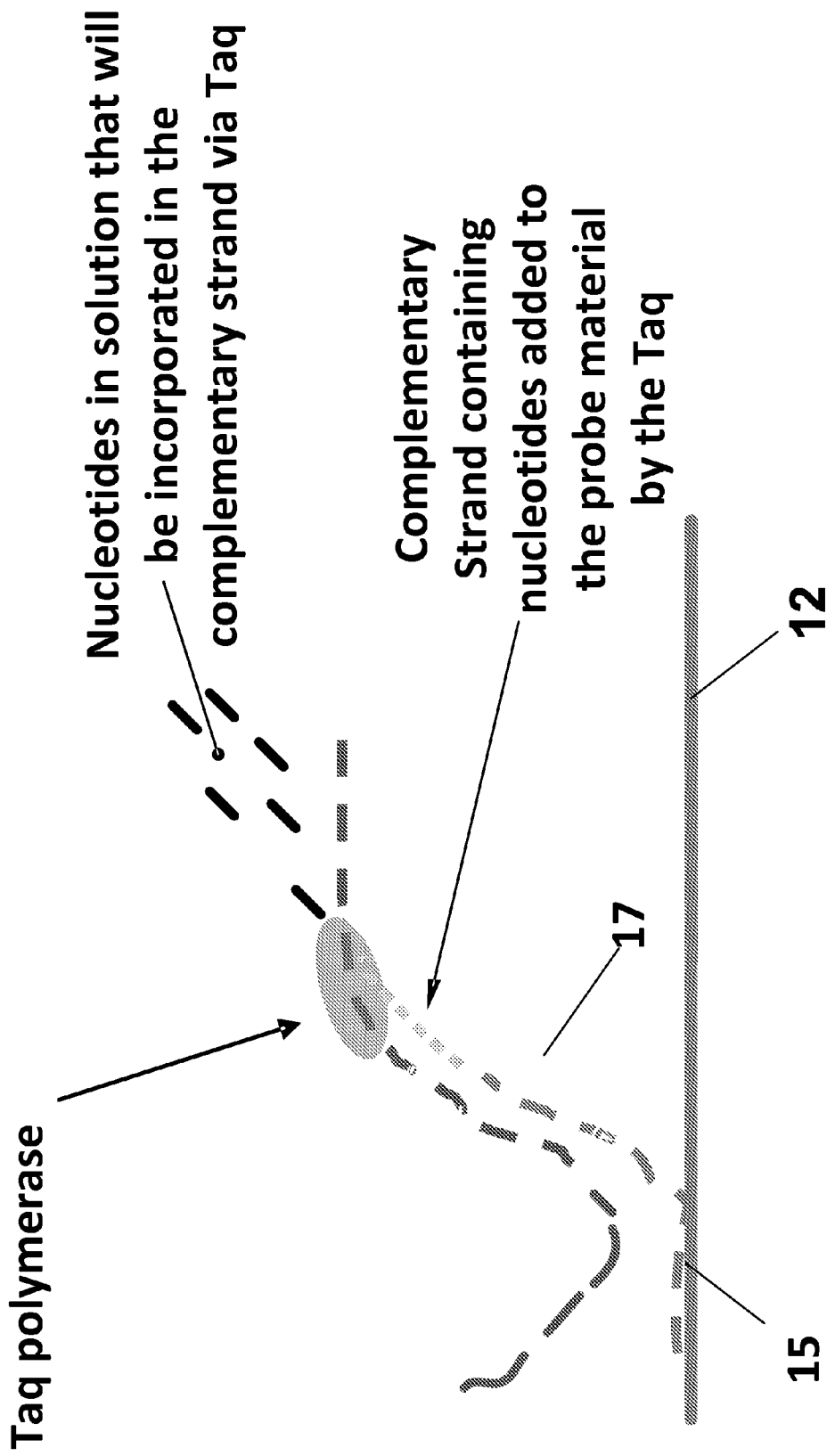
FIG. 36 illustrates using Taq polymerase to catalyzed the reaction adding at least one nucleotide to the nucleic acid portion of the probe material 15 (e.g., the DNA strand that is complementary ("Complementary Strand") to the target DNA 17).

FIG. 36 depicts how Taq polymerase can be used to add nucleotides to the nucleic acid portion of the probe material, which will be complementary to the corresponding portion of the target material. Taq polymerase can be used to assemble a complementary strand of the target nucleic acid 17 in situ. Although Taq polymerase is depicted in FIG. 36, any appropriate polymerase can be used.

Figure 37:
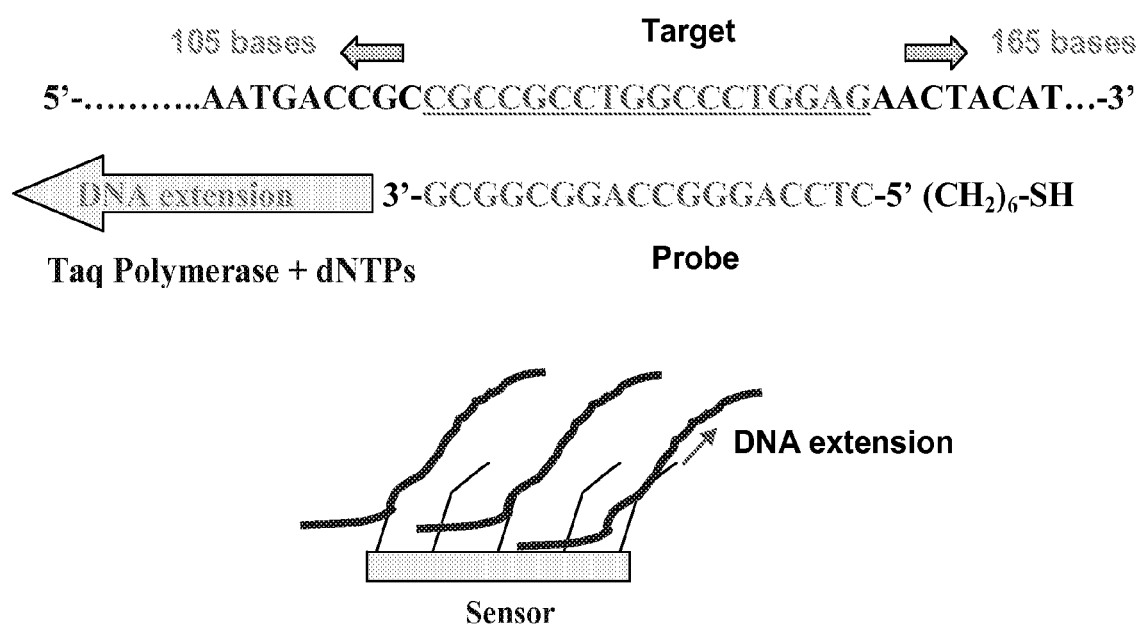
FIG. 37 is an illustration of an example of the reaction adding at least one nucleotide to the nucleic acid portion of the probe material (e.g., "DNA extension") (SEQ ID NO:16) using polymerase to increase mass on a cantilever sensor (SEQ ID NO:15).

Increased detection sensitivity was achieved by adding mass by reaction. As shown in FIG. 37, a probe contains 18 bases complementary to 18 bases on an amyloid precursor protein (APP) gene. 105 and 165 bases are on either side of the hybridization section as depicted in FIG. 37. The 3' end of the probe thus acts as starting point for DNA polymerization where Taq DNA Polymerase catalyzes incorporation of bases complementary to the template (target strand). Target and probe strands (respectively labeled in FIG. 37) are not depicted to scale. The arrow pointing away from the sensor in FIG. 37 indicates the direction of DNA extension. After the occurrence of extension, 20 base ssDNA complementary to 54-74 on APP did not give a hybridization response, thus indicating that DNA extension did take place in the direction.

The test involved a probe sequence immobilized on a cantilever sensor surface comprising 18-mer sequence HS-(CH$_2$)$_6$- 5'CTC CAGGG CCAGG CGGCG3' (SEQ ID NO:1) which hybridizes with position 105 to 124 in the APP gene. The probe that would hybridize to the complementary APP gene, and its complement HS—(CH$_2$)$_6$-5'CGCCGCCTG-GCCCTGGAG3' (SEQ ID NO:13) was also immobilized on the sensor. FIG. 37 shows the relative position of the sense strand. Once the APP gene is hybridized there are 105 bases towards 5' end of the target (APP gene) and 165 bases towards the 3' end. A Taq polymerase was used which extended the immobilized probe in 3→5 direction such that a maximum of 105 bases is added as shown in FIG. 37. The probe immobilized on the sensor comprises a sequence complementary to both of the denatured APP dsDNA. A freshly prepared 2 mL probe comprising both sequences in a 1:1 mole ratio at a concentration of 10 pM was flowed through the sensor after equilibrating the sensor in TE buffer.

Figure 38:
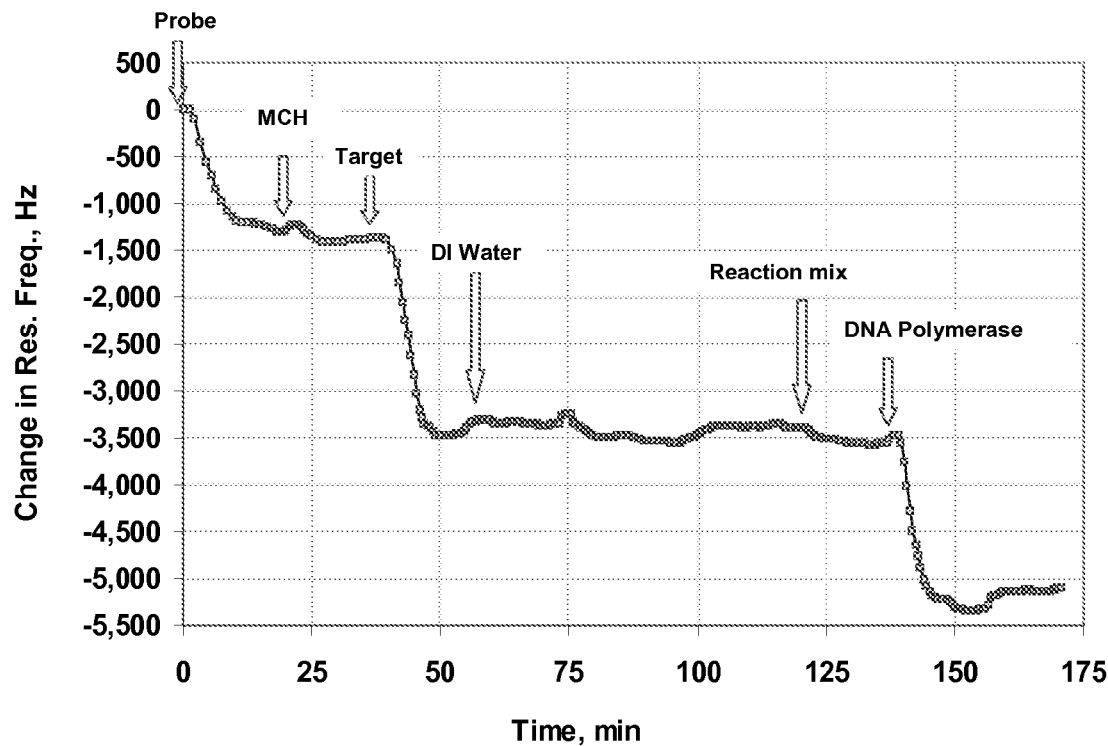
FIG. 38 is an example illustrative plot of the change in resonance frequency due to a change in mass resulting from DNA extension using polymerase.

As shown in FIG. 38, the flow of probe solution resulted in a decrease of 1,360 Hz. At t=23 minute, the flow was then switched to 2 mL of freshly prepared 1 µM MCH solution in TE buffer to fill unoccupied Au <111> sites and to remove any non-specifically attached probe strands. At t=40 min, 2 mL of 1 pM freshly denatured APP target in TE buffer was introduced. A change in resonance frequency, resulting in a decrease of 2,095 Hz in 11.1 min occurred. At t=55 min, nuclease free DI water was pumped in to purge the system of buffer and DNA. When DI water initially entered the flow-cell chamber, there was a slight increase in resonance frequency (150 Hz) and is concluded to be due to a small temperature change in the flow-cell (~0.2° C.). However, during the flow of DI water for 67 minutes (33.5 mL), the noise level was ±150 Hz but no overall change in resonance frequency occurred. At t=120 min, a freshly prepared 1.5 mL reaction mixture containing 150 µL 10× Taq buffer, 30 µL 10 mM dNTP with remaining DI water was flowed in. As soon as the mix entered the flow-cell, there was a decrease of −116±15 Hz within the first 5 minutes. It took approximately 4-5 minutes for the new target nucleic acid to completely replace the previous one in the flow cell. The rapid change in resonance frequency occurred with maximum reaching within the first 5 minutes indicates that this small change in resonance frequency is due to the density difference of the reaction mixture. Solution of dNTP in Taq buffer is denser than DI water. At t=140 min, 25 µL of Taq DNA polymerase is added to the circulating reaction mix and mixed thoroughly with a pipette. As the polymerase mixed in the resonance frequency rapidly decreased progressively resulting in 1,838±36 Hz in 11.4 minutes. This decrease in resonance frequency is due to the addition of mass on the sensor surface. When DNA Taq polymerase was not present in the reaction mix, there was no significant change in the resonance frequency; however, the presence of polymerase catalyzed the reaction of nucleotide addition, thus extending the probe to form double stranded DNA. The maximum change occurred in 11.4 minutes. Taq polymerase can add 60 nt/s at its optimum temperature. Good catalytic activity was observed at 70-75° C. At the chosen temperature of 46.2±0.1° C., the activity was lower by <5%. It is estimated that the reaction can add up to a maximum of approximately 6 nt/s. At this maximum rate it should take only ~18 seconds to extend all hybridized target to maximum once the chamber containing the sensor is filled with reaction mixture and the polymerase. Experimentally that it takes 5-6 minutes and indicates that the DNA extension is slow.

Figure 39:
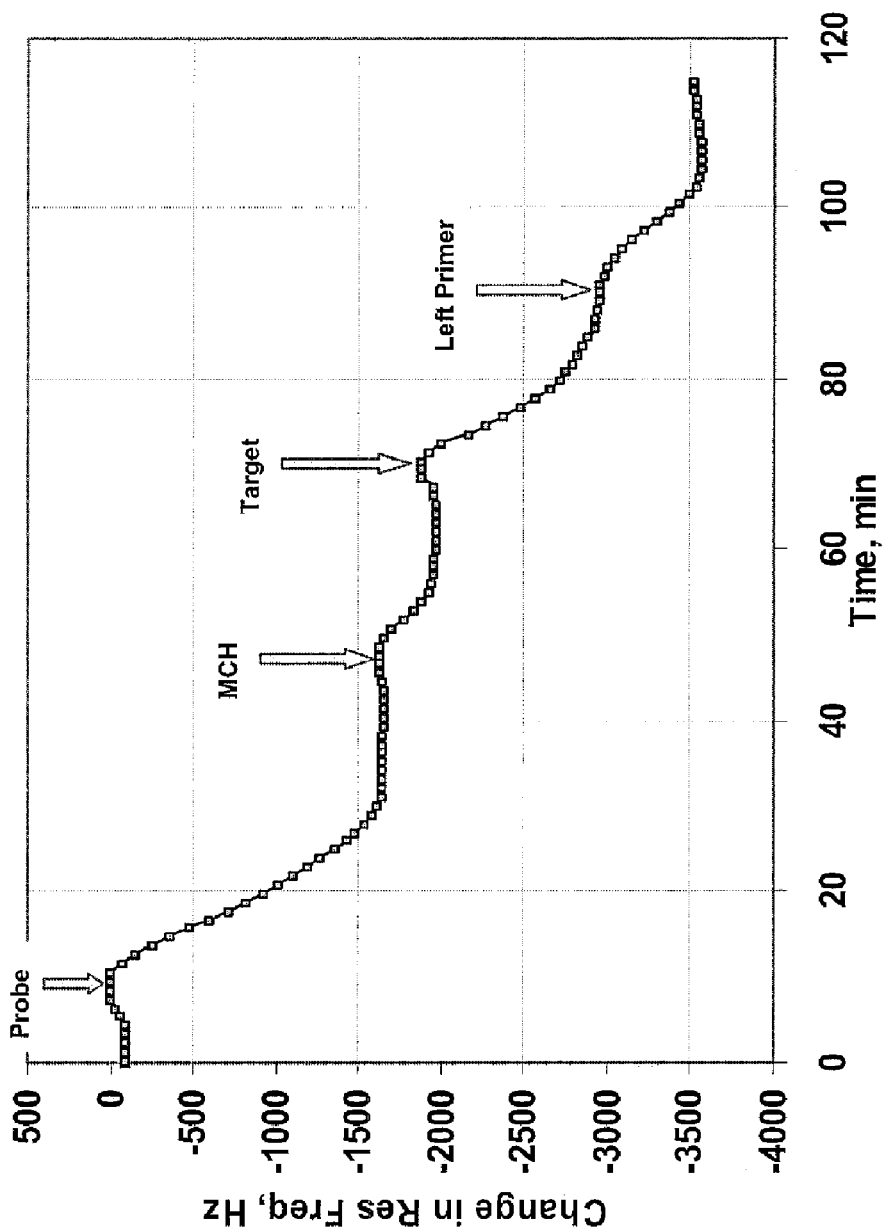
FIG. 39 is an example illustrative plot of the change in resonance frequency due to the binding of the target DNA to the probe material on the sensor surface, which is followed by the addition of another ssDNA ("Left Primer") having complementarity to the target DNA.

In FIG. 39 the probe solution comprised of 1 mL of 10 pM ssDNA each containing a section complementary to a section of the denatured ssDNA, a total of 2 mL of 10 pM mixed probe. The flow of probe solution resulted in a change of 1,830±12 Hz and is greater than the 1,360±27 Hz decrease obtained for the same concentration of probe in the previous section. Flow of 2 mL of 1 pM MCH then caused a 186±52 Hz decrease in frequency. Now, at t=34.7 min, 2 mL of 1 pM freshly denatured DNA target was flowed through the sensor. This caused a sharp change in resonance frequency resulting in a decrease of 1,935±26 Hz in 10.8±0.5 min. This value is close (−8%) to the one obtained in FIG. 38. To prepare the sensor for extension of probe, nuclease free DI water was pumped through the flowcell, at t=54 minute for 21 minutes at a high flow-rate with a total flush of 30 mL through the system. During this period, the response slowly increased by 68+17 Hz, suggesting either weakly adsorbed target was removed. At t=70.8 minute, 2 mL of reaction mixture containing 150 µL 10× Taq buffer, 30 µL 10 mM dNTP with remaining DI water was flowed through. Initially, Taq buffer caused a small decrease of ~110 Hz presumably due to density difference. At t=79 minute, 25 µL of Taq polymerase was added to the circulating reaction mix which resulted in an immediate and rapid decrease of resonance frequency resulting in a change of 1,403±28 Hz in 8.9 minutes. As in FIG. 38, this change is due to extension of the probe forming double stranded DNA in the 5->3 direction of the probe. At t=101 minute, TE buffer that is used for hybridization of the target was flowed in an once through fashion and flush the reaction mix out of the flow-cell. This resulted in a small increase in resonance frequency (~90 Hz).

Figure 40:
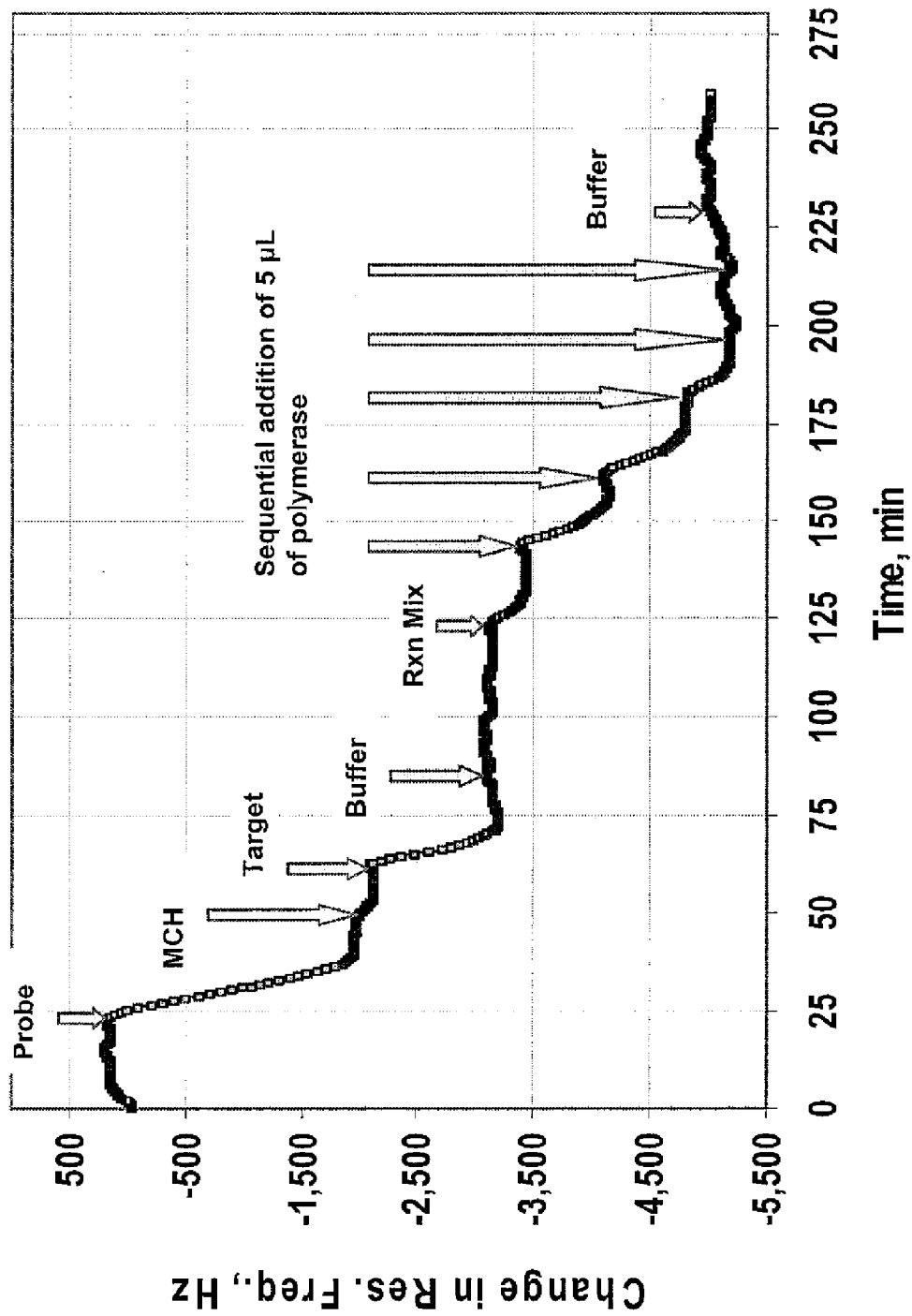
FIG. 40 is an example illustrative plot of the change in resonance frequency due to a change in mass resulting from DNA extension using sequential addition of polymerase.
Figure 41:
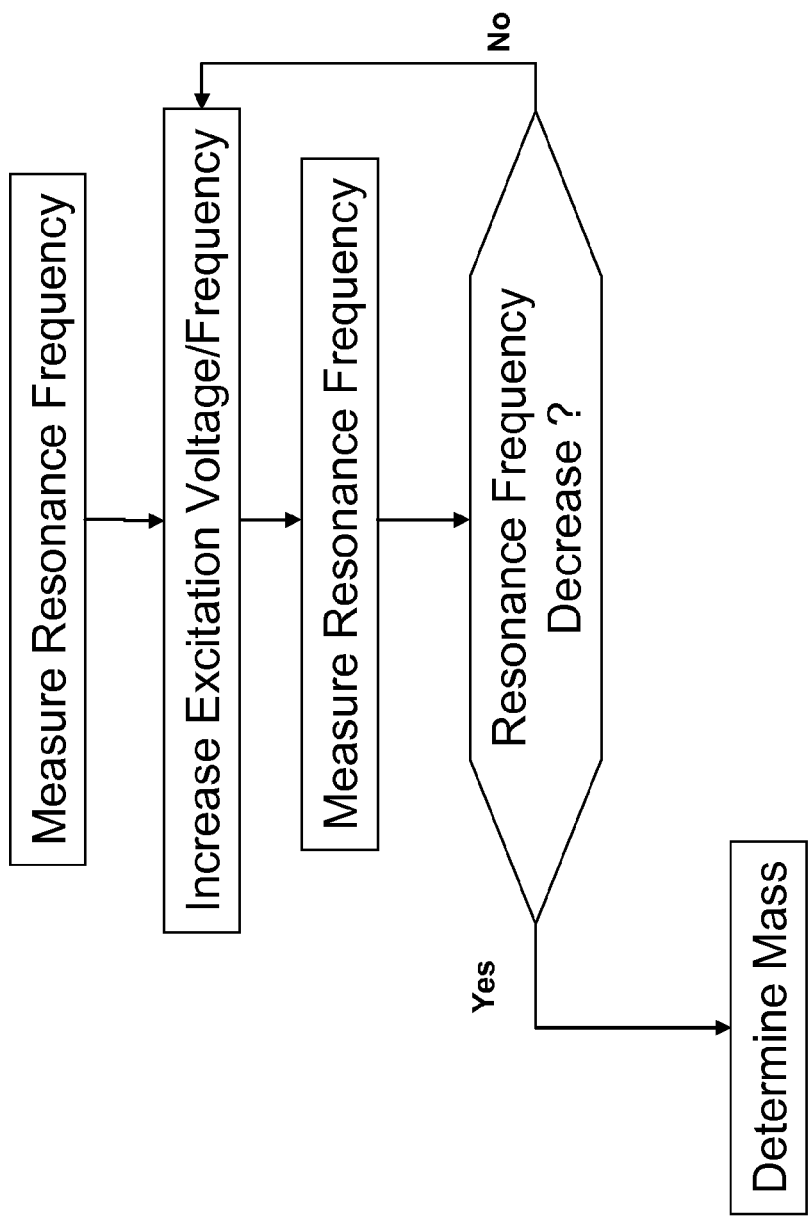
FIG. 41 flow diagram of an example process for confirming the binding of target nucleic acid and probe material using a cantilever sensor.

Taq polymerase replicates DNA beginning at any single-stranded double-stranded junction with replication starting at the 3' of the primer initiated by the 3'-OH of the primer. DNA polymerase adds dNTPs onto the primer such that complementary bases are added taking into account the hydrogen bonding between the bases in two strands. In addition, an optimum quantity of polymerase is required to catalyze a reaction, a lack of which will stop polymerization of nucleotides. FIG. 40 depicts an experiment where instead of adding 25 µL DNA polymerase to the reaction mix at once, 5 µL of it was added sequentially. The reaction steps up to hybridization of 2 mL 1 µM target are similar to that of FIG. 39. At time t=124 minute, reaction mix without DNA polymerase was flowed through the sensor and it resulted in a decrease of 217±22 Hz which is approximately 100 Hz more than the response obtained earlier for the same solution which we attributed to a mechanical disturbance that was noted during opening and closing of the valves. At t=145 minute, 5 µL of DNA polymerase was mixed with the circulating reaction mix. As soon as the polymerase entered the chamber, there was a rapid decrease in resonance frequency resulting in a change of 768±21 Hz in 11.1±0.5 minutes. Subsequent addition of 5 µL of DNA polymerase resulted in further decrease of 685±12 Hz in 10.3±0.5 minutes. The next addition caused a decrease of 621±9 Hz in 6.2±0.5 minutes. The fourth and fifth additions, however, resulted in no change in frequency. Also, when TE buffer was once again flowed at t=225 minute, there was a slight increase in resonance frequency (58±21 Hz) but no ultimate change in any direction. 15 µL of DNA polymerase is sufficient to catalyze the dNTPs present in the solution or additionally, 15 µL of DNA polymerase is sufficient to incorporate bases to the available sites and after that either no more sites are available or they are not accessible or they have already been extended.

Dehybridization by Mechanical Disruption

When excitation is increased from normal 100 mV to 1 V, the PZT extends by about 10-fold longer, which demonstrates that the magnitude of oscillation increases as given by tip deflection in first mode, $\delta(L)$ that is estimated from: $\delta(L) = (E_g E_p t_g t_p L^2 \ (t_p+t_g)/2DL_p(E_p t_p+E_g t_g))d_{31}V$, where E is Young's modulus, t is thickness, L is length. Subscripts g and p refer to glass and PZT, respectively. L is overall sensor length, D is bending modulus per unit width, $d_{31}$ is piezoelectric constant. Since dynamic deflection is proportional to static deflection, when V is increased by ten-fold, tip deflection, and thus the acceleration of the sensor surface is also increased ten-fold. Because the sensor surface displacement increases, at a given frequency, acceleration is the second derivative of $\delta_L \sin(27 \text{ ft})$ where t is time, also increases. That is, acceleration of sensor surface is directly proportional to the excitation voltage, V and to the square of the resonance frequency. Accordingly, an increase in excitation voltage approximates as increasing the "pull force" between the sensor surface and what is attached to it. The "pull force" is sufficient to dehybridize a hybridized strand. Such "pull force" can similarly applied to other sensors (not just limited to cantilever sensors) in a fashion to achieve dehybridization. This method of dehybridization is different from the current methods used in the field; namely, salt or buffer concentration and temperature.

Figure 42:
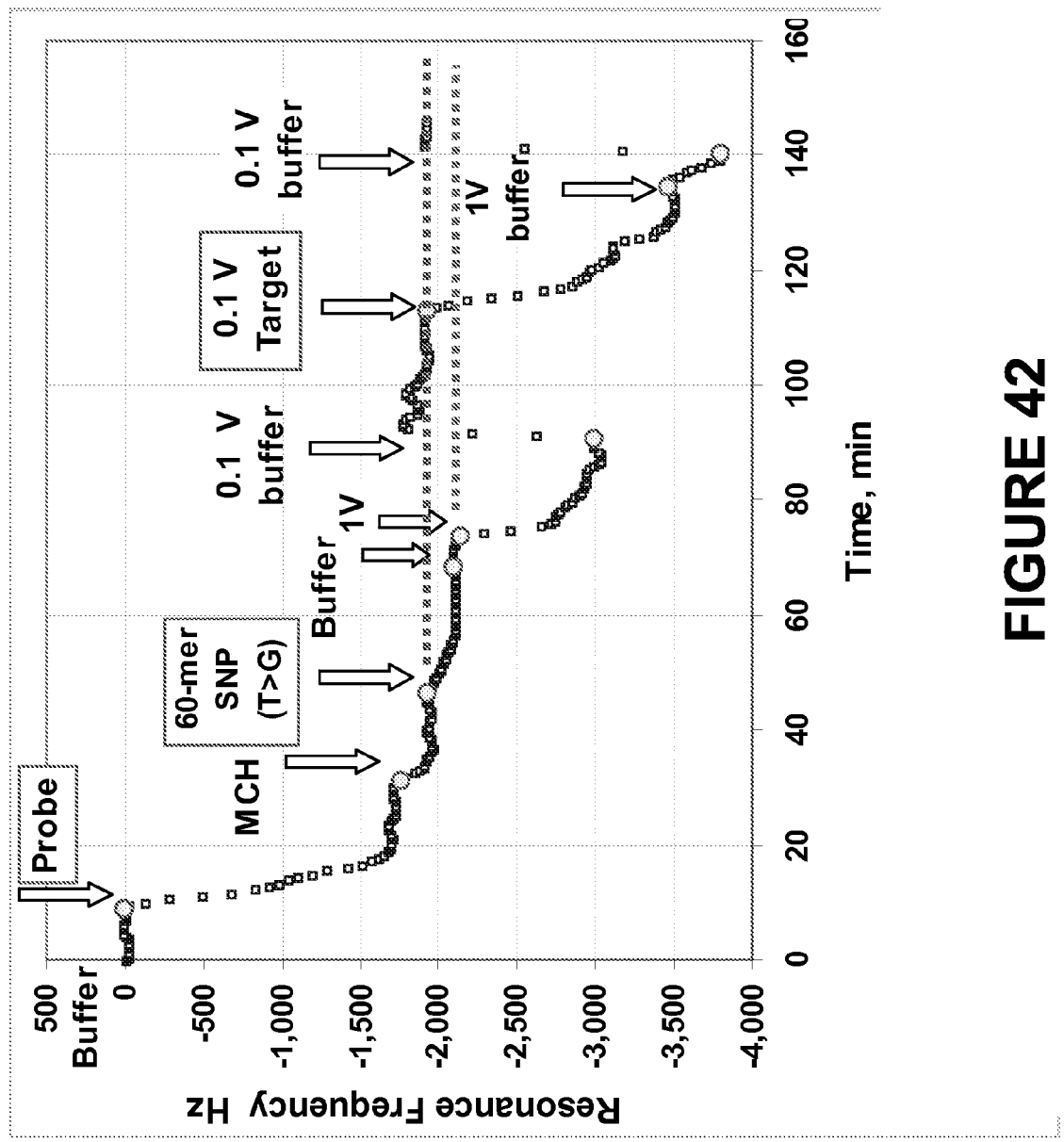
FIG. 42 is a plot illustrating dehybridization by mechanical means as opposed to chemical or temperature means.

FIG. 42 shows a sample result of using a increase in excitation voltage to increase "pull force" and dehybridize or denature the probe and target nucleic acids. A sample result is shown in FIG. 42. The probe ($HSC_6H_{12}$-5'GGA AGA AGC TTG CTT3') (SEQ ID NO:3) is first immobilized (1 pM, 2 mL) that causes a 1720 Hz shift down, followed by MCH (1 mM, 2 mL) to stabilize the probe and to fill in empty sites. At 46 min, 2 mL of 10 pM 60-mer SNP (T>G) 5'-ACC CGT CCG CCA CTC GTC AGC AAA GAA CCG ACC TTC TTC CTG TTA CCG TTC GAC TTG CAT-3' (SEQ ID NO:7) which causes a weak hybridization with a response of 160 Hz. The bold nucleotides depict the region of the target nucleic acid that is complementary to the probe nucleic acid, expect for the presence of the T>G, which is underlined. After a buffer flush, excitation voltage is increased to 1 V, and the sensor responds by decrease in resonance frequency due to added mass of surrounding fluid and shortly after that excitation level is reduced to 0.1 V and resonance frequency increases to pre-hybridization value; the upper-most, horizontal dotted line indicates the closeness of recovery. Introducing 2 mL of 10 pM 60-mer complementary strand results in strong hybridization that occurs with ~1580 Hz shift down. At 133 min, excitation again is increased and then it is returned to 0.1 V, and one notes the recovery is back to −1920 Hz which is within experimental error to prehybridization value of −1938 Hz, and is indicated by the upper-most, dotted horizontal line. Similar results were observed with 60-mer SNP (T>C), 30-mer SNP (T>G), 20-mer SNP (T>G).

While illustrative embodiments of enhanced sensitivity of a cantilever sensor via a plurality of specific bindings have been described herein, it is to be understood that other similar embodiments can be used or modifications and additions can be made to the described embodiment of a cantilever sensor to detect nucleic acid hybridization and dehybridization. Therefore, detection of nucleic acid hybridization and dehybridization should not be limited to any single embodiment, but rather should be construed in breadth and scope in accordance with the appended claims.

What is claimed is:

1. A method comprising:

immobilizing a probe material to a non-piezoelectric layer surface of a sensor, wherein the probe material is bindable to a target nucleic acid, the sensor comprising:
  a piezoelectric layer comprising a proximate end and a distal end;
  a base portion coupled to the proximate end of the piezoelectric layer;
  the non-piezoelectric layer, wherein:
    at least a portion of the piezoelectric layer is coupled to at least a portion of the non-piezoelectric layer such that the piezoelectric layer and the non-piezoelectric layer are not coextensive; and
    the base portion is not attached to the non-piezoelectric layer; and
  electrodes operatively associated with the piezoelectric layer for measuring resonance frequency of the sensor;
measuring, via the electrodes, a first resonance frequency of the sensor;
exposing the sensor surface, having the probe material immobilized thereon, to the target nucleic acid;
measuring, via the electrodes, a second resonance frequency of the sensor, wherein the first resonance frequency is measured prior to the exposing and the second resonance frequency is measured subsequent to the exposing;
determining, via a comparison of the first resonance frequency and the second resonance frequency, an amount of total mass sensed by the sensor via the exposure; and
determining a portion of the total mass attributable to the target nucleic acid.

2. The method in accordance with claim 1, wherein the target nucleic acid comprises one nucleotide that is not complementary to a corresponding nucleotide of the probe material.

3. The method in accordance with claim 1, wherein the target nucleic acid is complementary to the probe material.

4. The method in accordance with claim 1, further comprising a polymerase, wherein a portion of the total mass is attributable to the polymerase.

5. The method in accordance with claim 4, wherein the polymerase catalyzes a reaction that results in adding at least one nucleotide to the probe material.

6. The method in accordance with claim 5, wherein the reaction occurs at a constant temperature.

7. The method in accordance with claim 5, wherein the reaction occurs in the absence of thermal cycling.

8. The method in accordance with claim 5, wherein the reaction occurs at room temperature.

9. The method in accordance with claim 1, further comprising determining a characteristic of a binding between the target nucleic acid and the probe material.

10. The method in accordance with claim 9, wherein the characteristic is indicative of complementary base paring.

11. The method in accordance with claim 9, wherein the characteristic is indicative of a base pair mismatch.

12. The method in accordance with claim 1, wherein the target nucleic acid is present at a concentration between about 1 aM and about 1 µM.

13. The method in accordance with claim 12, wherein the target nucleic acid is present at a concentration between about 1 fM to about 1 pM.

14. The method in accordance with claim 1, wherein the target nucleic acid is present in a complex solution.

15. The method in accordance with claim 14, wherein the complex solution comprises at least one of proteins, lipids, sugars, DNA, or RNA.

16. The method in accordance with claim 1, further comprising confirming a binding between the target nucleic acid and the probe material by:
    measuring the first resonance frequency of the sensor;
    increasing an electrical parameter of excitation of the sensor;
    measuring the second resonance frequency of the sensor; and
    comparing the first resonance frequency and the second resonance frequency to determine whether there is a difference between the first resonance frequency and the second resonance frequency.

17. The method in accordance with claim 16, further comprising, when a difference is detected, determining an amount of target nucleic acid on the sensor.

18. The method in accordance with claim 16, further comprising, when the difference is not detected:
    repeating the increasing and comparing until a difference is detected; and
    determining an amount of nucleic acid on the sensor.

19. The method in accordance with claim 16, wherein the difference is indicative of a target nucleic acid denaturing from the probe material.

20. The method in according with claim 16, wherein the difference is indicative of an amount of target nucleic acid that was hybridized to the probe material.

21. The method in accordance with claim 1, wherein the sensor comprises a cantilever sensor.

22. The method in accordance with claim 1, further comprising:
    comparing the first resonance frequency and the second resonance frequency to determine whether there is a difference between the first resonance frequency and the second resonance frequency.

23. The method in accordance with claim 22, wherein a difference is detected, the method further comprising determining an amount of nucleic acid on the piezoelectric sensor.

24. The method in accordance with claim 22, wherein a difference is not detected, the method further comprising:
    repeating until a difference is detected:
    (i) increasing an electrical parameter of excitation of the sensor;
    (ii) measuring a second resonance frequency of the sensor; and
    (iii) comparing the first resonance frequency and the second resonance frequency to determine whether there is a difference between the first resonance frequency and the second resonance frequency and
    determining an amount of nucleic acid on the piezoelectric sensor based on the difference.

25. The method in accordance with claim 22, wherein the difference is indicative of a target nucleic acid denaturing from probe material.

26. The method in accordance with claim 22, wherein the difference is indicative of an amount of target nucleic acid that was hybridized to a probe material.

27. The method in accordance with claim 1, further comprising:
    determining a difference between the second resonance frequency and the fourth resonance frequency; and
    determining if dehybridization between the target nucleic acid and the probe material has occurred in accordance with a value of the difference.

28. The method in accordance with claim 27, wherein a zero value of difference is indicative of lack of dehybridization between the target nucleic acid and the probe material.

29. The method in accordance with claim 1,
    wherein the target nucleic acid is present in a fluid flow field and the method further comprises applying vibration to the sensor surface that introduces surface displacement and acceleration.

* * * * *

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Probe

<400> SEQUENCE: 1
ctccagggcc aggcggcg                                                  18

<210> SEQ ID NO 2
<211> LENGTH: 288
<212> TYPE: DNA
<213> ORGANISM: Artificial Sequence
<220> FEATURE:
<223> OTHER INFORMATION: 288-mer section of the amyloid beta precursor
      protein gene ("APP gene")

<400> SEQUENCE: 2
catttccagg agaaagtgga atctttggaa caggaagcag ccaacgagag acagcagctg      60
gtggagacac acatggccag agtggaagcc atgctcaatg accgccgccg cctggccctg     120
gagaactaca tcaccgctct gcaggctgtt cctcctcggc ctcgtcacgt gttcaatatg     180
ctaaagaagt atgtccgcgc agaacagaag gacagacagc acaccctaaa gcatttcgag     240
catgtgcgca tggtggatcc caagaaagcc gctcagatcc ggtcccag                  288

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
ggaagaagct tgctt                                                     15

<210> SEQ ID NO 4
<211> LENGTH: 10
<212> TYPE: DNA
<213> ORGANISM: Bacillus

<400> SEQUENCE: 4
aagcaagctt                                                           10
```

```
<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ccactctgac accatcctc                                                    19

<210> SEQ ID NO 6
<211> LENGTH: 60
<212> TYPE: DNA
<213> ORGANISM: Escherichia coli

<400> SEQUENCE: 6
acccgtccgc cactcgtcag caaagaagca agcttcttcc tgttaccgtt cgacttgcat       60

<210> SEQ ID NO 7
<211> LENGTH: 60
<212> TYPE: DNA
<213> ORGANISM: Escherichia coli

<400> SEQUENCE: 7
acccgtccgc cactcgtcag caaagaagcg agcttcttcc tgttaccgtt cgacttgcat       60

<210> SEQ ID NO 8
<211> LENGTH: 60
<212> TYPE: DNA
<213> ORGANISM: Escherichia coli

<400> SEQUENCE: 8
acccgtccgc cactcgtcag caaagaagcc agcttcttcc tgttaccgtt cgacttgcat       60

<210> SEQ ID NO 9
<211> LENGTH: 30
<212> TYPE: DNA
<213> ORGANISM: Escherichia coli

<400> SEQUENCE: 9
gtcagcaaag aagcaagctt cttcctgtta                                        30

<210> SEQ ID NO 10
<211> LENGTH: 30
<212> TYPE: DNA
<213> ORGANISM: Escherichia coli

<400> SEQUENCE: 10
gtcagcaaag aagcgagctt cttcctgtta                                        30

<210> SEQ ID NO 11
<211> LENGTH: 20
<212> TYPE: DNA
<213> ORGANISM: Escherichia coli

<400> SEQUENCE: 11
caaagaagca agcttcttcc                                                   20

<210> SEQ ID NO 12
<211> LENGTH: 20
<212> TYPE: DNA
<213> ORGANISM: Escherichia coli

<400> SEQUENCE: 12
```

-continued

```
caaagaagcg agcttcttcc                                              20

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
cgccgcctgg ccctggag                                                18

<210> SEQ ID NO 14
<211> LENGTH: 10
<212> TYPE: DNA
<213> ORGANISM: Bacillus

<400> SEQUENCE: 14
aagccagctt                                                         10

<210> SEQ ID NO 15
<211> LENGTH: 35
<212> TYPE: DNA
<213> ORGANISM: Artificial Sequence
<220> FEATURE:
<223> OTHER INFORMATION: Segment of amyloid precursor protein (APP) gene

<400> SEQUENCE: 15
aatgaccgcc gccgcctggc cctggagaac tacat                             35

<210> SEQ ID NO 16
<211> LENGTH: 18
<212> TYPE: DNA
<213> ORGANISM: Artificial Sequence
<220> FEATURE:
<223> OTHER INFORMATION: Probe

<400> SEQUENCE: 16
ctccagggcc aggcggcg                                                18
```